(12) United States Patent
Tanabe et al.

(10) Patent No.: US 11,259,520 B2
(45) Date of Patent: Mar. 1, 2022

(54) STEM CELL MANUFACTURING SYSTEM, STEM CELL INFORMATION MANAGEMENT SYSTEM, CELL TRANSPORT APPARATUS, AND STEM CELL FROZEN STORAGE APPARATUS

(71) Applicants: FANUC CORPORATION, Yamanashi (JP); I Peace, Inc., Palo Alto, CA (US)

(72) Inventors: Koji Tanabe, Palo Alto, CA (US); Kiyonori Inaba, Yamanashi (JP); Masaru Oda, Yamanashi (JP)

(73) Assignees: FANUC CORPORATION, Yamanashi (JP); I PEACE, INC., Palo Alto, CA (US)

( * ) Notice: Subject to any disclaimer, the term of this patent is extended or adjusted under 35 U.S.C. 154(b) by 573 days.

(21) Appl. No.: 15/442,755

(22) Filed: Feb. 27, 2017

(65) Prior Publication Data
US 2018/0035661 A1 Feb. 8, 2018

Related U.S. Application Data

(63) Continuation-in-part of application No. 15/228,017, filed on Aug. 4, 2016, now Pat. No. 10,354,218, and
(Continued)

(51) Int. Cl.
*C12M 1/36* (2006.01)
*C12M 1/00* (2006.01)
(Continued)

(52) U.S. Cl.
CPC ......... *A01N 1/0242* (2013.01); *A01N 1/0257* (2013.01); *A01N 1/0268* (2013.01);
(Continued)

(58) Field of Classification Search
CPC .............................. C12M 23/42; C12M 41/48
See application file for complete search history.

(56) References Cited

U.S. PATENT DOCUMENTS

| 5,022,236 A | * | 6/1991 | Knippscheer | ........ A01N 1/0263 |
| | | | | 165/104.21 |
| 5,325,678 A | | 7/1994 | Borah et al. | |

(Continued)

FOREIGN PATENT DOCUMENTS

| CN | 102174395 A | 9/2011 |
| CN | 205794637 U | 12/2016 |

(Continued)

*Primary Examiner* — William H. Beisner
(74) *Attorney, Agent, or Firm* — Hauptman Ham, LLP

(57) ABSTRACT

A stem cell manufacturing system for manufacturing stem cells from somatic cells includes: one or more closed production device(s) configured to produce stem cells from somatic cells; one or more drive device(s) configured to be connected with the production device(s) and drive the production device(s) in such a manner as to maintain the production device(s) in an environment suitable for producing stem cells; one or more cryopreservation device(s) configured to cryopreserve the produced stem cells; a first memory device configured to store whether or not somatic cells have been introduced to the production device(s), as a first state; a second memory device configured to store whether or not the production device(s) is/are connected with the drive device(s), as a second state; and a third memory device configured to store whether or not the produced stem cells can be placed in the cryopreservation device(s), as a third state.

32 Claims, 39 Drawing Sheets

Related U.S. Application Data a continuation-in-part of application No. 15/228,022, filed on Aug. 4, 2016, now Pat. No. 10,373,109.

(51) Int. Cl.

| | | |
|---|---|---|
| *C12M 1/26* | (2006.01) | |
| *C12M 1/34* | (2006.01) | |
| *C12M 1/02* | (2006.01) | |
| *A01N 1/02* | (2006.01) | |
| *G16H 10/60* | (2018.01) | |
| *G16B 25/00* | (2019.01) | |
| *G16H 10/40* | (2018.01) | |
| *G16H 40/63* | (2018.01) | |
| *G16B 25/10* | (2019.01) | |

(52) U.S. Cl.
CPC ............ *C12M 33/00* (2013.01); *C12M 41/12* (2013.01); *C12M 41/44* (2013.01); *C12M 41/48* (2013.01); *C12M 45/20* (2013.01); *C12M 45/22* (2013.01); *G16B 25/00* (2019.02); *G16B 25/10* (2019.02); *G16H 10/40* (2018.01); *G16H 10/60* (2018.01); *G16H 40/63* (2018.01); *C12M 1/02* (2013.01)

(56) References Cited

U.S. PATENT DOCUMENTS

| | | | |
|---|---|---|---|
| 5,985,653 A * | 11/1999 | Armstrong | ............ C12M 23/42 435/286.1 |
| 6,226,997 B1 | 5/2001 | Vago | |
| 2005/0276792 A1 | 12/2005 | Kaminski et al. | |
| 2008/0215364 A1 | 9/2008 | Brevnova et al. | |
| 2010/0272694 A1 | 10/2010 | Yang et al. | |
| 2011/0054929 A1 | 3/2011 | Centeno | |
| 2011/0207209 A1* | 8/2011 | Hammons | ............ C12M 23/42 435/297.1 |
| 2013/0275236 A1 | 10/2013 | Koke et al. | |
| 2013/0325492 A1 | 12/2013 | Dudzinski et al. | |
| 2013/0345094 A1* | 12/2013 | Noggle | ................ C12N 5/0696 506/14 |
| 2014/0278499 A1 | 9/2014 | Bowman et al. | |
| 2015/0203297 A1 | 7/2015 | Manning et al. | |
| 2015/0204598 A1 | 7/2015 | Affleck et al. | |
| 2015/0356500 A1 | 12/2015 | Larson et al. | |
| 2016/0114326 A1* | 4/2016 | Schryver | .................. B01L 7/04 62/465 |
| 2016/0222355 A1 | 8/2016 | Noggle et al. | |
| 2016/0328521 A1 | 11/2016 | Mickles et al. | |
| 2017/0299248 A1 | 10/2017 | High et al. | |
| 2017/0337337 A1 | 11/2017 | Heckerman et al. | |

FOREIGN PATENT DOCUMENTS

| | | |
|---|---|---|
| JP | 2002027983 A | 1/2002 |
| JP | 2003108660 A | 4/2003 |
| JP | 2004119 A | 1/2004 |
| JP | 2004290134 A | 10/2004 |
| JP | 2004290147 A | 10/2004 |
| JP | 2005-112499 A | 4/2005 |
| JP | 2005285142 A | 10/2005 |
| JP | 2008-283972 A | 11/2008 |
| JP | 2011013752 A | 1/2011 |
| JP | 2012-243324 A | 12/2012 |
| JP | 2015502747 A | 1/2015 |
| JP | 2015100309 A | 6/2015 |
| JP | 2015130805 A | 7/2015 |
| JP | 2015-202918 A | 11/2015 |
| JP | 2015222539 A | 12/2015 |

* cited by examiner

FIG. 19

| DONOR ID | INFORMED CONSENT | NATIONALITY | ADDRESS | SEX | AGE | BLOOD TYPE | ANAMNESIS | PRESCRIPTION HISTORY | ID OF FAMILY MEMBER FROM WHOM STEM CELLS WERE PRODUCED IN THE PAST |
|---|---|---|---|---|---|---|---|---|---|
| 0102 | Yes | United States of America | Hanover St., Palo Alto, CA 94304 | Male | 34 | A | None | None | 0124 |
| 0023 | Yes | Japan | Oshino-Mura,Yamanashi Prefecture,401-0597 | Male | 48 | O | Hepatitis | Entecavir | 0815 |
| 0085 | Yes | Germany | Effnerstr. 92, 81925 München | Female | 52 | B | Diabetes | Nateglinide | 0351 |
| ... | ... | ... | ... | ... | ... | ... | ... | ... | ... |

500

COLLECTING INSTITUTION ID

| | COLLECTING INSTITUTION | COLLECTING SITE | FIRST COLLECTABLE DATE | SECOND COLLECTABLE DATE |
|---|---|---|---|---|
| 0001 | Clever Clinic | West Palm Beach, Florida 33401 | 2018/03/16 | 2018/03/19 |
| 0002 | Tokyo Seiwa Hospital | Minato-ku,Tokyo,105-8423 | 2018/03/21 | 2018/03/22 |
| 0003 | Sharité | Shariteplatz 1 10117 Berlin | 2018/03/25 | 2018/03/28 |
| ... | ... | ... | ... | ... |

501

EXAMINATION INSTITUTION ID

| | EXAMINATION INSTITUTION | EXAMINATION SITE | FIRST EXAMINABLE DATE | SECOND EXAMINABLE DATE |
|---|---|---|---|---|
| 0001 | LA Medical Cent | Westwood Plaza, LA, CA 90095 | 2018/03/12 | 2018/03/18 |
| 0002 | Keio General Hospital | Shinjuku-ku, Tokyo 106-0016 | 2018/03/18 | 2018/03/24 |
| 0003 | München Klinik | Sanatoriumsplatz 2, 81545 München | 2018/03/27 | 2018/03/28 |
| ... | ... | ... | ... | ... |

| MANUFACTURER ID | MANUFACTURER |
|---|---|
| 0001 | LA Manufacturer |
| 0002 | Tokyo Manufacturer |
| 0003 | München Manufacturer |
| ... | ... |

503

| PRODUCTION DEVICE ID | MANUFACTURER ID | PRODUCIBLE PERIOD (6 MONTHS) |
|---|---|---|
| 0001 | 0001 | 2018/03/16~2018/09/16 |
| 0002 | 0001 | 2018/04/02~2018/10/02 |
| 0003 | 0001 | 2018/07/08~2019/01/08 |
| 0004 | 0002 | 2018/03/21~2018/09/21 |
| 0005 | 0002 | 2018/03/22~2018/09/22 |
| 0006 | 0002 | 2018/04/02~2018/10/02 |
| 0007 | 0003 | 2018/05/16~2018/11/16 |
| 0008 | 0003 | 2018/05/28~2018/11/28 |
| 0009 | 0003 | 2018/06/01~2018/12/01 |
| ... | ... | ... |

504 → REARRANGE THE SCHEDULE.

{ PRODUCTION OF THE STEM CELLS CANNOT BE STARTED FROM THE ACCEPTANCE DATE OF SOMATIC CELLS.

| CRYOPRESERVATION DEVICE ID | MANUFACTURER ID | CRYOPRESERVABLE PERIOD (30 DAYS) |
|---|---|---|
| 0001 | 0001 | 2018/05/03~2018/06/01 |
| 0002 | 0001 | 2018/06/02~2018/07/01 |
| 0003 | 0001 | 2018/06/18~2018/07/17 |
| 0004 | 0002 | 2018/05/13~2018/06/11 |
| 0005 | 0002 | 2018/05/22~2018/06/20 |
| 0006 | 0002 | 2018/07/16~2018/08/14 |
| 0007 | 0003 | 2018/05/16~2018/11/16 |
| 0008 | 0003 | 2018/05/28~2018/11/28 |
| 0009 | 0003 | 2018/06/01~2018/12/01 |
| ... | ... | ... |

505 → REARRANGE THE SCHEDULE.

{ CRYOPRESERVATION IS NOT POSSIBLE AT THE PREDICTED RELEASE DATE AND TIME.

| ENTRY ID | ENTRY DATE | DONOR ID | FIRST DESIRED COLLECTION DATE | SECOND DESIRED COLLECTION DATE | THIRD DESIRED COLLECTION DATE |
|---|---|---|---|---|---|
| 0001 | 2018/02/19 | 0102 | 2018/03/15 | 2018/03/16 | 2018/03/17 |
| 0002 | 2018/02/23 | 0023 | 2018/03/18 | 2018/03/19 | 2018/03/22 |
| 0003 | 2018/02/25 | 0085 | 2018/03/21 | 2018/03/22 | 2018/03/25 |
| ... | ... | ... | ... | ... | ... |

DOES ANY OF THESE FALL UPON ONE OF THE COLLECTABLE DATES OF THE COLLECTING SITE MOST CLOSELY LOCATED TO DONOR'S ADDRESS?

SUBTRACT 7 DAYS FOR TRANSPORT.

ADD 2 DAYS FOR TRANSPORT.

506

| COLLECTING INSTITUTION ID | COLLECTION DATE OF SOMATIC CELL | TRANSPORT DATE OF COLLECTING KIT | EXAMINATION INSTITUTION ID | DATE OF SOMATIC CELL EXAMINATION |
|---|---|---|---|---|
| 0001 | 2018/03/16 | 2018/03/09 | 0001 | 2018/03/18 |
| 0002 | 2018/03/22 | 2018/03/15 | 0002 | 2018/03/24 |
| 0003 | 2018/03/25 | 2018/03/14 | 0003 | 2018/03/27 |
| ... | ... | ... | ... | ... |

ADD 7 DAYS FOR EXAMINATION AND 2 DAYS FOR TRANSPORT TO OBTAIN AN ACCEPTANCE DATE OF SOMATIC CELLS. DOES IT FALL WITHIN ONE OF PRODUCIBLE PERIODS OF THE MOST CLOSELY LOCATED MANUFACTURER?

507

| ACCEPTANCE ID | ENTRY ID | MANUFACTURER ID | ACCEPTANCE DATE OF SOMATIC CELLS |
|---|---|---|---|
| 0001 | 0001 | 0001 | 2018/03/27 |
| 0002 | 0002 | 0002 | 2018/04/02 |
| 0003 | 0003 | 0003 | 2018/04/05 |
| ... | ... | ... | ... |

FIG. 26

| TRANSPORT ID | TRANSPORT CONTAINER ID | CLIENT ID | ACCEPTANCE ID |
|---|---|---|---|
| 0001 | 0001 | 0001 | 0001 |
| 0001 | 0002 | 0002 | 0001 |
| 0001 | 0002 | 0003 | 0001 |
| 0002 | 0003 | 0004 | 0002 |
| ... | ... | ... | ... |

512

| TEMPERATURE (°C) | ABNORMALITY | ACCUMULATED TRANSPORTATION TIME (HOURS:MINUTES) | ABNORMALITY | COAGULATION VALUE (IMPEDANCE Ω) | ABNORMALITY | VIBRATION VALUE (ACCELERATION m/sec²) | ABNORMALITY |
|---|---|---|---|---|---|---|---|
| 21:05,4,3; 21:06,6,2; | Yes | 15:24 | No | 132 | No | 21:05,X+15,Y−12,Z+3; 21:06,X+2,Y−8,Z+12; | No |
| 21:05,3,8; 21:06,3,9; | No | 15:24 | No | 155 | No | 21:05,X+28,Y−45,Z+8; 21:06,X+96,Y+28,Z+1; | Yes |
| 21:05,3,8; 21:06,3,9; | No | 15:24 | No | 128 | No | 21:05,X+28,Y−45,Z+8; 21:06,X+96,Y+28,Z+1; | Yes |
| 02:16,3,6; 02:17,3,7; | No | 52:41 | Yes | 386 | Yes | 10:28,X−5,Y+10,Z−11; 10:29,X−2,Y+8,Z−12; | No |
| ... | ... | ... | ... | ... | ... | ... | ... |

STEM CELL MANUFACTURING SYSTEM, STEM CELL INFORMATION MANAGEMENT SYSTEM, CELL TRANSPORT APPARATUS, AND STEM CELL FROZEN STORAGE APPARATUS

1. Field of the Invention

The present invention relates to a manufacturing technique of pluripotent stem cells, and in particular to a stem cell manufacturing system, a stem cell information management system, a cell transport apparatus, and a stem cell frozen storage apparatus.

2. Description of the Related Art

Embryonic stem cells (ES cells) are stem cells established from early-stage embryos of humans or mice, and they are pluripotent, or able to differentiate into any cells present in a living body. Human ES cells are considered potentially useful for cell transplantation in the treatment of many diseases such as Parkinson's disease, juvenile diabetes, and leukemia. ES cell transplant, however, has a drawback of causing a rejection, just like organ transplants. Besides, use of ES cells is controversial from an ethical point of view because they are established by destroying human embryos.

Professor Shinya Yamanaka of Kyoto University succeeded in establishing induced pluripotent stem cells (iPS cells) by introducing four genes, Oct3/4, Klf4, c-Myc, and Sox2 into somatic cells, and he was awarded a 2012 Nobel Prize in Physiology or Medicine (see, for example, Japanese Examined Patent Publication (Kokoku) No. 4183742). Being ideal pluripotent cells that do not cause rejection nor involve ethical issues, iPS cells are received with high expectations for use in cell transplant.

SUMMARY OF INVENTION

Induced stem cells like iPS cells are established by introducing inducing factors such as genes into cells, and then expanded and cryopreserved. However, there are problems as described below in producing iPS cells for clinical application (GLP, GMP grades) on an industrial scale.

1) Expenses iPS cells for clinical application are produced and cryopreserved preferably in a clean room that is kept very clean. However, clean rooms are very expensive to maintain. Using clean rooms efficiently to reduce costs is a task to be addressed in achieving industrial use of iPS cells.

2) Quality

The processes from establishing stem cells to cryopreserving them involve a series of complicated work carried out by hand. Besides, production of stem cells depends much on individual skills. Accordingly, qualities of iPS cells can vary depending on the individuals engaged in the production of cells. Qualities also vary day by day during the cell production. The qualities of iPS cells also depend on the qualities of the somatic cells from which they are derived. It is therefore important to properly manage the time and the temperature for transportation of somatic cells until they are received, to properly manage characteristics of somatic cell donors (sex, age, anamnesis, genetic background, and the like), and to properly manage combinations of these various different pieces of information.

3) Time

To avoid cross contamination of somatic cells or iPS cells among different individuals, iPS cells are produced in a clean room for only one individual at one time. In addition, it takes a long time to establish iPS cells and to evaluate the quality of established cells. It would take many years to produce iPS cells for many individuals in want of iPS cells by producing iPS cells for each of the individuals in one room. Thus a system capable of concurrently producing iPS cells for a plurality of individuals in want of iPS cells is desired. Furthermore, since cultured cells are living, they will die unless delivered, processed and frozen at appropriate timings. Especially in a concurrent production of iPS cells, unless integrated management is in place to control all the schedules including collecting somatic cells, establishing iPS cells, and cryopreserving them, it is not possible to timely provide iPS cells for many individuals in want of them.

4) Contamination

The first and foremost pollutants in clean rooms are humans, and their removal from the rooms is the first priority. In addition, even if iPS cells for a plurality of individuals in want are successfully produced on a large scale and concurrently, contamination remains difficult to prevent unless all the processes, including collecting somatic cells, establishing stem cells, and cryopreserving them, are arranged to be completed in a closed system. Besides, concurrent manufacturing of cells will increase the risk of erroneous identification of manufacturing samples and cross contamination.

5) Human Resources

As described above, much of the work for producing iPS cells is carried out by hand, and only a few experts can produce iPS cells for clinical application. The problem is that the processes from establishing stem cells to cryopreserving them involve a series of complicated work. Culturing cells for clinical application involves three steps, i.e., checking the standard operation procedure (SOP), operation according to the SOP, and checking whether the operation has been conducted in accordance with the SOP. It is very inefficient for humans to execute these steps. Human execution of these steps may lead to erroneous identification of somatic cells of a plurality of individuals in want of iPS cells, erroneous identification of culture reagents or materials for producing iPS cells, or human errors including procedural errors. Furthermore, since cell culture involves management for 24 hours every day and stem cells are cryopreserved for decades, there is a limit on what human efforts can do to achieve adequate management.

Therefore, there is a desire for a technique for producing and cryopreserving stem cells in a timely manner while preventing contamination, based on an inexpensive but sophisticated quality management.

According to an aspect of the present disclosure, provided is a stem cell manufacturing system for manufacturing stem cells from somatic cells, the system including: one or more closed production device(s) configured to produce stem cells from somatic cells; one or more drive device(s) configured to be connected with the production device(s) and drive the production device(s) in such a manner as to maintain the production device(s) in an environment suitable for producing stem cells; one or more cryopreservation device(s) configured to cryopreserve the produced stem cells; a first memory device configured to store whether or not somatic cells have been introduced to the production device(s), as a first state; a second memory device configured to store whether or not the production device(s) is/are connected with the drive device(s), as a second state; and a third memory device configured to store whether or not the produced stem cells can be placed in the cryopreservation device(s), as a third state.

According to another aspect of the present disclosure, provided is a stem cell information management system for performing an integrated management of information in an entry process of making an entry of a manufacturing request for manufacturing stem cells from somatic cells, a transport process of transporting somatic cells collected from a somatic cell donor or stem cells produced from the somatic cells, an examination process of examining the somatic cells or the stem cells, a manufacturing process of manufacturing the stem cells from the somatic cells, and a stock process of stocking the stem cells, the system including: a memory unit configured to store a collection schedule for collecting the somatic cells from the somatic cell donor, an examination schedule for examining the somatic cells, a production schedule for one or more production device(s) configured to produce the stem cells from the somatic cells, a cryopreservation schedule for one or more cryopreservation device(s) configured to cryopreserve the produced stem cells, and a stock schedule for a stock site at which the cryopreservation device(s) is/are stocked; and a determination unit configured to determine at least a collection date for collecting the somatic cells from the somatic cell donor, based on the stored collection schedule, the examination schedule the production schedule, the cryopreservation schedule, and the stock schedule.

According to still another aspect of the present disclosure, provided is a cell transport apparatus for transporting somatic cells collected from a somatic cell donor(s) to one or more closed production device(s) configured to produce stem cells from somatic cells, or for transporting the stem cells to a stem cell stock site, the apparatus including: a somatic cell collection vial for containing the collected somatic cells and equipped with a first individual identification device containing donor identification information for identifying the somatic cell donor and production device identification information for identifying the production device, or a stem cell freezing vial for containing stem cells produced in the production device and subsequently frozen and equipped with a second individual identification device containing the donor identification information, the production device identification information, and stock site identification information for identifying a stock site for stocking the stem cells; a transport container configured to contain one or more of the somatic cell collection vials or one or more of the stem cell freezing vials; a reader device configured to read at least one of the donor identification information, the production device identification information, and the stock site identification information contained in the first individual identification device or the second individual identification device; and a transport means for transporting the transport container containing the somatic cell collection vial or the stem cell freezing vial, based on the read production device identification information or stock site identification information.

According to still another aspect of the present disclosure, provided is a stem cell frozen storage apparatus for cryopreserving stem cells produced from somatic cells collected from a somatic cell donor, the apparatus including: a stem cell freezing vial(s) released from one or more closed production device(s) and containing frozen stem cells; one or more cryopreservation device(s) configured to cryopreserve the stem cell freezing vial(s); a storehouse that stores the cryopreservation device(s); and a first conveyer device configured to convey the cryopreservation device(s) into and out of the storehouse, the cryopreservation device(s) including: a container unit configured to contain one or more of the stem cell freezing vials, and a refrigerant chamber configured to contain a refrigerant for freezing the stem cell freezing vial(s).

According to yet another aspect of the present disclosure, provided is a stem cell information management system including: a terminal apparatus that receives a request for manufacturing stem cells; and a server apparatus that manages a step of accepting somatic cells for producing the stem cells, a step of manufacturing stem cells, a step of stocking the produced stem cells, and a step of transporting the produced stem cells; wherein the terminal apparatus includes: an entry unit that makes an entry of the manufacturing request, including a desired collection date of the somatic cells, as well as donor identification information for identifying the somatic cell donor; and a terminal sending unit that sends the entered manufacturing request and the entered donor identification information to the server apparatus; and wherein the server apparatus includes: a memory unit that stores a collectable date on which the somatic cells can be collected, producible period during which the stem cells can be produced, and a stockable location and a stockable period where the produced stem cells can be stocked; a receiving unit that receives the sent manufacturing request and the sent donor identification information; a determination unit that: determines a collection date of the somatic cells based on the desired collection date included in the entered manufacturing request and the stored collectable date, determines a production period of the stem cells based on the determined collection date of the somatic cells and the stored producible period, determines an acceptance date of the somatic cells based on the determined collection date of the somatic cells and the stored producible period, determines a stock location and a stock period for stocking the produced stem cells, based on the determined production period and the stored stockable location and stockable period, and determines a shipping date of the produced stem cells based on the determined production period and the stored stockable location and stockable period; a memory processing unit that stores, in the memory unit, the determined collection date of the somatic cells, the determined production period, the determined acceptance date of the somatic cells, the determined stock location and stock period, and the determined shipping date of the stem cells in association with the received donor identification information; and a server sending unit that sends the collection date of the somatic cells, the production period, the acceptance date of somatic cells, the stock location and stock period, and the shipping date of stem cells, stored in association with the donor identification information, to the somatic cell donor represented by the stored donor identification information.

According to yet still another aspect of the present disclosure, provided is a stem cell information management system including: an entry management terminal that receives a request for manufacturing stem cells; an acceptance management terminal that manages an acceptance of somatic cells for producing the stem cells; a manufacturing process management terminal that manages a step of manufacturing the stem cells; and a stock management terminal that manages a stock of the produced stem cells; wherein the entry management terminal includes: a first memory unit; an entry unit that makes an entry of the manufacturing request including a desired collection date for collecting the somatic cells, as well as donor identification information for identifying the somatic cell donor; a first determination unit that determines a collection date of the somatic cells based on the desired collection date included in the entered manufacturing request; a first output unit that outputs the determined collection date of the somatic cells to a first medium; and a first memory processing unit that stores, in the first memory unit, the determined collection date of the somatic cells in association with the entered donor identification information; wherein the acceptance management terminal includes: a second memory unit that stores a collectable date on which the somatic cells can be collected; a second output unit that outputs the stored collectable dates to a second medium; a second determination unit that determines an acceptance date of the somatic cells based on the collection date of the somatic cells communicated by the first medium; and a second memory processing unit that stores the determined acceptance date of somatic cells in the second memory unit; wherein the manufacturing process management terminal includes: a third memory unit that stores producible periods during which the stem cells can be produced; a third determination unit that determines a production period of the stem cells based on the collection date of the somatic cells, communicated by the first medium and the stored producible period, and that determines a shipping date of the produced stem cells based on the determined production period of the stem cells; a third output unit that outputs the stored producible periods of stem cells to a third medium and outputs the determined production period of the stem cells to a fourth medium; and a third memory processing unit that stores, in the third memory unit, the determined production period of the stem cells and the determined shipping date of the stem cells; wherein the stock management terminal includes: a fourth memory unit that stores a stockable location and a stockable period where the produced stem cells can be stocked; a fourth output unit that outputs the stored stockable location and stockable period to a fifth medium; and a fourth determination unit that determines a stock location and a stock period for stocking the produced stem cells, based on the production period of the stem cells communicated by the fourth medium and the stored stockable location and stockable period; and wherein the first determination unit determines the collection date of the somatic cells based on the desired collection date and the collectable date communicated by the second medium, wherein the second determination unit determines the acceptance date of the somatic cells based on the collection date of the somatic cells and the production period communicated by the third medium, and the third determination unit determines the shipping date of the stem cells based on the production period of the stem cells and the stockable location and stockable period communicated by the fifth medium.

BRIEF DESCRIPTION OF THE DRAWINGS

FIG. 19 illustrates a donors master, a collecting institutions master, and an examination institutions master of the stem cell information management system according to an embodiment.

FIG. 20 illustrates a manufactures master, a production devices master, and a cryopreservation devices master of the stem cell information management system according to an embodiment.

FIG. 21 illustrates an entry table and an acceptance table of the stem cell information management system according to an embodiment.

FIG. 26 illustrates a transport table of the stem cell information management system according to an embodiment.

DETAILED DESCRIPTION

Embodiments of the present disclosure will be described in detail below with reference to the attached drawings. Throughout the drawings, identical or similar parts are denoted by identical or similar numerals. The embodiments described below are not intended to limit in any way the technical scope of the invention described in the appended claims or the meaning of words used therein.

1. Stem Cell Manufacturing System

Figure 1:
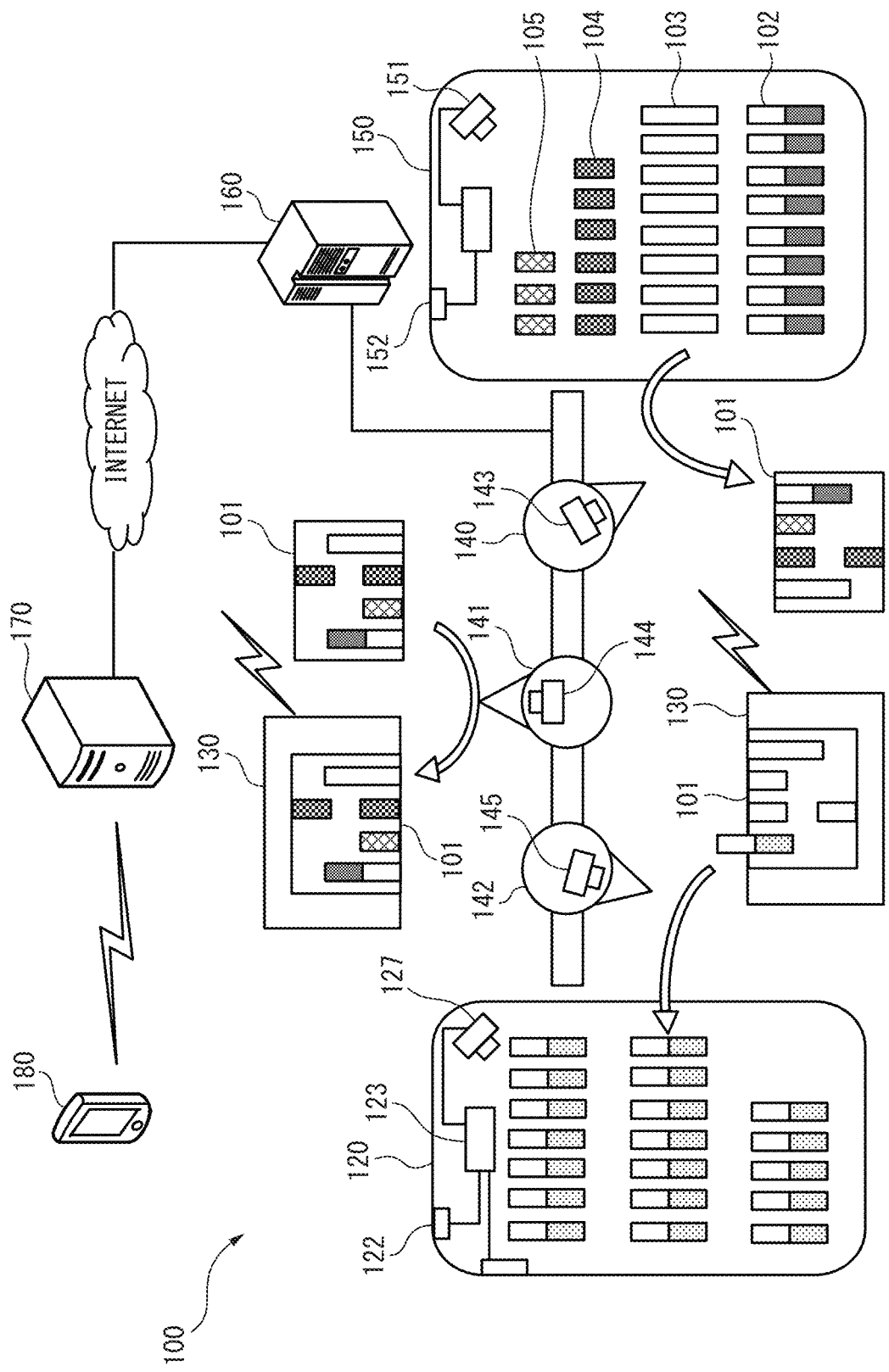
FIG. 1 illustrates a schematic configuration of a stem cell manufacturing system according to an embodiment.

FIG. 1 to FIG. 6 illustrate configurations of a stem cell manufacturing system 100 according to the present embodiment. As illustrated in FIG. 1, the stem cell manufacturing system 100 includes one or more closed production devices 101 configured to produce stem cells from somatic cells, and the system can produce stem cells for a plurality of individuals in want of stem cells. A sealed vial 102 containing somatic cells is inserted to a closed production device 101, and the production device automatically produces stem cells and releases a sealed vial 103 containing frozen stem cells. Released vials 103 are transported to one or more cryopreservation devices 120 in a timely manner and cryopreserved. Although a system in which iPS cells are produced from blood cells will be described according to the present embodiment, it should be understood that the invention can be applied to a system in which iPS cells are produced from skin-derived cells, a system in which somatic stem cells are produced from other somatic cells, a system in which stem cells are produced from animal cells, and other systems.

As illustrated in FIG. 1, the stem cell manufacturing system 100 includes a drive device 130 configured to drive a closed production device 101 in such a manner as to maintain the production device in an environment suitable for producing stem cells. The stem cell manufacturing system 100 further includes a conveyer device 140 configured to convey at least one of a plurality of kinds of vials 102 to 105 preserved in a preservation device 150 to the production device 101, a conveyer device 141 configured to convey the production device 101 to the drive device 130 or conveys the drive device 130 to the production device 101, and a conveyer device 142 configured to convey a stem cell freezing vial 103 released from the production device 101 to a cryopreservation device 120. These conveyer devices 140 to 142 are robots autonomously performing work according to a teaching program, but according to another embodiment these conveyer devices 140 to 142 may be a belt conveyer system. According to still another embodiment, two or three of the conveyer devices 140 to 142 are formed in a unitary body.

Referring to FIG. 1, the stem cell manufacturing system 100 includes a control device 160 connected with the drive device 130, the conveyer devices 140 to 142, and the cryopreservation device 120 by wired or wireless communication and controlling the drive device 130, the conveyer devices 140 to 142, and the cryopreservation device 120. The control device 160 is also connected with a superordinate computer 170 on a cloud by wired or wireless communication and has access to various pieces of information acquired in all the processes except the manufacturing process, i.e., in the entry process, the transport process, the examination process, and the stock process. The superordinate computer 170 includes at least an entry memory device (see FIG. 15, numeral 202) configured to store information on the somatic cell donor upon receiving a request for manufacturing stem cells. The superordinate computer 170 transmits various pieces of information such as an abnormality alarm to a mobile terminal 180 in a remote location. The mobile terminal 180 may be, for example, a smart phone of the somatic cell donor.

Figure 2:
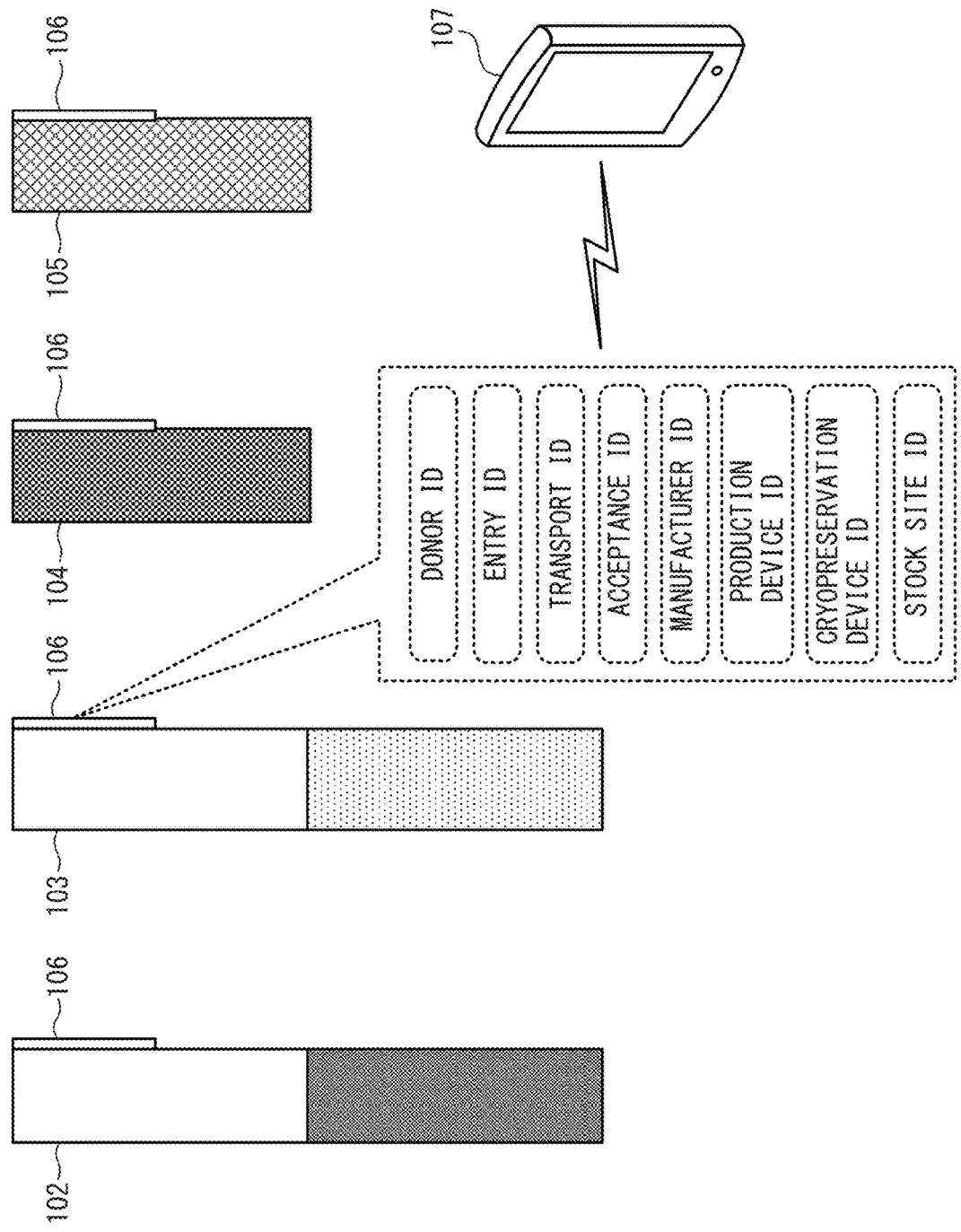
FIG. 2 is a side view of a somatic cell collection vial, a stem cell freezing vial, a culture reagent vial, and a stem cell production material vial according to an embodiment.

As illustrated in FIG. 2, the vials include a somatic cell collection vial 102 containing collected somatic cells, a stem cell freezing vial 103 containing frozen stem cells, a culture reagent vial 104 containing a culture reagent, and a stem cell production material vial 105 containing a material other than the culture reagent used for producing stem cells. Although only four kinds of vials 102 to 104 are illustrated in FIG. 2 to facilitate understanding, a plurality of kinds of vials actually exist. These vials 102 to 104 are equipped with an individual identification device 106 for identifying individuals. The individual identification device 106 may be a semi-conductor chip using RFID or the like, one-dimension code such as the barcode, or a two-dimensional code such as QR Code (registered trademark) or SP Code.

The individual identification device 106 as illustrated in FIG. 2 at least includes a donor ID identifying a somatic cell donor. The conveyer devices 140 to 142, the drive device 130, and the cryopreservation device 120 illustrated in FIG. 1 are equipped with a reader device 107 (see FIG. 2) configured to read the information from the individual identification device 106 and are capable of reading the donor information from the superordinate computer 170, based on the donor ID read from the vial. Donor information includes, for example, informed consent, nationality, address, sex, age, blood type, anamnesis, prescription history, health check results, and the family members from whom stem cells were produced in the past, of the somatic cell donor. According to another embodiment, the individual identification device 106 may contain such donor information, and in that case, the donor information is encrypted.

In addition to the donor ID, the individual identification device 106 illustrated in FIG. 2 includes at least one of an entry ID for identifying a taking of a request for manufacturing stem cells, a transport ID for identifying a transport of vials, an acceptance ID for identifying an acceptance of vials, a manufacturer ID for identifying a stem cell manufacturer, a production device ID for identifying a production device, a cryopreservation device ID for identifying a cryopreservation device, and a stock site ID for identifying a stock site in which the cryopreservation device is to be stocked. This ensures traceability in case of abnormality in each of the processes from receiving a request for manufacturing stem cells to stocking stem cells. Based on the production device ID read from the vial, the conveyer device 140 illustrated in FIG. 1 identifies the production device 101 to which the somatic cell collection vial 102 will be conveyed. Similarly, based on the drive device ID read from the vial, the conveyer device 141 conveys the production device 101 to the drive device 130 or conveys the drive device 130 to the production device 101. Further, based on the cryopreservation device ID read from the vial, the conveyer device 142 conveys the stem cell freezing vial 103 to the cryopreservation device 120.

As illustrated in FIG. 1, the conveyer device 140 further includes a vision sensor 143 for acquiring data to be used for inputting whether or not the somatic cell collection vial 102 has been introduced to the production device 101 (a first state), and transmits the acquired information indicating the first state to the control device 160. The conveyer device 141 includes a vision sensor 144 for acquiring data to be used for inputting whether or not the production device 101 is connected with the drive device 130 (a second state), and transmits the acquired information indicating the second state to the control device 160. The conveyer device 142 includes a vision sensor 145 for acquiring data to be used for inputting whether or not the stem cell freezing vial 103 may be placed in the cryopreservation device 120 (a third state), and transmits the acquired data indicating the third state to the control device 160.

Figure 3A:
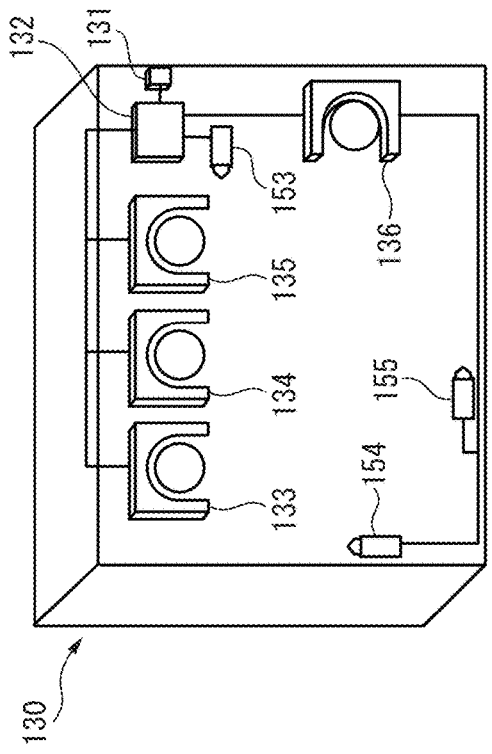
FIG. 3A is a cross sectional view of a production device according to an embodiment.
Figure 3B:
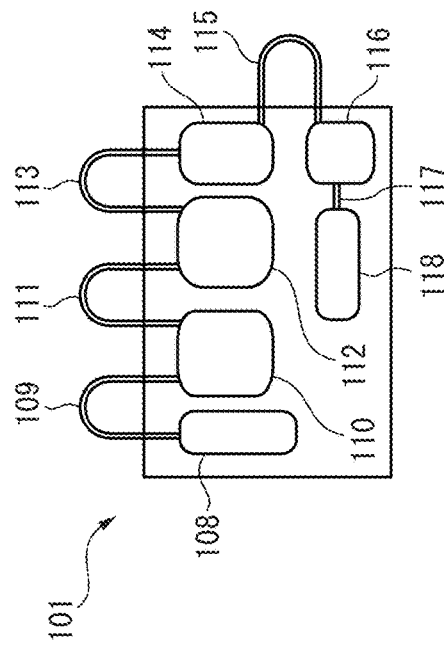
FIG. 3B is a cross sectional view of a drive device.
Figure 3C:
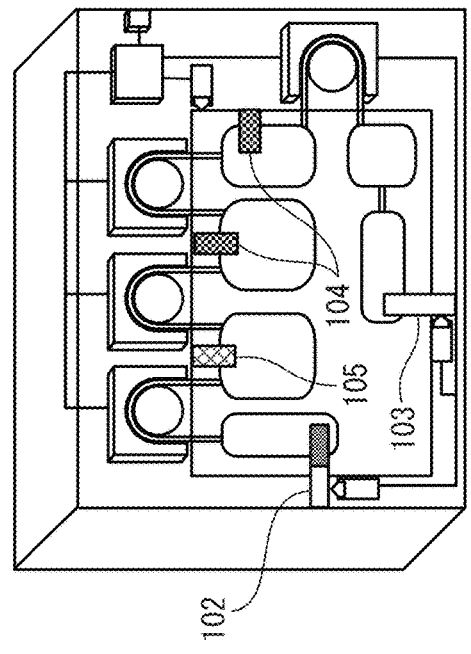
FIG. 3C is a cross sectional view of the production device connected with the drive device.
Figure 4:
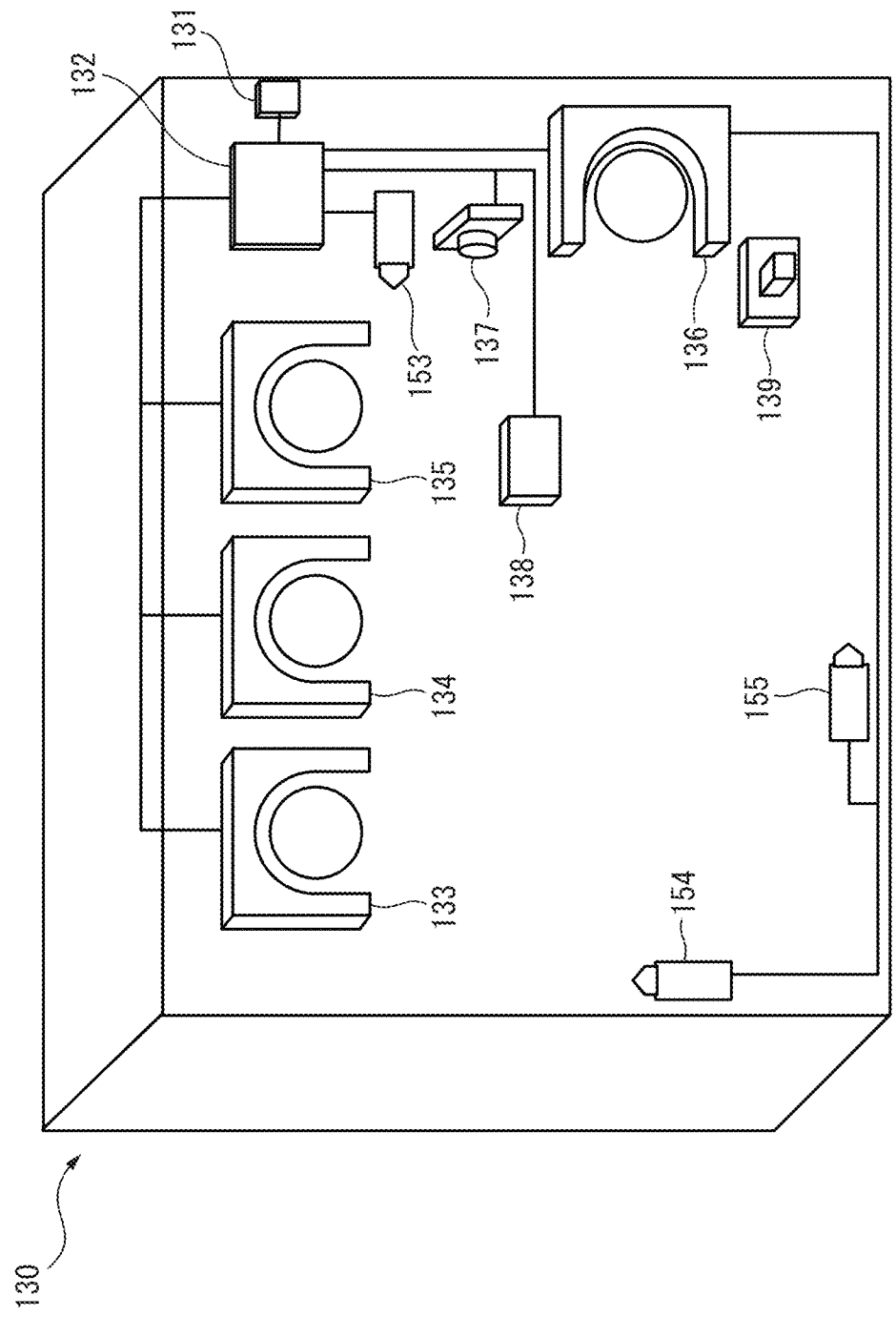
FIG. 4 is an enlarged cross sectional view of the drive device according to an embodiment.
Figure 5:
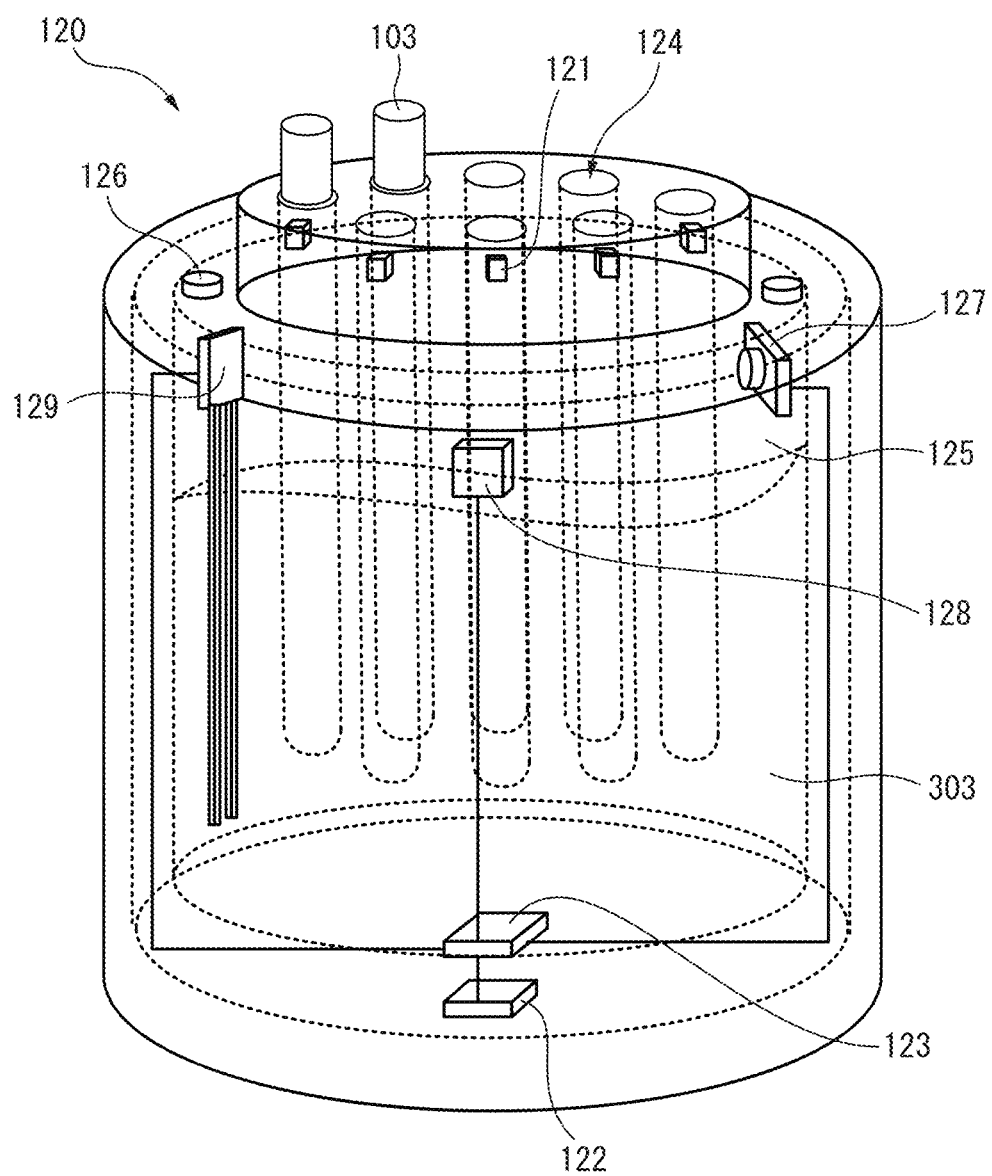
FIG. 5 is a perspective view of the cryopreservation device according to an embodiment.

According to another embodiment, as illustrated in FIG. 3B and FIG. 4, the drive device 130 may include switches 153 to 155 for outputting electrical signals for inputting at least one of the first to the third states, and transmit a signal indicating at least one of the first to the third states to the control device 160. According to still another embodiment, as illustrated in FIG. 5, the cryopreservation device 120 may include a presence sensor 121 for detecting a presence of a stem cell freezing vial 103 for inputting the third state, and transmit information indicating the third state to the control device 160. According to yet another embodiment, an input device (not illustrated) configured to manually input at least one of the first to the third states may be included. The input device may be a liquid crystal touch panel, a keyboard, or a mouse provided for the control device 160, a manufacturing process management terminal (see FIG. 15 and FIG. 16), or the like.

Figure 6:
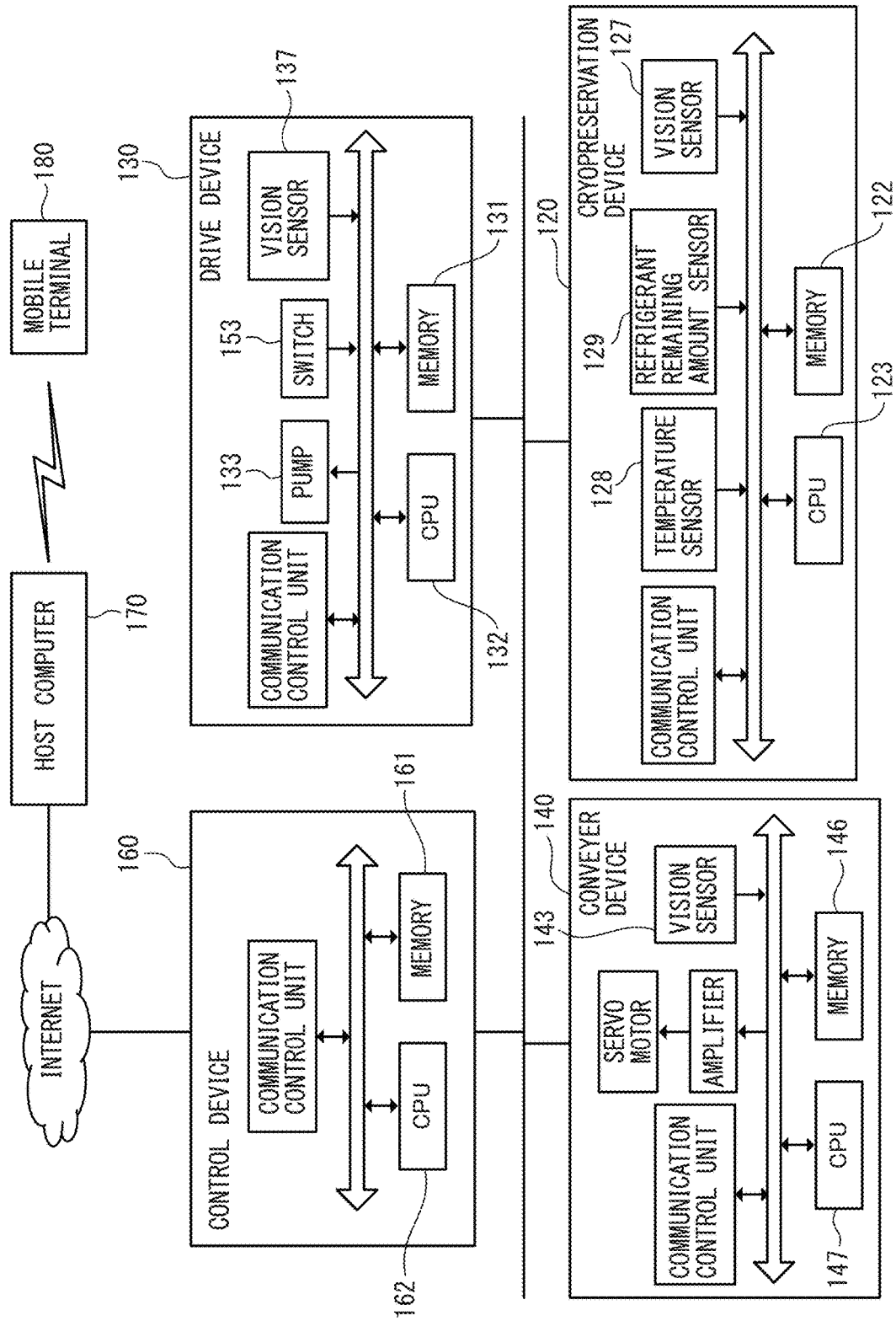
FIG. 6 is a block diagram of the stem cell manufacturing system according to an embodiment.

As illustrated in FIG. 6, the conveyer devices 140 to 142 (which are represented solely by the conveyer device 140 in FIG. 6) each include a CPU 147 that causes a memory 146 to store information indicating at least one of the above-described first to the third states. In another embodiment, the drive device 130 may include the CPU 132 that causes a memory 131 to store information indicating at least one of the above-described first to the third states. According to yet another embodiment, the cryopreservation device 120 may include a CPU 123 to cause a memory 122 to store information indicating the above-described third state.

Figure 8:
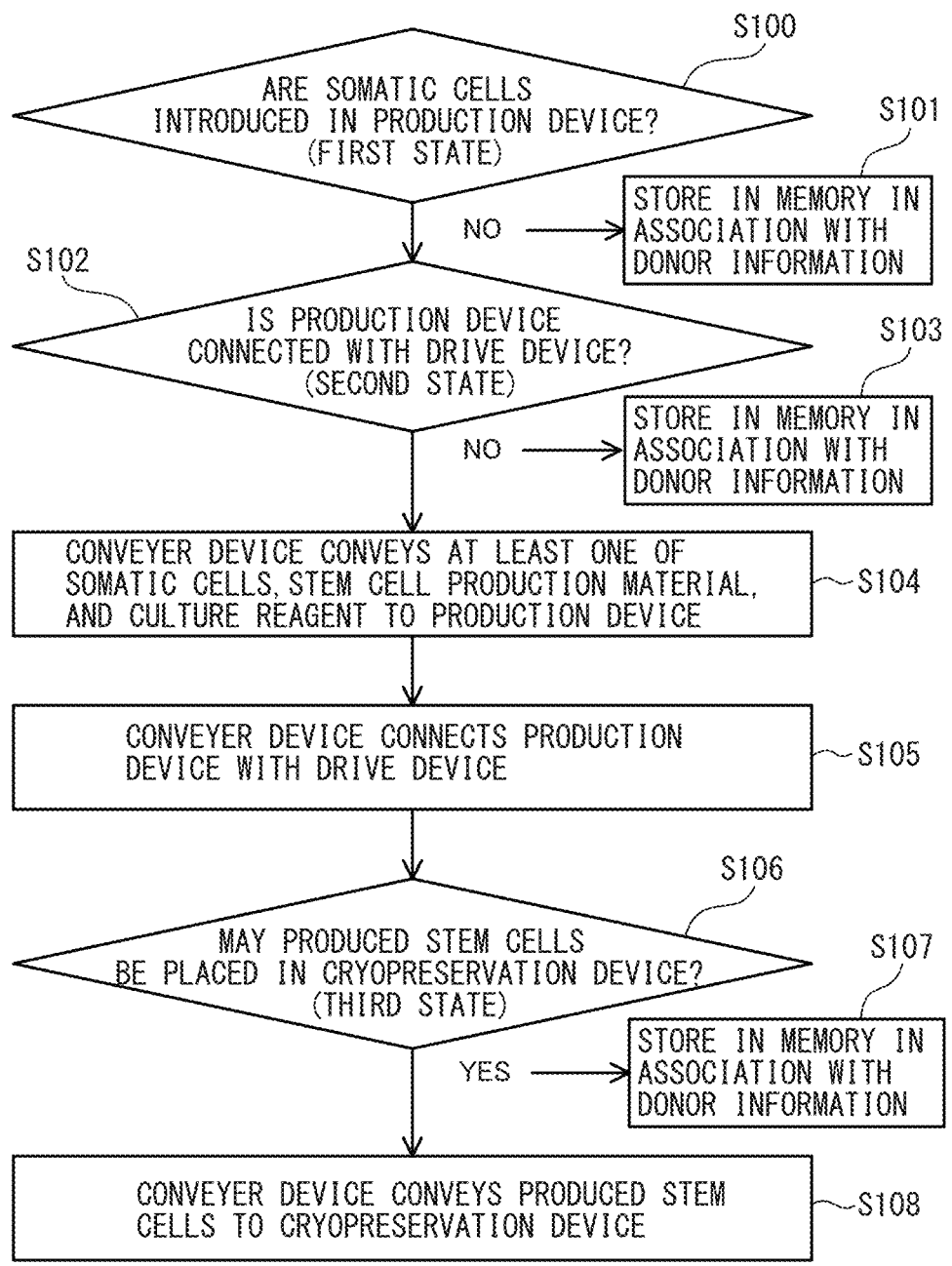
FIG. 8 is a flow chart illustrating an operation of the stem cell manufacturing system according to an embodiment, based on a first state to a third state.

FIG. 8 is a flow chart illustrating an operation based on the first state to the third state in the stem cell manufacturing system 100 according to the present embodiment. When the conveyer device 140 has determined by using the vision sensor 143 that the somatic cell collection vial 102 has not been introduced in the production device 101 (step S100), the conveyer device 140 stores information indicating the first state in the memory 146, in association with the donor ID read from the vial (step S101). When the conveyer device 141 has determined by using the vision sensor 144 that the production device 101 is not connected with the drive device 130 (step S102), the conveyer device 141 stores information indicating the second state in the memory 147, in association with the donor ID read from the vial (step S103). The conveyer device 140 then conveys at least one of the somatic cell collection vial 102, the stem cell freezing vial 103, the culture reagent vial 104, and the stem cell production material vial 105 to the production device 101 (step S104), and the conveyer device 141 connects the production device 101 with the drive device 130 (step S105). Subsequently, when the conveyer device 142 has determined by using the vision sensor 145 that stem cell freezing vial 103 has been released from the production device 101 and that the stem cell freezing vial 103 may be placed in the cryopreservation device 120 (step S106), the conveyer device 142 stores information indicating the third state in a memory 148, in association with the donor ID read from the vial (step S107). The conveyer device 142 then conveys the stem cell freezing vial 103 to the cryopreservation device 120 (step S108).

As illustrated in FIG. 3A, the production device 101 includes an isolation device 108 that receives the somatic cell collection vial 102 and isolates cells from the blood, and the drive device 130 includes a pump 133 that transfers suspension containing isolated mononuclear cells in a pre-introduction cell transfer fluid path 109. The production device 101 further includes a factor introducing device 110 including an electroporator, that introduces pluripotency-inducing factors into the isolated mononuclear cells to produce inducing-factor-introduced cells, and the drive device 130 includes a pump 134 for transferring solution containing inducing-factor-introduced cells through a factor-introduced cell transfer fluid path 111. The production device 101 also includes an initial culture device 112 for culturing the inducing-factor-introduced cells, and the drive device 130 includes a pump 135 for transferring fluid containing the cultured stem cell clusters and a trypsin-substituting recombinant enzyme in a first cell cluster transfer fluid path 113. The production device 101 further includes an expansion culture device 114 that receives a solution containing stem cell clusters separated by sieving in a mesh or the like in the first cell cluster transfer fluid path 113 and places the solution in wells to repeat expansion culture, and the drive device 130 includes a pump 136 for transferring fluid containing expansively cultured stem cell clusters through the second cell cluster transfer fluid path 115. The production device 101 further includes a cell cluster transfer mechanism 117 that receives a solution containing stem cell clusters separated by sieving in a mesh or the like in the second cell cluster transfer fluid path 115 and transfers in order the separated cell clusters to a pre-package cell fluid path 116, and a packaging device 118 that places in order portions of solution containing stem cell clusters, transferred through the pre-package cell fluid path, into a stem cell freezing vial 103, and freezes the solution instantaneously by using liquid nitrogen or the like.

As illustrated in FIG. 4, the drive device 130 further includes a vision sensor 137 configured to acquire data in the production device 101 and, based on the data from the vision sensor 137, stores whether or not the stem cells are being produced in a normal condition as a fourth state in numerical form in the memory 131. Such a fourth state may include the size or growth speed of stem cell clusters in the initial culture device 112 and the expansion culture device 114, the ratio between stem cell clusters of different sizes, color tone or pH of culture reagent, and the like.

The drive device 130 further includes a temperature sensor 138 configured to detect temperature in the production device 101 and, based on the temperature from the temperature sensor 138, stores whether stem cells are being produced in a normal condition as a fourth state in numerical form in the memory 131. Such a fourth state may include a resistance, voltage, and the like of the temperature sensor in the initial culture device 112 or the expansion culture device 114.

According to another embodiment, the drive device 130 may include an examination window (not illustrated) for conducting an visual examination into the production device 101 and, based on the visual examination through the examination window done by the operator, whether or not stem cells are being produced in a normal condition may manually inputted to be stored in the memory 131 as a fourth state in numerical form. Such a fourth state may include the size or growth speed of stem cell clusters in the initial culture device 112 and the expansion culture device 114, the ratio between stem cell clusters of different sizes, color tone of culture reagent.

According to the present embodiment, the drive device 130 further includes a removal outlet 139 for taking out a sample released from the production device 101 and, based on the sample taken out, stores whether the stem cells are being produced in a normal condition as a fourth state in numerical form in a memory. Such a fourth state may be, for example, the number of stem cells, the size of stem cells, the ratio between stem cell clusters of different sizes, the shape of stem cells, the presence or absence of differentiated cells having differentiated from the stem cells, or the like, which is measured by using a flow cytometer, a cell sorter, or the like.

According to another embodiment, the drive device 130 further includes a display device (not illustrated) configured to display data in the production device 101 and, based on a visual examination of displayed data, whether or not the stem cells are in a normal condition may be manually inputted to be stored in the memory 131 as a fourth state in numerical form. Such a fourth state may be, for example, the size or growth speed of stem cell clusters, the ratio between stem cell clusters of different sizes, the stem cell count, the shape of stem cells, the color tone of culture reagent, or the like. According to still another embodiment, such a display device is not the drive device 130 but may be a liquid crystal monitor provided for the control device 160, a manufacturing process management terminal (see FIG. 15 and FIG. 16), or the like. The drive device 130 also stores at least one of the normal range and the abnormal range of the fourth state in the memory 131 as first information.

Figure 9:
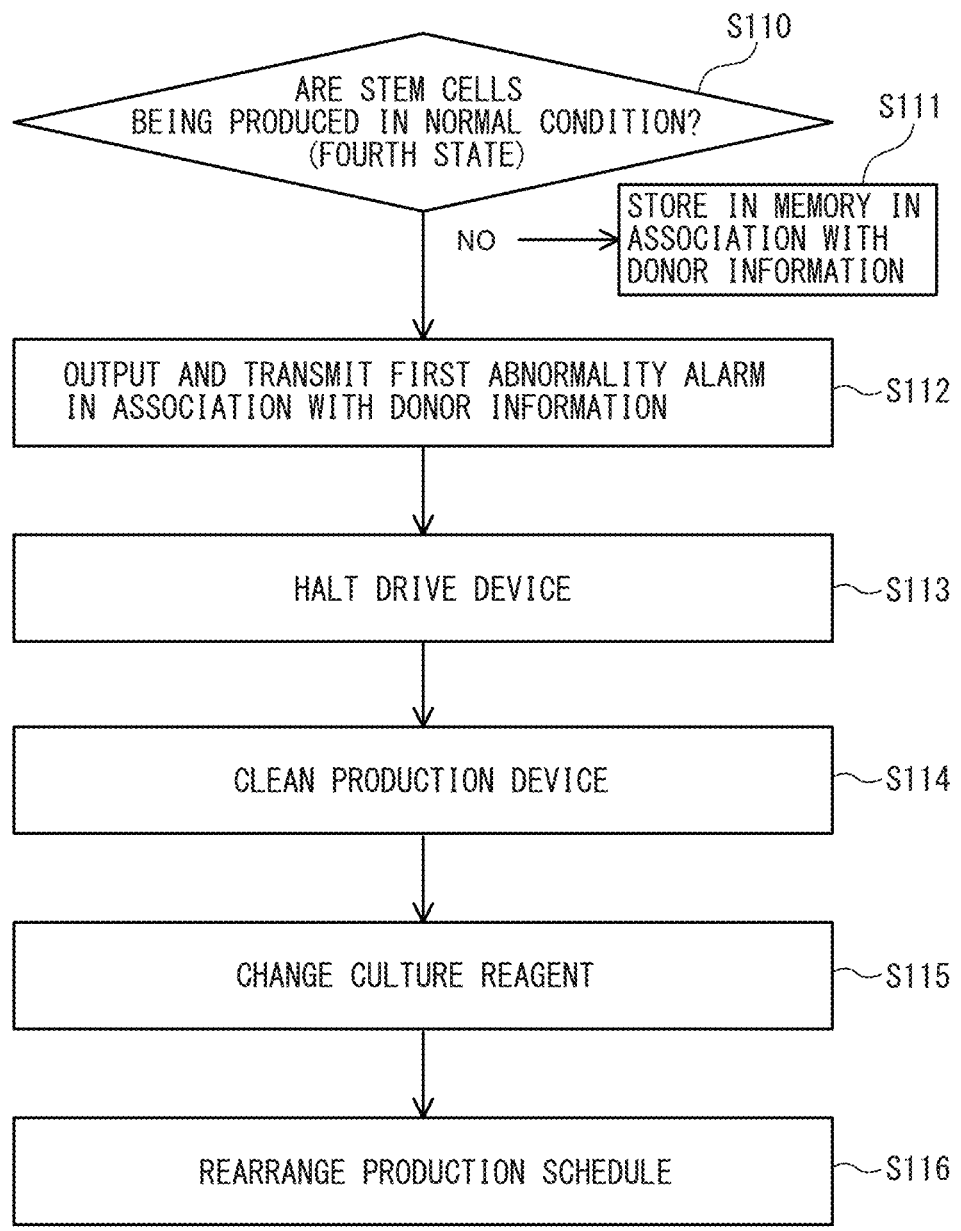
FIG. 9 is a flow chart illustrating an operation of the stem cell manufacturing system according to an embodiment, based on a fourth state.

FIG. 9 is a flow chart illustrating an operation of the stem cell manufacturing system 100 according to the present embodiment, based on the fourth state. When the drive device 130 has determined that the stem cells are not being produced in a normal condition (i.e., information indicating the fourth state (e.g., the ratio of stem cell clusters having a size not less than 100 μm after the initial culture, or the ratio of stem cell clusters having a size of not more than 30 μm in 14 days) is out of the stored normal range or within the abnormal range (not less than 80%)) (step S110), the drive device 130 stores the information indicating the fourth state in the memory 131, in association with the donor ID read from the vial (step S111). The drive device 130 then outputs a first abnormality alarm in association with the donor ID and transmits the abnormality alarm to the mobile terminal 180 in a remote location via the control device 160 and the superordinate computer 170 (step S112). The drive device 130 then comes to a halt, and the production of stem cells is suspended (step S113). The drive device 130 then cleans the inside of the production device 101 with cleaning liquid (step S114) and changes the culture reagent (step S115). The drive device 130 requests the superordinate computer 170 via the control device 160 to rearrange the production schedule for the production device 101 (step S116). According to another embodiment, after the drive device 130 comes to a halt in step 113, the conveyer device 141 may connect a different production device 101 to the drive device 130 to produce stem cells again.

Figure 10:
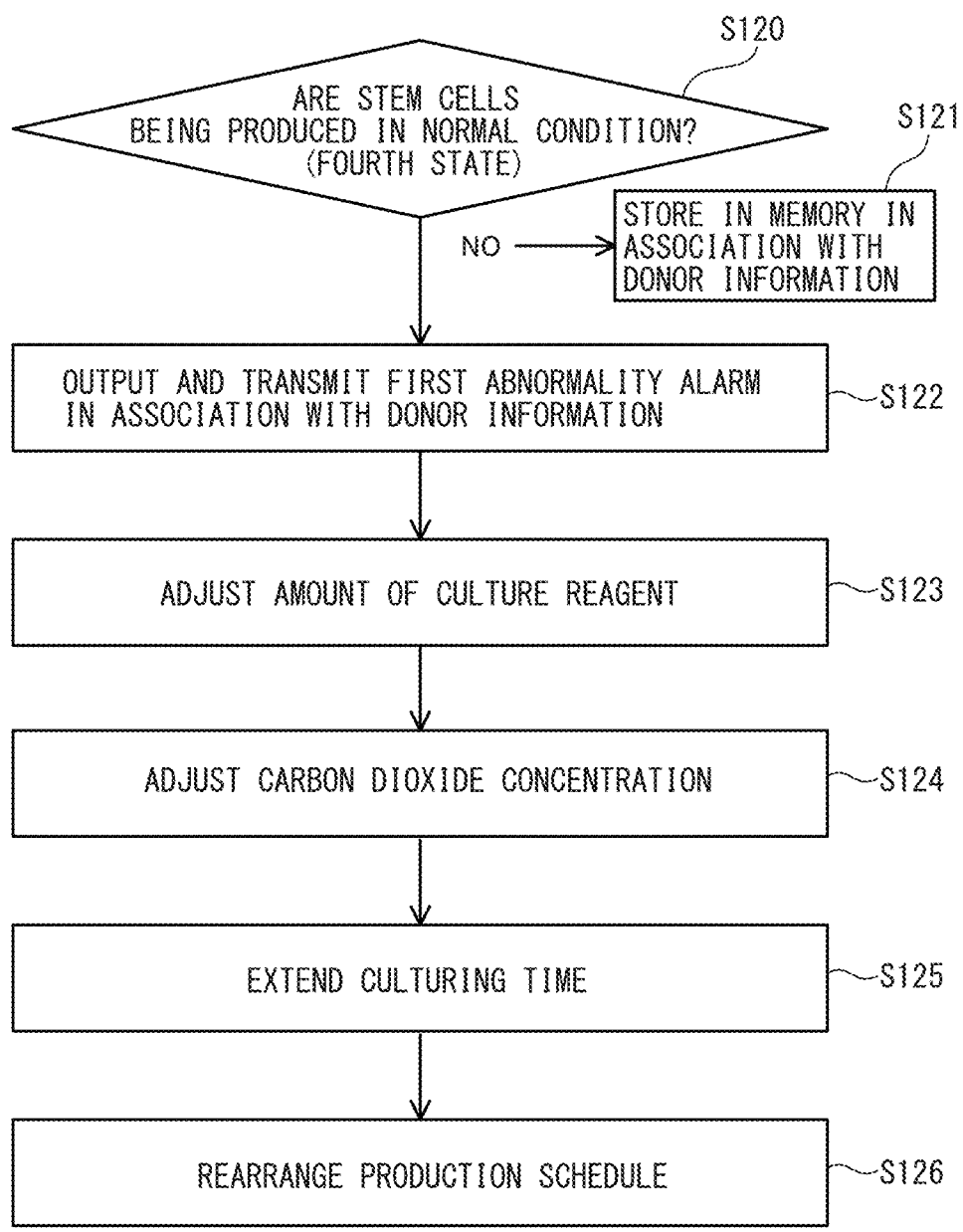
FIG. 10 is a flow chart illustrating an operation of the stem cell manufacturing system according to an embodiment, based on a fourth state.

FIG. 10 is a flow chart illustrating an operation of the stem cell manufacturing system 100 according to the present embodiment, based on the fourth state. As illustrated in FIG. 10, when the drive device 130 has determined that the stem cells are not being produced in a normal condition (i.e., information indicating the fourth state (e.g., the growth speed of the stem cell clusters in the expansion culture) is out of the stored normal range or within the abnormal range (not more than 2 μm/h)) (step S120), the drive device 130 stores the information indicating the fourth state in the memory 131, in association with the donor ID read from the vial (step S121). The drive device 130 then outputs a first abnormality alarm in association with the donor ID and transmits the abnormality alarm to the mobile terminal 180 in a remote location via the control device 160 and the superordinate computer 170 (step S122). The drive device 130 then adjusts the amount of the culture reagent (for example, by increasing the amount of fibroblast growth factor by 5%) (step S123), adjusts the carbon dioxide concentration in the initial culture device 112 and the expansion culture device 114 (for example, by increasing $CO_2$ concentration from 5% to 10%) (step S124), and extends culturing time (for example, by one week) (step S125). The drive device 130 then requests the superordinate computer 170 via the control device 160 to rearrange the production schedule for the production device 101 (step S126).

Referring once again to FIG. 1, the conveyer device 140, by using the vision sensor 143, stores respective inventory quantities of the vials 102 to 105 preserved in the preservation device 150 and respective arrival schedules of the vials 102 to 105 as a fifth state in the memory 146, and transmits information indicating the fifth state to the control device 160. The control device 160 stores the received information indicating the fifth state in a memory 161. According to another embodiment, the preservation device 150, by using the vision sensor 151, may store respective inventory quantities of the vials 102 to 105 preserved in the preservation device 150 and respective arrival schedules of the vials 102 to 105 as a fifth state in the memory 152, and transmit the information indicating the fifth state to the control device 160 by wired or wireless communication.

Figure 11:
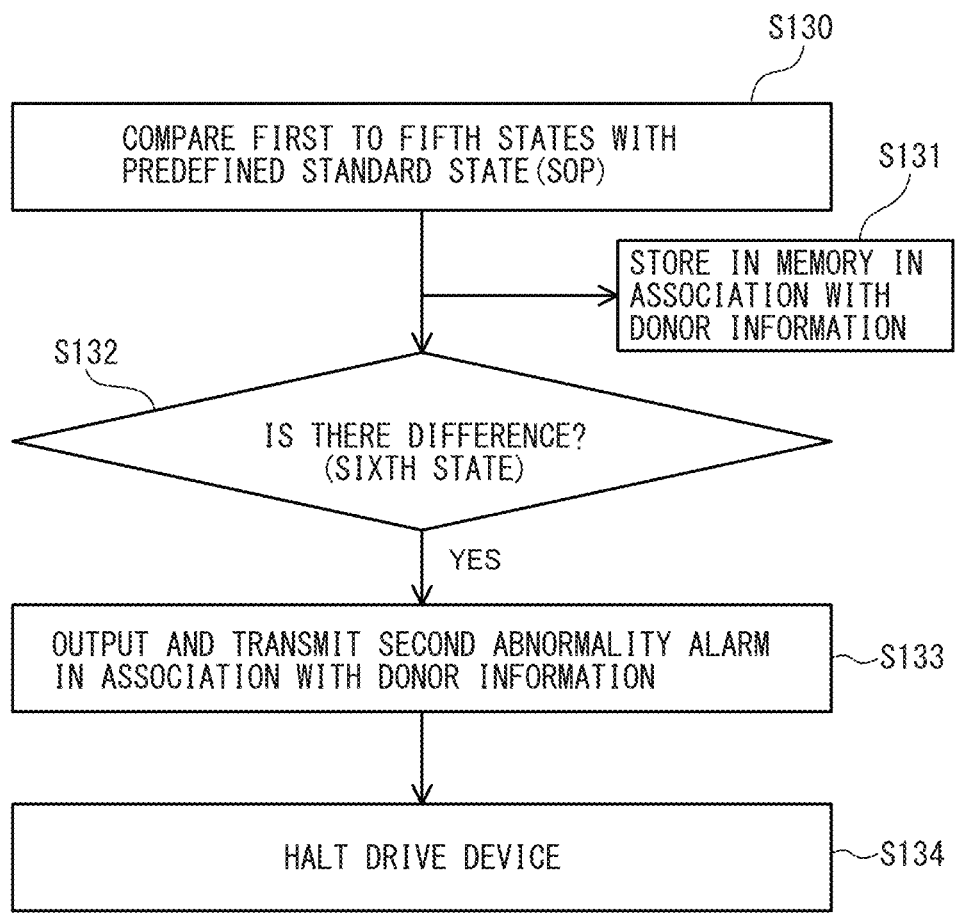
FIG. 11 is a flow chart illustrating an operation of the stem cell manufacturing system according to an embodiment, based on a sixth state.

FIG. 11 is a flow chart illustrating an operation of the stem cell manufacturing system 100 according to the present embodiment, based on the sixth state. The control device 160 compares information indicating at least one of the first to the fifth states, received from the conveyer devices 140 to 142, the drive device 130, and the cryopreservation device 120, with a predefined standard state (e.g., the standard operation procedure (SOP)) (step S130), and stores the presence or absence of a difference (the sixth state), in the memory 161 in association with the donor ID (step S131). When there is a difference between the predefined standard state and information indicating at least one of the first to the fifth states (step S132), the control device 160 outputs a second abnormality alarm in association with the donor ID and transmits the second abnormality alarm to the mobile terminal 180 in a remote location via the superordinate computer 170 (step S133). The control device 160 causes the drive device 130 to come to a halt (step S134). According to another embodiment, the conveyer devices 140 to 141 may compare the information indicating the first state and the second state with the predefined standard state (SOP), the cryopreservation device 120 may compare the information indicating the third state with the predefined standard state (SOP), and the drive device 130 may compare the information indicating the fourth state with the predefined standard state (SOP). According to still another embodiment, in the above-described step S130 to step S131, the control device 160 may compare not the first to the fifth states but other work items with the SOP to determine whether or not the other work items are carried out properly, and store the presence or absence of a difference in association with the donor ID in the memory 161.

FIG. 5 is a perspective view of the cryopreservation device according to the present embodiment. The cryopreservation device 120 includes a container unit 124 containing one or more stem cell freezing vials 103, a vacuum insulated refrigerant chamber 125 configured to contain a refrigerant for cryopreserving the stem cell freezing vial(s) 103 (e.g., liquid nitrogen in the liquid phase at −180° C. or lower and the gas phase at −160° C. or lower), and a supply valve 126 for supplying the refrigerant in advance.

The cryopreservation device 120 further includes a vision sensor 127 for acquiring data in the cryopreservation device 120 and, based on the data from the vision sensor 127, stores in the memory 122 whether or not the stem cells are being stored in a normal condition (see FIG. 6) as a seventh state in numerical form. Such a seventh state may be, for example, the presence or absence of stem cells (or the presence or absence of frozen liquid) in the stem cell freezing vials 103.

The cryopreservation device 120 also includes a temperature sensor 128 configured to detect temperature in the cryopreservation device 120 and, based on the temperature from the temperature sensor 128, stores in the memory 122 whether or not the stem cells are being stored in a normal condition as a seventh state in a numerical from. Such a seventh state in numerical form may be, for example, resistance and voltage of the temperature sensor, or temperature obtained from these. Stem cells are preferably stored at temperatures at −160° C. or lower, and may sustain a serious damage or may perish when they undergo a temperature change of about 20° C.

The cryopreservation device 120 further includes a refrigerant remaining amount sensor 129 configured to detect the remaining amount of refrigerant in the cryopreservation device 120 and, based on the remaining amount from the refrigerant remaining amount sensor 129, stores in the memory whether or not the stem cells are being stored in a normal condition as a seventh state in a numerical from. Such a seventh state may be, for example, voltage or resistance of the remaining amount sensor. The cryopreservation device 120 stores at least one of the normal range and the abnormal range of the seventh state as second information in the memory 122.

Figure 12:
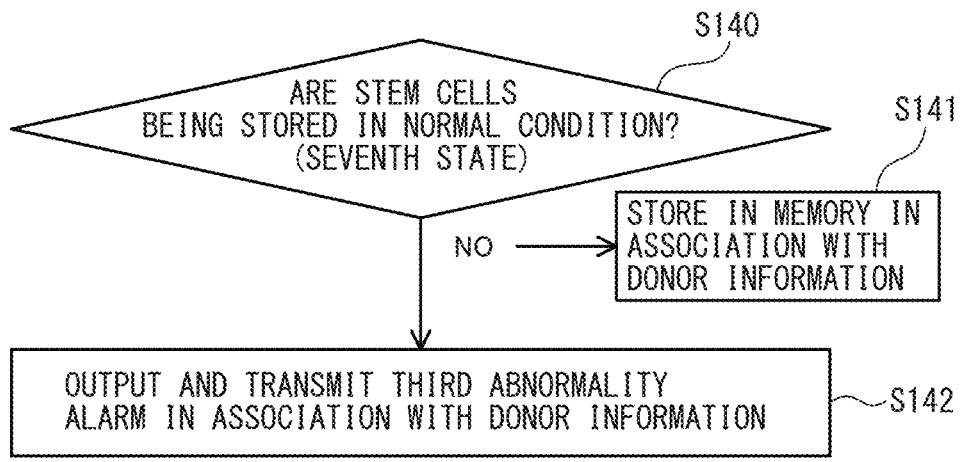
FIG. 12 is a flow chart illustrating an operation of the stem cell manufacturing system according to an embodiment, based on a seventh state.

FIG. 12 is a flow chart illustrating an operation of the stem cell manufacturing system 100 according to the present embodiment, based on the seventh state. When the cryopreservation device 120 has determined that the stem cells are not being stored in a normal condition (i.e., when the information indicating the seventh state (e.g., the temperature from the temperature sensor) is out of the normal range or within the abnormal range (over −160° C.) stored in memory) (step S140), the cryopreservation device 120 stores the information indicating the seventh state in the memory 122 in association with the donor ID read from the vial (step S141). The cryopreservation device 120 then outputs a third abnormality alarm in association with the donor ID and transmits the third abnormality alarm to the mobile terminal 180 in a remote location via the control device 160 and the superordinate computer 170 (step S142).

Figure 13:
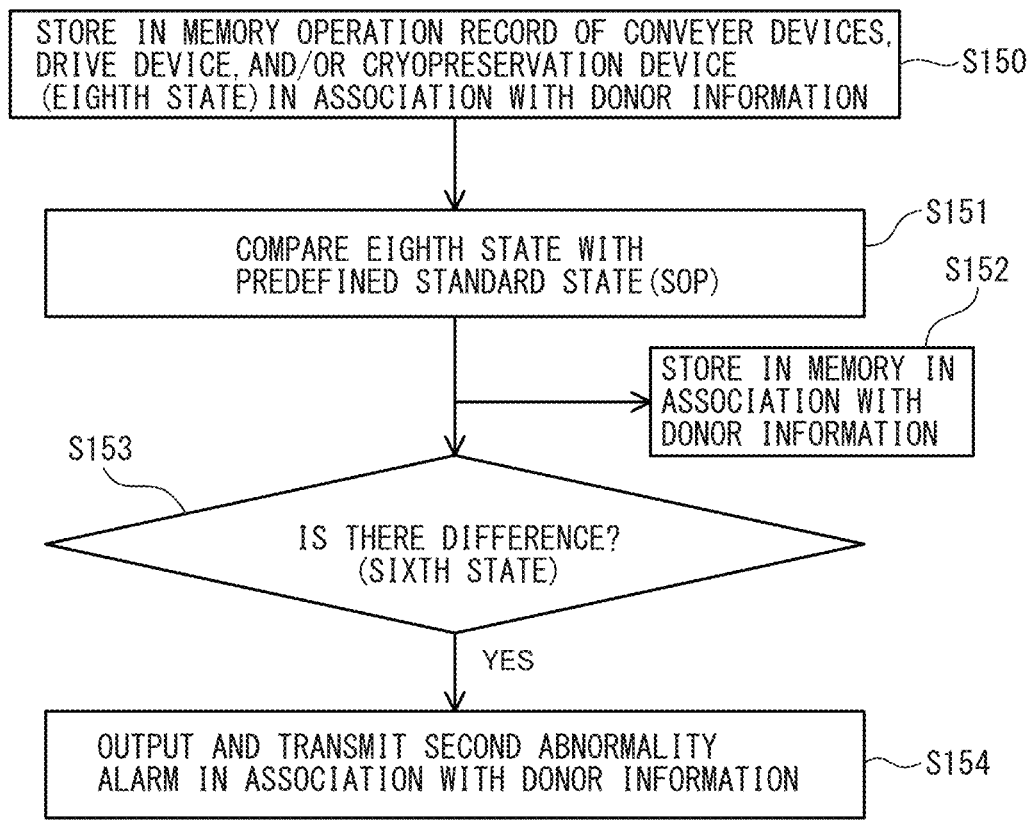
FIG. 13 is a flow chart illustrating an operation of the stem cell manufacturing system according to an embodiment, based on an eighth state.

FIG. 13 is a flow chart illustrating an operation of the stem cell manufacturing system 100 according to the present embodiment, based on the eighth state. The control device 160 stores the operation record of at least one of the conveyer devices 140 to 142, the drive device 130, and the cryopreservation device 120 (the eighth state) in the memory 161 in association with the donor ID (step S150). The control device 160 then compares the eighth state with a predefined standard state (e.g., a standard operation procedure (SOP)) (step S151), and stores in the memory 161 the presence or absence of a difference (the sixth state) in association with the donor ID (step S152). When there is a difference between the eighth state and the predefined standard state (step S153), the control device 160 outputs a second abnormality alarm in association with the donor ID and transmits the second abnormality alarm to the mobile terminal 180 in a remote location via the superordinate computer 170 (step S154). According to another embodiment, the conveyer devices 140 to 142, the drive device 130, and the cryopreservation device 120 store in memory respective operation records (the eighth state) in association with the donor ID and compares the eighth state with the predefined standard state (SOP), and the control device 160 stores the presence or absence of a difference (the sixth state) in association with the donor ID in the memory 161.

The memory that stores at least one of the above-described first to the eighth states may be a single memory provided in a single housing, i.e., the control device or the superordinate computer 170. At least one of the first to the eighth states is transmitted by wireless communication to the mobile terminal 180 in a remote location.

Figure 7:
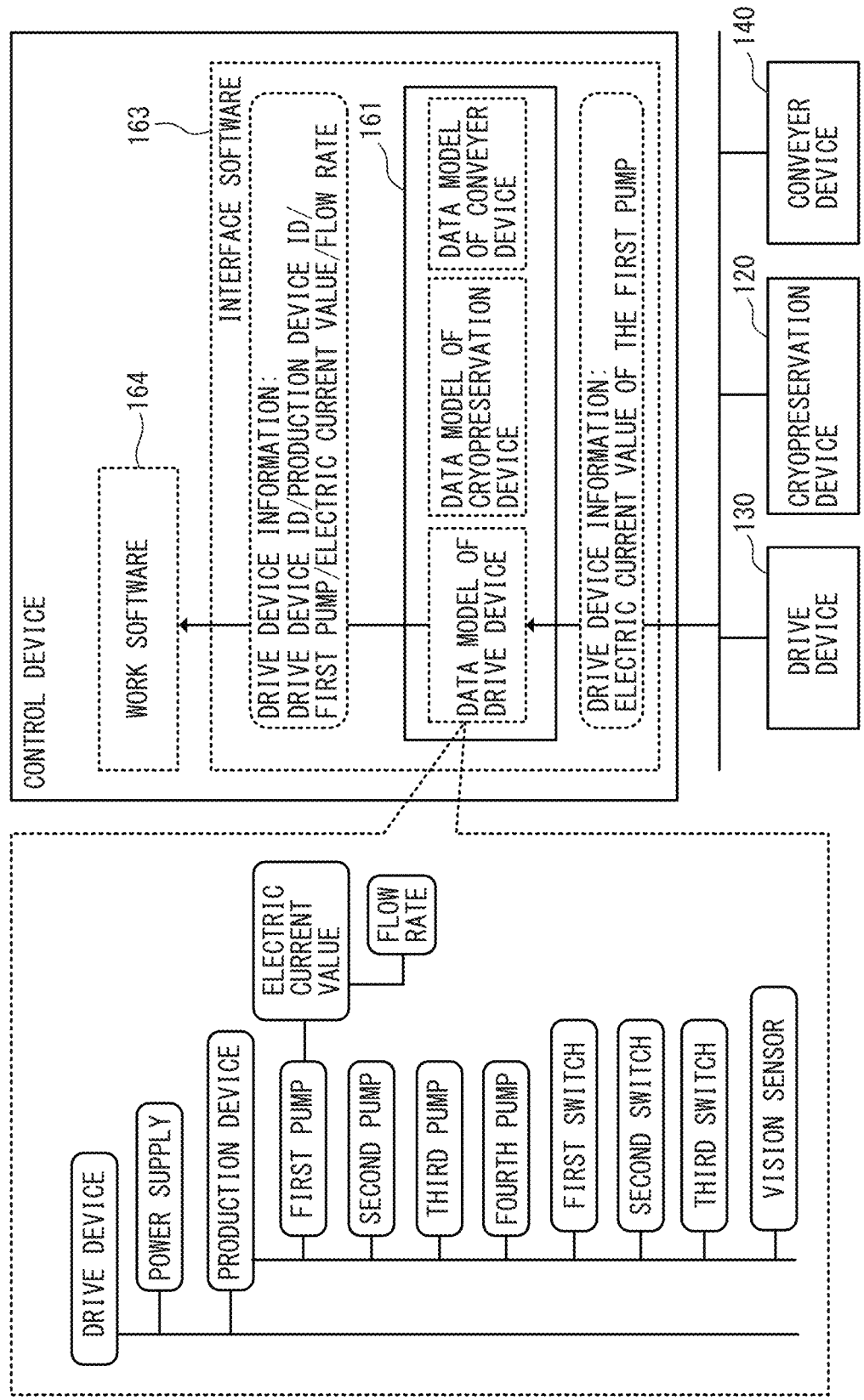
FIG. 7 is a functional block diagram of an application of the FIELD system to the stem cell manufacturing system according to an embodiment.

FIG. 7 is a functional block diagram of an application of the FIELD system to the stem cell manufacturing system 100 according to the present embodiment. The stem cell manufacturing system 100 further includes a control device 160 including interface software 163 and work software 164, and input devices in wired or wireless communication with the control device 160 and configured to input information in the manufacturing process. The input devices may be, for example, the above-described drive device 130, the cryopreservation device 120, and conveyer devices 140 to 142. According to another embodiment, the input devices may be, for example, input devices configured to manually input information indicating at least one of the first to the eighth states.

The control device 160, for example, receives inputs of electric current values of the first to the fourth pumps, voltage values of the first to the third switches, data from the vision sensor, and the like from moment to moment from one or more drive devices 130, receives inputs of resistance values of the temperature sensor, temperature data of the temperature estimation unit, impedance of a somatic cell coagulation monitoring device, voltage values of the refrigerant remaining amount sensor, data from the vision sensor and the like from moment to moment from one or more cryopreservation devices 120, and receives inputs of electric current values of servo motors for respective axes, data from a vision sensor, and the like from moment to moment from the conveyer device 140. Since a large number of input devices of many kinds send out pieces of information unique to a large number of components of many kinds, the control device 160 cannot recognize, for example, by which pump of which drive device working with which production device a certain flow rate is produced. To address this, the interface software 163 converts the information formatted in data formats unique to the input devices into information formatted in a data format unique to the work software 164. The data format unique to the work software 164 is formed with data models having a data structure of tree type or network type indicating subordination relationship of the components of each input device, and the various data models are stored in the memory 161 of the control device 160 in advance. To facilitate understanding, for example, an electric current value of the first pump of the drive device 130, a piece of information unique to the input device, is converted to "drive device ID/production device ID/first pump/electric current value/flow rate", which is in a structured data format unique to the work software. This conversion gives the work software 164 an instant access to data unique to a large number of components of many kinds in a large number of input devices of many kinds.

According to the above-described stem cell manufacturing system 100, a plurality of closed production devices 101 enable the production of stem cells for a plurality of individuals in want of stem cells on a large scale and concurrently, and the closed FA system, which does not need clean rooms, achieves cost reduction, sophisticated quality control, contamination prevention, and solution of human resource shortage. Furthermore, by applying the FIELD system, the time for producing stem cells is reduced. In addition, by reading various identification information attached to each vial, the stem cell manufacturing system 100 prevents cross contamination with somatic cells or stem cells of other individuals. The stem cell manufacturing system 100 makes a great contribution especially for developing an industry in the area of iPS cells for clinical use.

2. Stem Cell Information Management System

Figure 14:
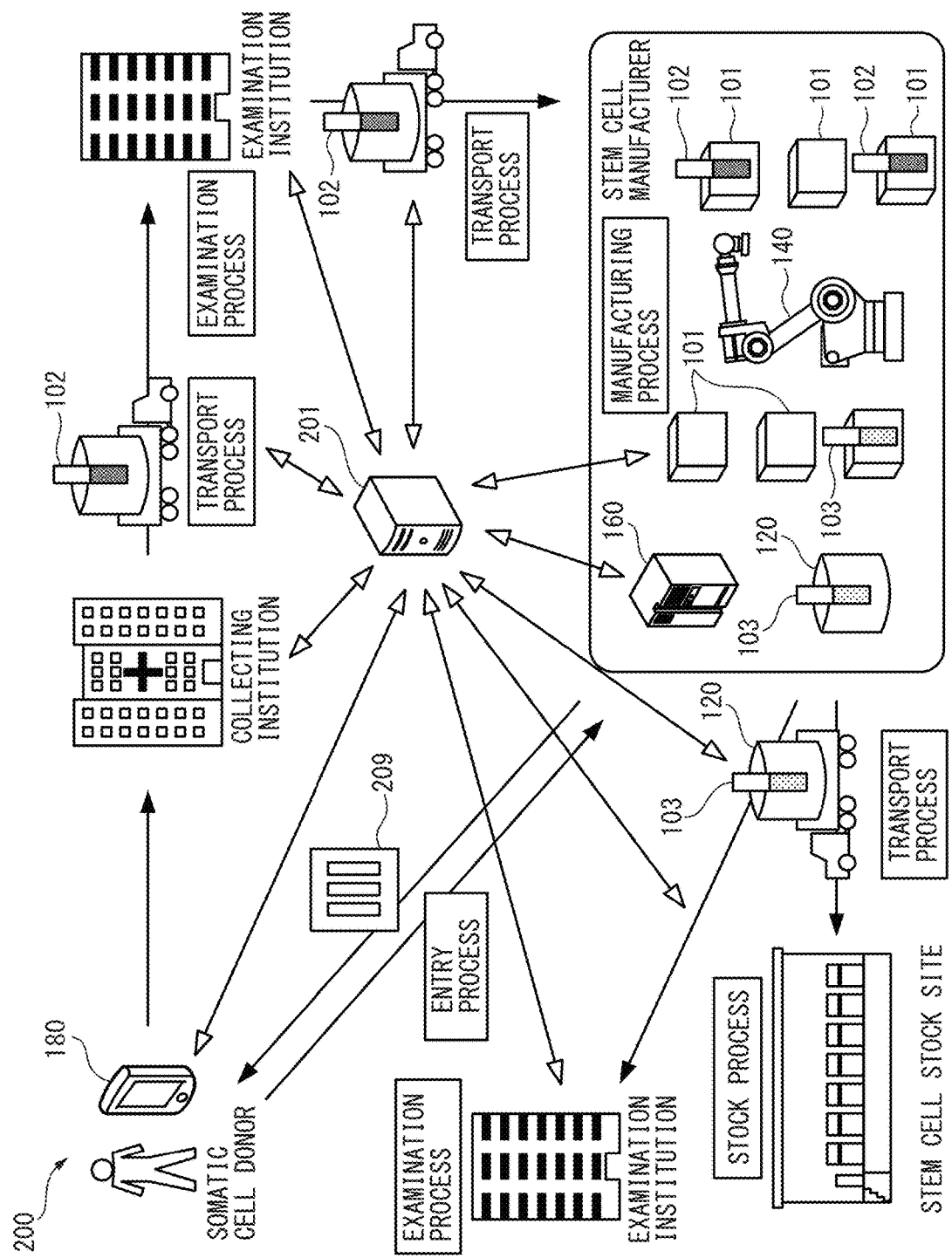
FIG. 14 is a schematic diagram illustrating a server-based configuration of a stem cell information management system according to an embodiment.

FIG. 14 is a schematic diagram illustrating a server-based configuration of a stem cell information management system 200 according to the present embodiment. The stem cell information management system 200 includes a server apparatus 201 on a cloud, and is constituted by a cloud system that performs an integral control of big data in an entry process of receiving a request for manufacturing stem cells from somatic cells, a transport process of transporting somatic cells collected from a somatic cell donor or stem cells produced from somatic cells, an examination process of examining somatic cells or stem cells, a manufacturing process of manufacturing stem cells from somatic cells, and a stock process of stocking stem cells. Such a server apparatus 201 corresponds to the superordinate computer 170 in other drawings. Although a system in which iPS cells are produced from blood cells will be described according to the present embodiment, it should be understood that the invention can be applied to a system in which iPS cells are produced from skin-derived cells, a system in which ES cells are produced from embryonic cells, and other systems. An outline of the processing performed by the stem cell information management system 200 will be described first.

In the entry process, upon receiving a request for manufacturing stem cells, the server apparatus 201 determines all the schedules from the stem cells entry process to the stock process such that stem cells will be produced in a shortest route possible and in a shortest time possible. Upon receiving the request, the server apparatus 201 stores in the memory unit 202 donor information including at least one of informed consent, nationality, address, sex, age, blood type, anamnesis, prescription history, health check results, and family members from whom stem cells are produced in the past, of the somatic cell donor, in association with a donor ID. A collection kit 209 including one or more somatic cell collection vials 102 with the donor ID is then sent specifically to the somatic cell donor himself or herself, which prevents handling of the donor's cells in mistake for somatic cells or stem cells of another individual and failure to attach the correct donor ID to his or her collected cells. According to another embodiment, such a collection kit 209 may be sent not only to the somatic cell donor himself or herself but to the institution at which his or her somatic cells are collected, in advance. The somatic cell collection vial 102 includes an individual identification device 106 that contains, in addition to a donor ID, at least one of an entry ID, a transport ID, an acceptance ID, a manufacturer ID, a production device ID, a cryopreservation device ID, and a stock site ID, as illustrated in FIG. 2.

In the transport process of somatic cells, one or more somatic cell collection vials 102 are placed in a transport container 250, and the transport container 250 is transported from a collection institution to an examination institution and from the examination institution to a stem cell manufacture by transportation means including at least one of automobile, railway, aircraft, ship, and robot. At the time of transport, information on the temperature in the transport container 250, accumulated transportation time, vibration and coagulation state of the somatic cells and the like is transmitted to the server apparatus 201, and the server apparatus 201 performs tasks such as issuing an abnormality alarm and modifying the schedules.

In the examination process of somatic cells, a viral or bacteriological test, a test for blood cell counting, a test for gene expression level measurement, and other tests are conducted on the collected somatic cells. At the time of examination, results of these tests are sent to the server apparatus 201, and the server apparatus 201 performs tasks such as issuing an abnormality alarm and modifying the schedules. In particular, the server apparatus 201 is characterized by that the server apparatus 201 determines a predicted reprogramming rate, which serves as an indicator as to whether or not the somatic cells can be reprogrammed, based on correlation data accumulated from past donors between age, anamnesis, presence or absence of family members from whom stem cells were produced in the past, blood cell count, and presence or absence and measurement of expression of particular genes on one hand and the reprogramming data of the somatic cells on the other, and performs tasks such as issuing an abnormality alarm and modifying the schedules.

In the manufacturing process, information indicating the above-described first state to the eighth states in the stem cell manufacturing system 200 is sent to the server apparatus 201, and the server apparatus 201 performs tasks such as issuing an abnormality alarm and modifying the schedules. When the production device 101 fails to release a stem cell freezing vial 103 in accordance with the predicted release date and time initially set by the server apparatus 201 at the time of receiving the request, the server apparatus 201 performs tasks such as outputting an abnormality alarm and modifying the schedules.

In the transport process of stem cells, stem cell freezing vials 103 containing stem cells manufactured by the stem cell manufacturer are placed in the transport container 250 and transported by transportation means including at least one of automobile, railway, aircraft, ship, and robot. The transport container 250 includes a cryopreservation device 120 containing the above-described refrigerant, but the refrigerant in the cryopreservation device 120 is released through a safety valve as time elapses and the cryopreservation device 120 accordingly has a short-time cryopreservation function only. At the time of transport, information regarding not only temperature in the cryopreservation device 120, accumulated transportation time, vibration, but also remaining amount of refrigerant or remaining amount of reserved refrigerant is sent to the server apparatus 201, and the server apparatus 201 performs tasks such as issuing an abnormality alarm and modifying the schedules.

In the stock process, one or more cryopreservation devices 120 are stocked in the storehouse of a stem cell stock site and refrigerant is stably supplied to the one or more cryopreservation devices 120. The stem cell stock site accordingly has a long-term cryopreservation function. During stock, temperature in the cryopreservation device 120, remaining amount of refrigerant as well as presence or absence of stem cells (or presence or absence of frozen liquid) and the like are sent to the server apparatus 201, and the server apparatus 201 performs tasks such as issuing an abnormality alarm and modifying the schedules.

In the examination process of stem cells, genomic information tests of somatic cells and stem cells, HLA typing tests of somatic cells and stem cells, and other tests are conducted. At the time of examination, information on test results is transmitted to the server apparatus 201, which performs tasks such as issuing an abnormality alarm and modifying the schedules. In particular, the server apparatus 201 is characterized in that the server apparatus 201 determines whether or not the somatic cells and the stem cells are from the same individual, based on the genomic information and the HLA types of the somatic cells and the stem cells, and performs tasks such as issuing an abnormality alarm and modifying the schedules.

Figure 15:
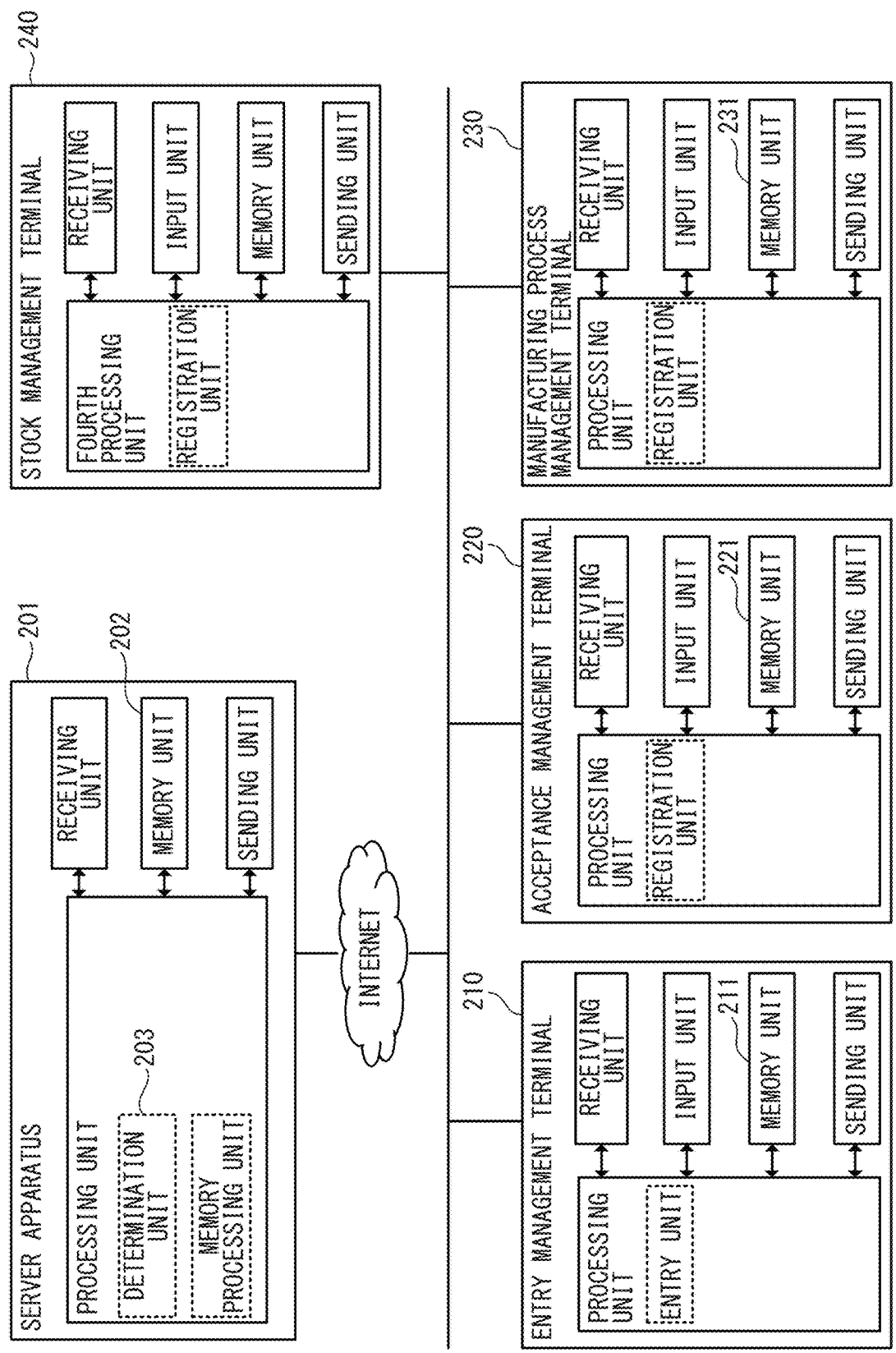
FIG. 15 is a block diagram illustrating a server-based configuration of a stem cell information management system according to an embodiment.

FIG. 15 is a block diagram illustrating a server-based configuration of the stem cell information management system 200 according to the present embodiment. The server apparatus 201 includes memory unit 202 storing a collection schedule for collecting somatic cells from a somatic cell donor, an examination schedule for examining the somatic cells, a production schedule for one or more closed production devices configured to produce stem cells from the somatic cells, a cryopreservation schedule for one or more cryopreservation devices configured to cryopreserve the produced stem cells, a stock schedule for the stock site at which cryopreservation device is stocked, and a determination unit 203 that, upon receiving a request for manufacturing stem cells, determines a schedule such that stem cells will be produced in a shortest route possible and in a shortest time possible, based on the stored collection schedule, examination schedule, production schedule, cryopreservation schedule, and stock schedule. According to another embodiment, the determination unit 203 may determine the schedule based on a supply schedule of the culture reagent and stem cell production material.

As illustrated in FIG. 15, the stem cell information management system 200 further includes an entry management terminal 210 connected with the server apparatus 201 by wired or wireless communication and receiving a request for manufacturing stem cells, an acceptance management terminal 220 that manages acceptance of somatic cells, a manufacturing process management terminal 230 for managing manufacturing process, and a stock management terminal 240 for managing the stocking of stem cells. The acceptance management terminal 220 stores collectable dates of collecting institutions and examinable dates of examination institutions in the memory unit 211 in advance, and the stock management terminal 240 stores stockable locations and stockable periods of stem cell stock sites in the memory unit 241 in advance. According to the present embodiment, these terminal apparatuses 210 to 240 are disposed in a stem cell manufacturer illustrated in FIG. 14, but according to another embodiment they may be disposed in other locations or be formed in a single housing.

Figure 17:
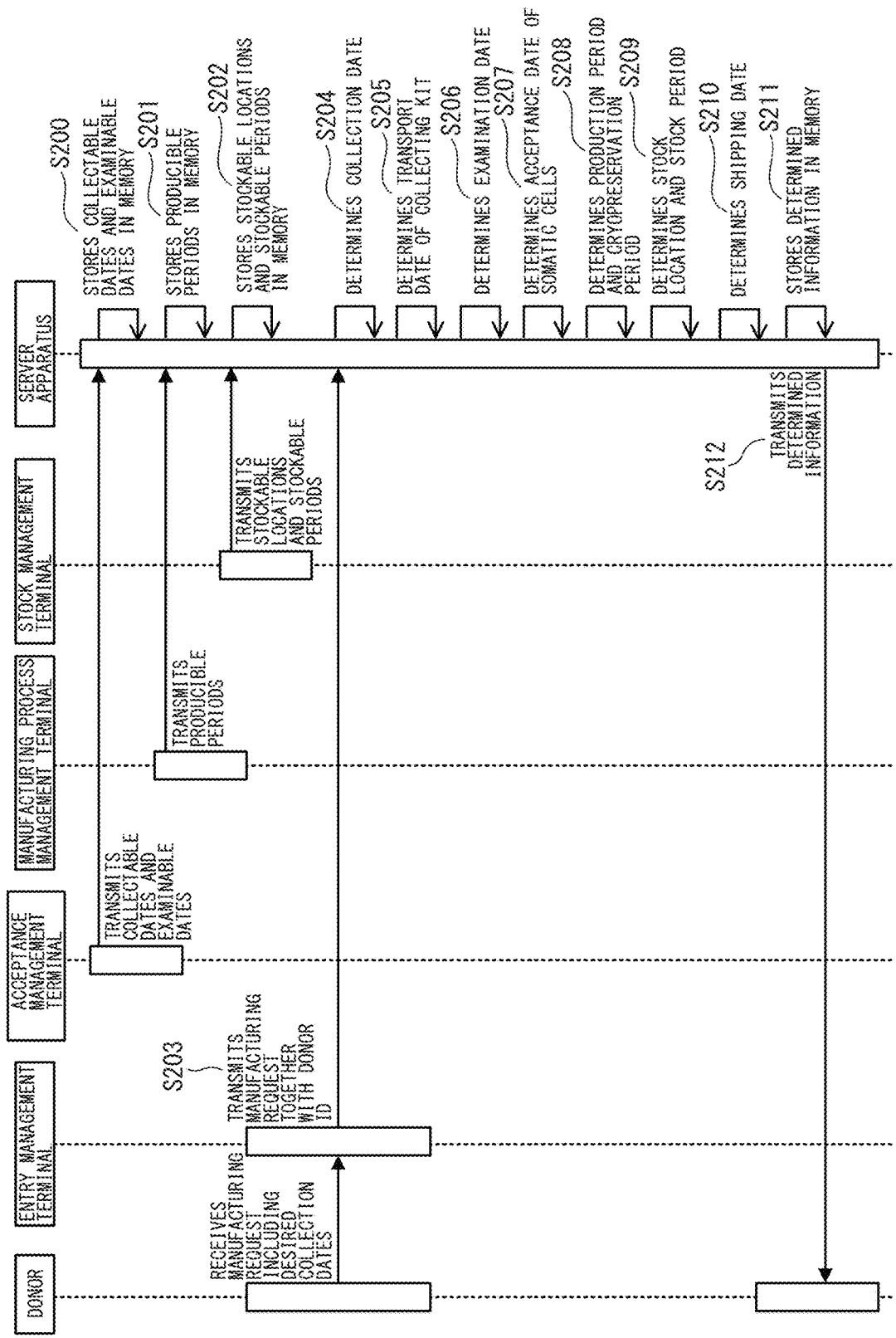
FIG. 17 illustrates a sequence of the server-based operation of the stem cell information management system according to an embodiment.

FIG. 17 illustrates a sequence of an operation of the stem cell information management system 200 according to the present embodiment. The server apparatus 201 receives collectable dates on which somatic cells can be collected and examinable dates on which somatic cells can be inspected from the acceptance management terminal 220 in advance and stores these dates in the memory unit 202 (step S200). According to another embodiment, the server apparatus 201 may directly receive collectable dates from the collecting institutions and examinable dates from the examination institutions. The server apparatus 201 further receives producible periods of one or more closed production devices 101 from the manufacturing process management terminal 230 in advance and stores the periods in the memory unit 202 (step S201). Further, the server apparatus 201 receives stockable locations and stockable periods from the stock management terminal 240 in advance and stores the stockable locations and stockable periods in the memory unit 202 (step S202). According to another embodiment, the server apparatus 201 may directly receive stockable locations and stockable periods from the stock sites.

When the server apparatus 201 receives a manufacturing request including desired collection dates, together with the donor ID from the entry management terminal 210 (step S203), the server apparatus 201 determines a collection date of somatic cells, based on whether or not the one of the desired collection dates falls upon one of the collectable dates (step S204). The server apparatus 201 further determines a transport date such that a collection kit 209 will be transported seven days prior to the determined collection date (step S205). Further, the server apparatus 201 determines an examination date of somatic cells, based on whether or not the date obtained by adding two days for transporting the somatic cells to the determined collection date falls upon one of the examinable dates (step S206). The server apparatus 201 further determines an acceptance date of somatic cells at a stem cell manufacturer, based on whether or not the date obtained by adding seven days for examining the somatic cells and two days for transporting the somatic cells to the determined date of somatic cell examination falls within an producible period of one or more closed production devices 101 (step S207). Further, the server apparatus 201 determines a stem cell production period such that the manufacturing of stem cells may be started immediately from the determined acceptance date of somatic cells (step S208). In other words, the server apparatus 201 determines a stem cell production period based on the determined collection date of somatic cells and the stored producible periods of one or more closed production devices 101. At the time of receiving a request, the server apparatus 201 initially sets a predicted release date and time of the stem cell freezing vials 103 to be released from the closed production devices 101 on a date three months after the date of starting the production. The server apparatus 201 then determines a cryopreservation period, based on whether or not the predicted release date and time of the stem cell freezing vials 103 falls within an cryopreservable period of one or more cryopreservation devices 120 (step S208). The server apparatus 201 then determines a stock location and a stock period of stem cells, based on whether or not the date obtained by adding four days for transporting the stem cells to the predicted release date and time of the stem cell freezing vials 103 falls within a stockable period of the most closely located stockable location among the stockable sites stored in memory (step S209). The server apparatus 201 determines a stem cell shipping date, based on the determined production period and the stockable locations and stockable periods stored in memory (step S210). The server apparatus 201 stores in the memory unit 202 the determined collection date of somatic cells, the transport date of transporting a collection kit 209, the examination date of somatic cells, the acceptance date of somatic cells, the production period of stem cells, the cryopreservation period of stem cells, the stock location and stock period of stem cells, and the shipping date of stem cells in association with the donor ID (step S211) and transmits these dates, locations and periods to the somatic cell donor represented by the donor ID (step S212). According to another embodiment, the server apparatus 201 may determine a cryopreservation period during which somatic cells are temporarily cryopreserved after it has decided the acceptance date of somatic cells in step S207. The cryopreservation period may include, for example, a period for preserving peripheral blood mononuclear cells isolated from the blood.

Referring to FIG. 19 to FIG. 22, how to determine the schedules in the above-described steps S204 to S211 will be described in detail. FIG. 19 to FIG. 22 illustrate a relational database including a donors master 500, a collecting institutions master 501, an examination institutions master 502, a manufactures master 503, a production devices master 504, a cryopreservation devices master 505, an entry table 506, an acceptance table 507, production table 58, a cryopreservation table 509, a stock site master 510, and a stock table 511, stored in the memory unit of the server apparatus 201. In the following, a case of the entry ID 0001 of the entry table 506 in FIG. 21 will be described. In step S204, the donors master 500 in FIG. 19 provides an address corresponding to the donor ID 0102, the collecting institutions master 501 in FIG. 19 reveals that the collecting institution at the collection site most closely located to this address is the one with a collecting institution ID 0001, and the second desired collection date 2018 Mar. 16 in the entry table 506 in FIG. 21 falls upon the first collectable date 2018 Mar. 16 in the collecting institutions master 501 in FIG. 19; therefore, the server apparatus 201 determines that the collection date of somatic cells is to be 2018 Mar. 16.

In step S205, by selecting a date seven days prior to the collection date of somatic cells 2018 Mar. 16 specified in the entry table 506 in FIG. 21, the server apparatus 201 determines that the transport date of the collection kit 209 is to be 2018 Mar. 9. In step S206, by adding to the collection date of somatic cells 2018 Mar. 16 two days for transporting the somatic cells, the date 2018 Mar. 18 is obtained, which falls upon the second examinable dates 2018 Mar. 18 of the most closely located examination institution in the examination institutions master 502 in FIG. 19; therefore, the server apparatus 201 determines that the examination date of somatic cells is to be 2018 Mar. 18. In step S207, referring to the entry table 506 in FIG. 21, by adding seven days for examining the somatic cells and two days for transporting the somatic cells to the examination date of somatic cells 2018 Mar. 18, the date 2018 Mar. 27 is obtained, and this date falls within the producible period from 2018 Mar. 16 to 2018 Mar. 16 corresponding to the manufacturer ID 0001 specified in the production table 508 in FIG. 22; therefore, the server apparatus 201 determines that the acceptance date of somatic cells is to be 2018 Mar. 27, as illustrated in the acceptance table 507 in FIG. 21.

Figure 22:
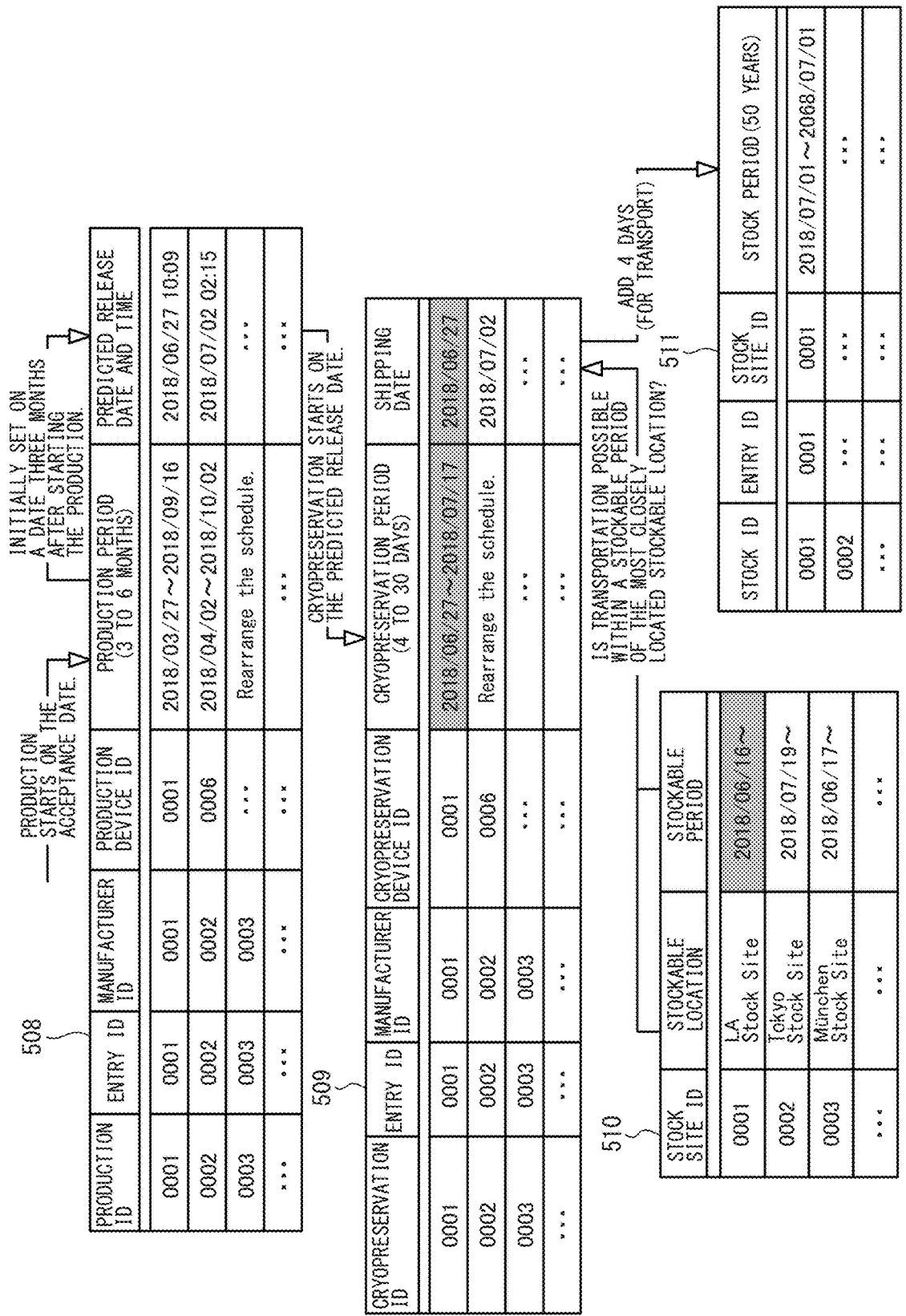
FIG. 22 illustrates a production table, a cryopreservation table, a stock site master, and a stock table of the stem cell information management system according to an embodiment.

In the case of the entry ID 0003 in the entry table 506 in FIG. 21, however, by adding seven days for examining the somatic cells and two days for transporting the somatic cells to the examination date of somatic cells 2018 Mar. 27, the date 2018 Apr. 5 is obtained, which does not fall within the producible period corresponding to the manufacturer ID 0003 specified in the production table 508 in FIG. 20; therefore, the server apparatus 201 issues an alarm for rearranging the schedules, as illustrated in the production table 508 in FIG. 22, and prompts an inquiry of the somatic cell donor for other desired collection dates.

Returning to the case of the entry ID 0001, in step S208, the server apparatus 201 determines that the production period is to be from 2018 Mar. 27 to 2018 Mar. 16 as illustrated in the production table 508 in FIG. 22 so that the production of the stem cells may be started immediately from the acceptance date of somatic cells 2018 Mar. 27. In step S209, the server apparatus 201 sets the predicted release date and time of the stem cell freezing vial in FIG. 22 on 2018 Jun. 27, which is three months after the production starting date 2018 Mar. 27. Since the predicted release date and time 2018 Jun. 27 falls within an cryopreservable period from 2018 Jun. 18 to 2018 Jul. 17 in the cryopreservation devices master 505 in FIG. 20, the server apparatus 201 determines that the cryopreservation period is to be from 2018 Jun. 27 to 2018 Jul. 17, as illustrated in the cryopreservation table 509 in FIG. 22.

In the case of the entry ID 0002 in the production table 508 in FIG. 22, however, the predicted release date and time 2018 Jul. 2 does not fall within any of cryopreservable periods for the manufacturer ID 0002 in the cryopreservation devices master 505 in FIG. 20, the server apparatus 201 issues an alarm for rearranging the schedules, as illustrated in the cryopreservation table 509 in FIG. 22, and prompts an inquiry of the somatic cell donor for other desired collection dates.

Returning to the case of the entry ID 0001, in step S210, by adding to the predicted release date and time 2018 Jun. 27 in the production table in FIG. 22 four days for transport, the date 2018 Jul. 1 is obtained, which date falls within an stockable period 2018 Jun. 16 of the LA stock site at the most closely located stock location of the stockable locations in the stock site master 510 in FIG. 22; therefore, the server apparatus 201 determines that the stock location is to be the LA stock site and that the stock period is to be 50 years starting from 2018 Jul. 1. In step S211, the server apparatus 201 determines that the shipping date of stem cells is to be 2018 Jun. 27, which is the predicted release date and time.

Figure 16:
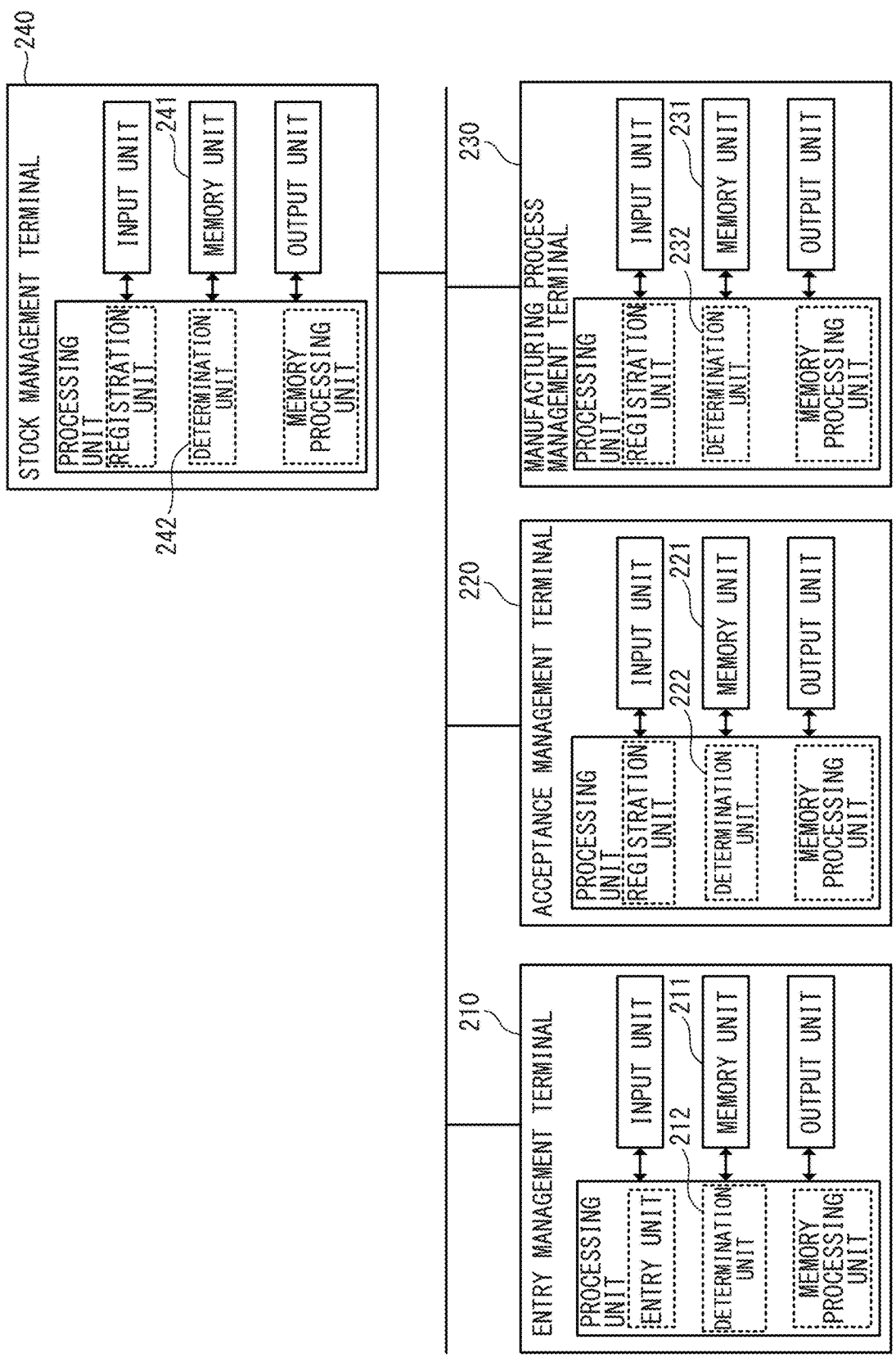
FIG. 16 is a block diagram illustrating a medium-based configuration of a stem cell information management system according to another embodiment.

FIG. 16 is a block diagram illustrating a medium-based configuration of a stem cell information management system 260 according to another embodiment. The stem cell information management system 260 differs from the server-based configuration of the stem cell information management system 260 only insofar as it does not use the server apparatus 201, and otherwise the configuration is the same as the server-based configuration. The stem cell information management system 260 transfers various information among terminal apparatuses 210 to 240 by paper medium or telecommunication medium. Since the stem cell information management system 260 does not use the server apparatus 201 on a cloud, it is secure and prevents personal information from being leaked. The stem cell information management system 260 includes an entry management terminal 210, an acceptance management terminal 220, a manufacturing process management terminal 230, and a stock management terminal 240, connected with one another by wired or wireless communication. The terminal apparatuses 210 to 240 respectively include determination units 212, 222, 232, 242 that determine various information such as schedules and memory units 211, 221, 231, 241 that store various data.

Figure 18:
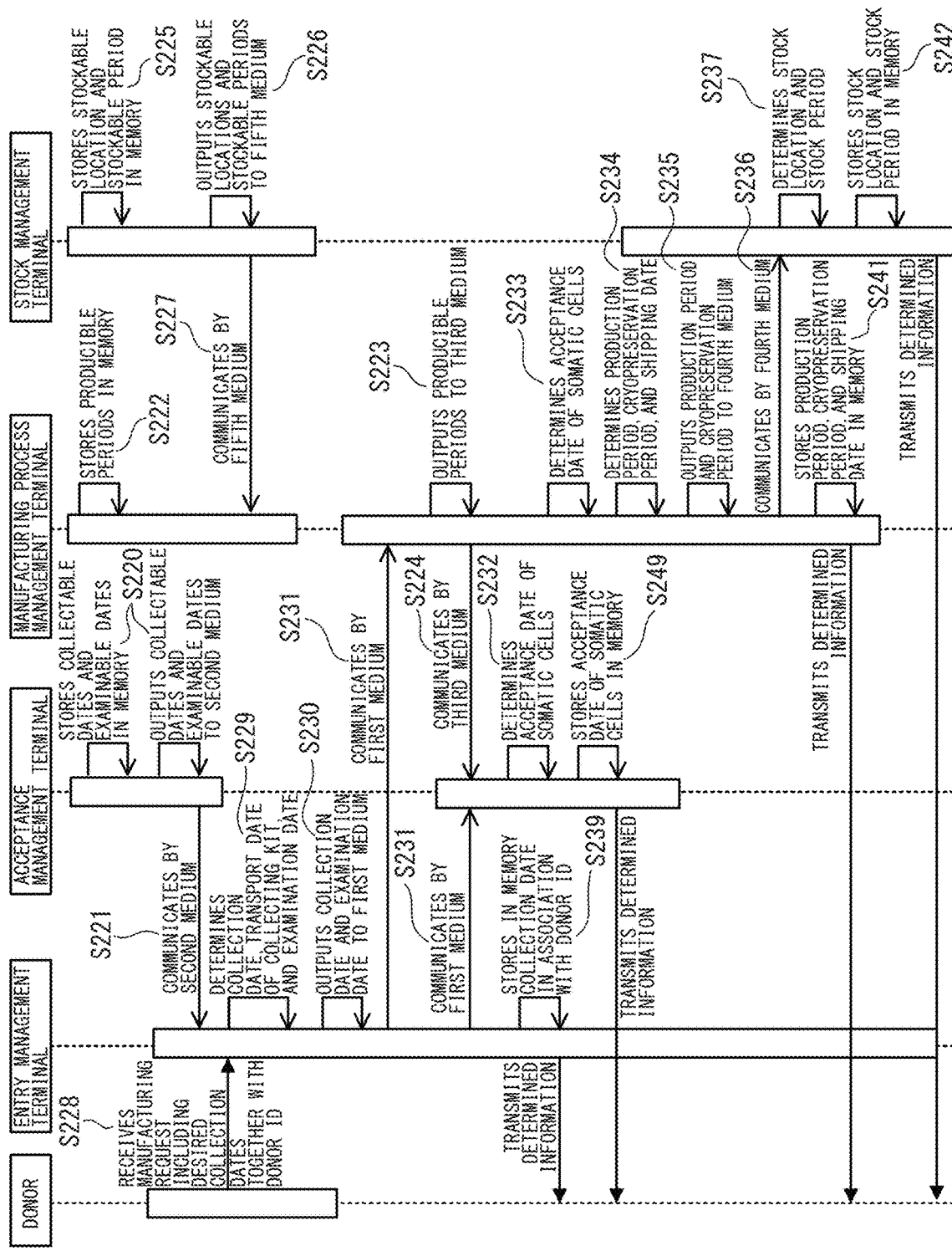
FIG. 18 illustrates a sequence of the medium-based operation of the stem cell information management system according to another embodiment.

FIG. 18 illustrates a sequence of an operation of the stem cell information management system 260. The acceptance management terminal 210 stores collectable dates of the collecting institutions and examinable dates of the examination institutions in the memory unit 221 in advance (step S220), outputs the collectable dates and the examinable dates to a second medium and communicates the dates to the entry management terminal 210 (step S221). The manufacturing process management terminal 230 stores producible periods of the production device(s) in the memory unit 231 in advance (step S222), outputs the producible periods to a third medium (step S223), and communicates the periods to the acceptance management terminal 220 (step S224). The stock management terminal 240 stores stockable locations and stockable periods of the stock sites in the memory unit 241 in advance (step S225), outputs the stockable locations and the stockable periods to a fifth medium (step S226), and communicates the stockable locations and stockable periods to the manufacturing process management terminal 230 (step S227).

When the entry management terminal 210 receives a manufacturing request including desired collection dates together with the donor ID (step S228), the entry management terminal 210 determines a collection date of somatic cells, based on whether or not one of the desired collection dates falls upon one of the collectable dates communicated by the second medium (step S229). The entry management terminal 210 further determines a transport date such that a collection kit 209 will be transported seven days before the determined collection date (step S229). The entry management terminal 210 also determines an examination date of somatic cells, based on whether or not the date obtained by adding two days for transportation to the determined collection date falls upon one of the examinable dates communicated by the second medium (step S229). The entry management terminal 210 outputs the determined collection date and the examination date to a first medium (step S230), and communicates the dates to the acceptance management terminal 220 and the manufacturing process management terminal 230 (step S231).

The acceptance management terminal 220 determines an acceptance date of somatic cells, based on whether or not the date obtained by adding seven days for examining the somatic cells and two days for transporting the somatic cells to the examination date communicated by the first medium falls within one of the producible periods communicated by the third medium (step S232). In other words, the acceptance management terminal 220 determines an acceptance date of somatic cells, based on the determined collection date and the producible periods communicated by the third medium.

The manufacturing process management terminal 230 determines an acceptance date of somatic cells by the same procedure as the entry management terminal 210 (step S233). The manufacturing process management terminal 230 determines a stem cell production period so that the production of the stem cells may be started immediately from the determined acceptance date of somatic cells (step S234). In other words, the manufacturing process management terminal 230 determines a stem cell production period, based on the collection date of somatic cells communicated by the first medium and the producible periods stored in memory. Further, the manufacturing process management terminal 230 initially sets a predicted release date and time of the stem cell freezing vial to be released from the closed production device on the date three months after the production starting date, and determines a cryopreservation period, based on whether or not the predicted release date and time falls within an cryopreservable period of the cryopreservation device (step S234). The manufacturing process management terminal 230 then determines a shipping date of stem cells, based on whether or not the date obtained by adding four days for transporting the stem cells to the predicted release date and time falls within an stockable period of the most closely located stockable location of the stockable locations communicated by the fifth medium (step S234). In other words, the manufacturing process management terminal 230 determines a shipping date of stem cells, based on the production period of stem cells and the stock locations and stock periods communicated by the fifth medium. The manufacturing process management terminal 230 outputs the determined production period and the cryopreservation period to a fourth medium (step S235), and communicates these periods to the stock management terminal 240 (step S236).

The stock management terminal 240 determines a stock location and stock period of stem cells by the same procedure as the manufacturing process management terminal 230 (step S237). In other words, the stock management terminal 240 determines a stock location and stock period of stem cells, based on the production period of stem cells communicated by the fourth medium and the stockable locations and stockable periods stored in memory.

The entry management terminal 210 stores the determined collection date, the transport date of transporting a collection kit, the examination date of somatic cells, and the like in the memory unit 211 in association with the donor ID, and transmits these dates to the donor (step S239). Similarly, the acceptance management terminal 220 stores the determined acceptance date of somatic cells in the memory unit 221 in association with the donor ID, and transmits the date to the donor (step S240). Similarly, the manufacturing process management terminal 230 stores the determined production period, the cryopreservation period, and the shipping date in the memory unit 231 in association with the donor ID, and transmits the periods and the date to the donor (step S241). The stock management terminal 240 stores the determined stock location and stock period in the memory unit 241 in association with the donor ID, and transmits the stock location and stock period to the donor (step S242).

According to the stem cell information management systems 200, 260, in either server-based or medium-based configuration, when a manufacturing request is received, the determination unit of the server apparatus 201 determines or the determination units of the terminal apparatuses 210 to 240 determine a production schedule of stem cells according to the shortest route and the shortest time, which shortens the production time and provides a sophisticated quality control.

Figure 23:
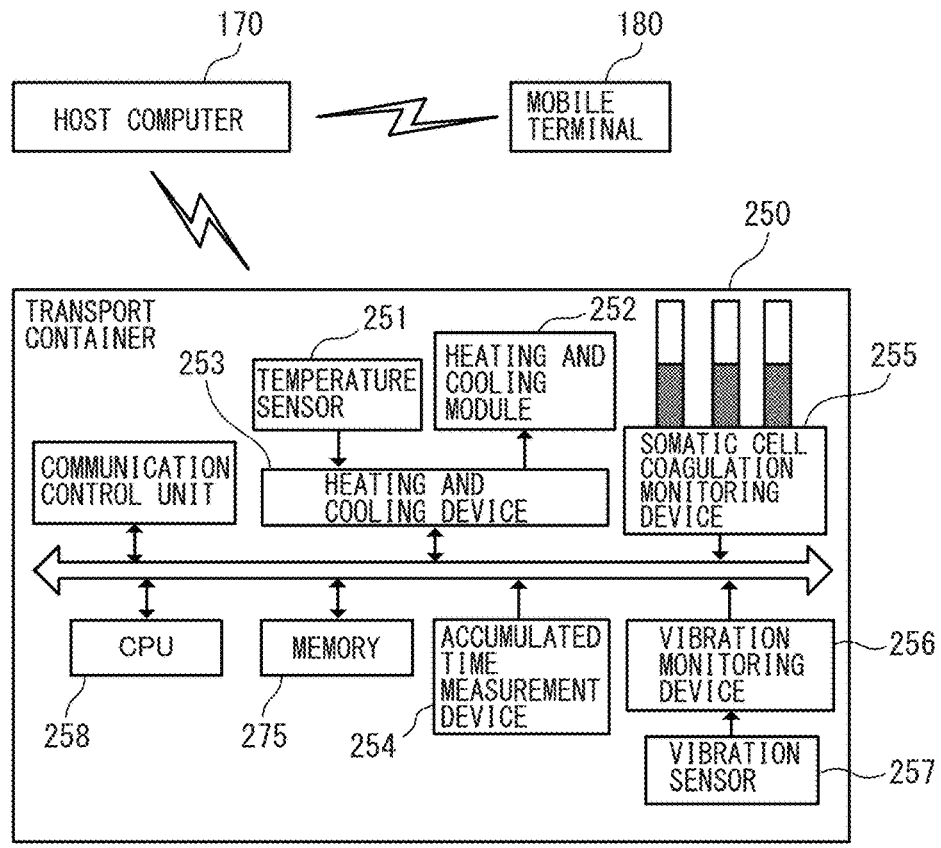
FIG. 23 is a block diagram of a somatic cell transport container according to an embodiment.

In the following, modification of a schedule in response to an abnormality in the transport process, the examination process, and the manufacturing process will be described based on the stem cell information management system 200 with the server-based configuration. FIG. 23 to FIG. 27 illustrate a configuration and an operation of the stem cell information management system 200 in the transport process. As illustrated in FIG. 23, the stem cell information management system 200 further includes a transport container 250 configured to contain one or more somatic cell collection vials. The transport container 250 includes at least one of a heating and cooling device 253 connected with a temperature sensor 251 and a heating and cooling module 252, an accumulated time measurement device 254 measuring accumulated transportation time of the transport container 250, a somatic cell coagulation monitoring device 255 monitoring the coagulating state of the somatic cells in the somatic cell collection vial, and a vibration monitoring device 256 monitoring vibration of the transport container 250. The transport container 250 further includes a memory 275 storing various data, a communication control unit in a wireless communication with a superordinate computer, and a CPU 258 that controls the whole transport container 250.

Figure 24:
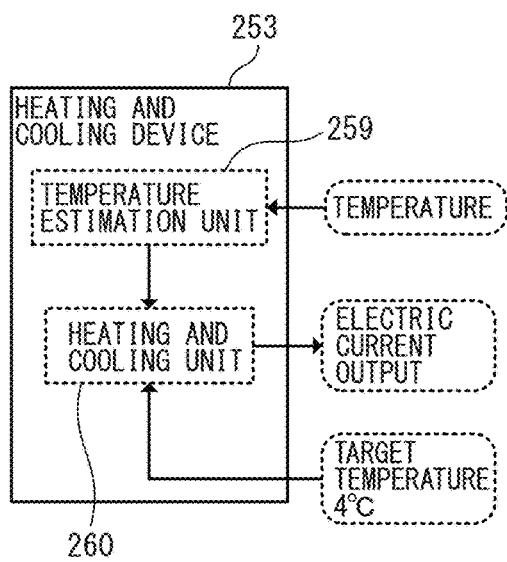
FIG. 24 is a functional block diagram of a heating and cooling device in the somatic cell transport container according to an embodiment.

As illustrated in FIG. 24, the heating and cooling device 253 includes a temperature estimation unit 259 estimating the temperature of the somatic cells in the transport container 250, and a heating and cooling unit 260 automatically performing heating or cooling in conjunction with the temperature data from the temperature estimation unit so that the temperature may be kept constant. The temperature estimation unit 259 estimates the temperature of the somatic cells, based on the temperature from the temperature sensor 251 and the thermal conductivity of the somatic cell collection vial 102. The heating and cooling unit 260 outputs electric current to a heating and cooling module 252 so that the temperature data for the temperature estimation unit 259 may be equal to a target temperature (e.g., 4° C.). Further, the heating and cooling device 253 stores in memory an upper temperature limit and a lower temperature limit, and issues a temperature-related abnormality alarm when the temperature data from the temperature estimation unit 259 is equal to or higher than the upper temperature limit or equal to or lower than the lower temperature limit.

The accumulated time measurement device 254 includes a timer device (not illustrated) with a start function and a stop function, and measures accumulated transportation time starting from the collection date and time of the somatic cells or the release of the stem cell freezing vials 103. The accumulated time measurement device 254 stores in memory a time period during which the quality of the somatic cells or the stem cells can be maintained and outputs a time-related abnormality alarm when the accumulated transportation time exceeds the time period during which the quality can be maintained.

Figure 25:
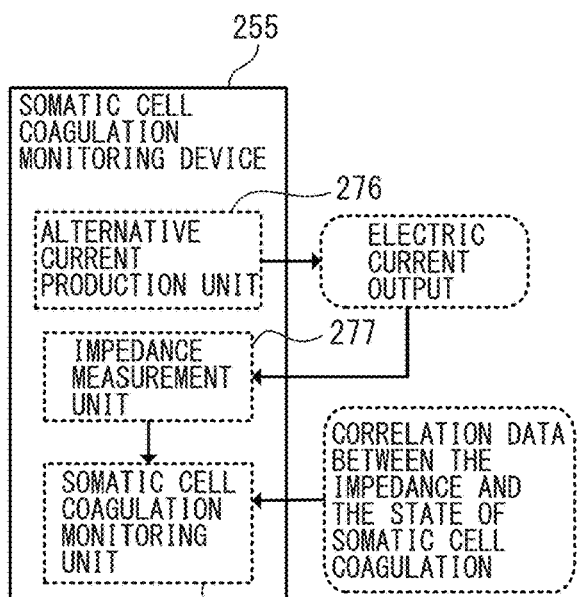
FIG. 25 is a functional block diagram of a somatic cell coagulation monitoring device in the somatic cell transport container according to an embodiment.

As illustrated in FIG. 25, the somatic cell coagulation monitoring device 255 includes, an alternative current production unit 276 producing alternative current, an impedance measurement unit 277 measuring impedance from the alternative current applied to the somatic cells, and a somatic cell coagulation monitoring unit 278 monitoring the state of somatic cell coagulation, based on the correlation data between the impedance and the state of somatic cell coagulation stored in memory in advance. The somatic cell coagulation monitoring device 255 stores in memory an upper limit and a lower limit for a numerical value representing the state of coagulation (e.g., impedance, or somatic cell coagulation value calculated from impedance), and outputs an coagulation-related abnormality alarm when the value of somatic cell coagulation is equal to or greater than the upper limit or equal to or smaller than the lower limit.

The vibration monitoring device 256 is provided with a vibration sensor 257 configured to detect vibration of the transport container 250 (displacement in three-dimension directions, velocity, acceleration, or force), and outputs a vibration-related abnormality alarm when a numerical value representing vibration detected by the vibration sensor 257 (e.g., the integral of the absolute value of acceleration with respect to time, as a value having a correlation with a total energy of vibration) exceeds an upper limit.

Figure 27:
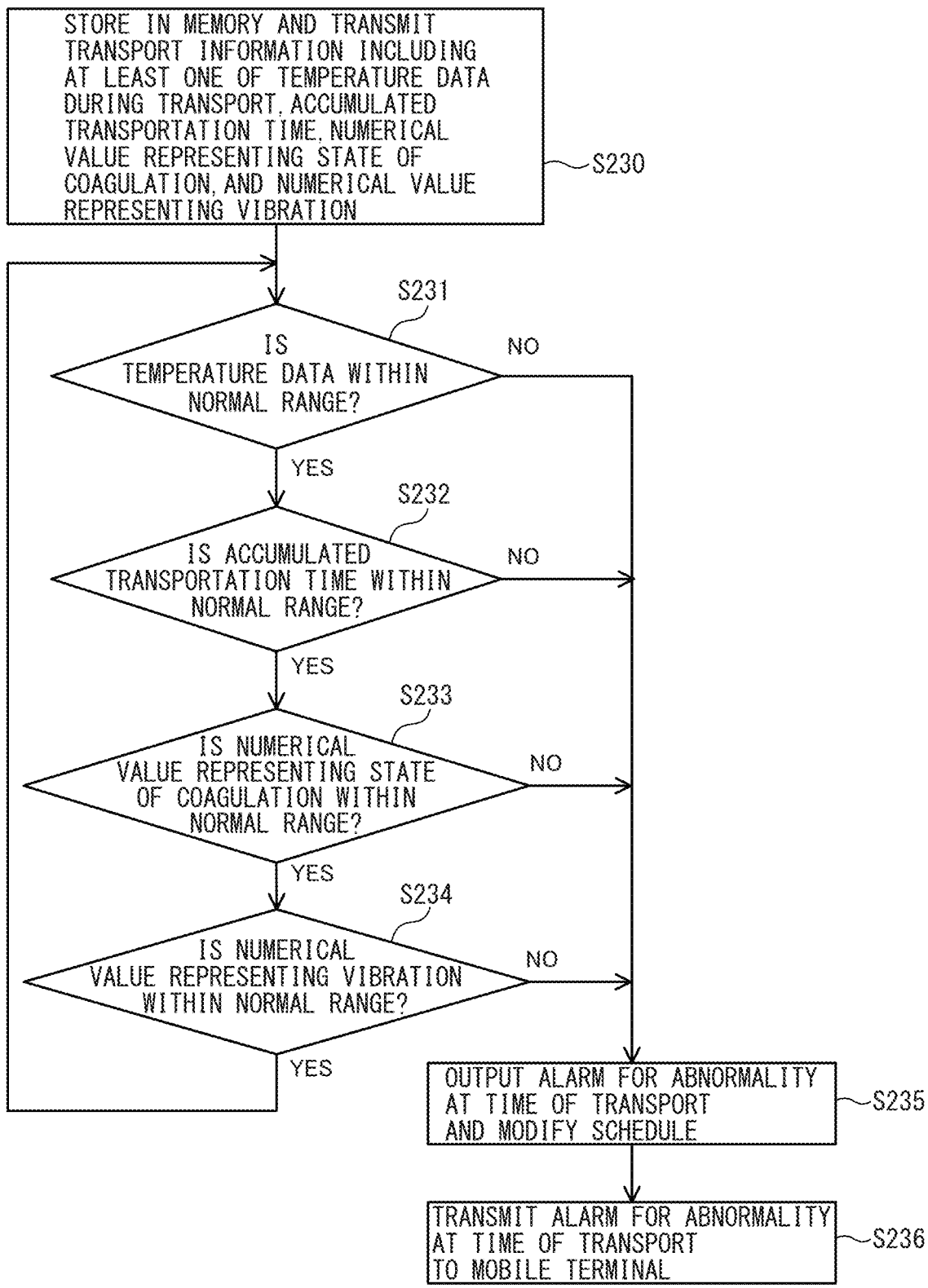
FIG. 27 is a flow chart illustrating a transport operation of the stem cell information management system according to an embodiment.

FIG. 26 illustrates a transport table 512 containing transport information and FIG. 27 illustrates an operation of the stem cell information management system 200, based on the transport information. The transport container 250 stores in a memory 275 transport information including at least one of the above-described temperature data, accumulated transportation time, a numerical value representing the state of coagulation, a numerical value representing the vibration in association with at least the donor ID, and transmits the transport information to the server apparatus 201 serving as the superordinate computer 170 (step S230). When at least one of the temperature data (step S231), the accumulated transportation time (step S232), the numerical value representing the state of coagulation (step S233), and the numerical value representing the vibration (step S234) is out of the normal range, the server apparatus 201 determines to output an alarm for an abnormality at the time of transport and modify the schedule (step S235), and transmits an alarm for an abnormality at the time of transport and the transport information to the mobile terminal 180 in a remote location (step S236).

Figure 28:
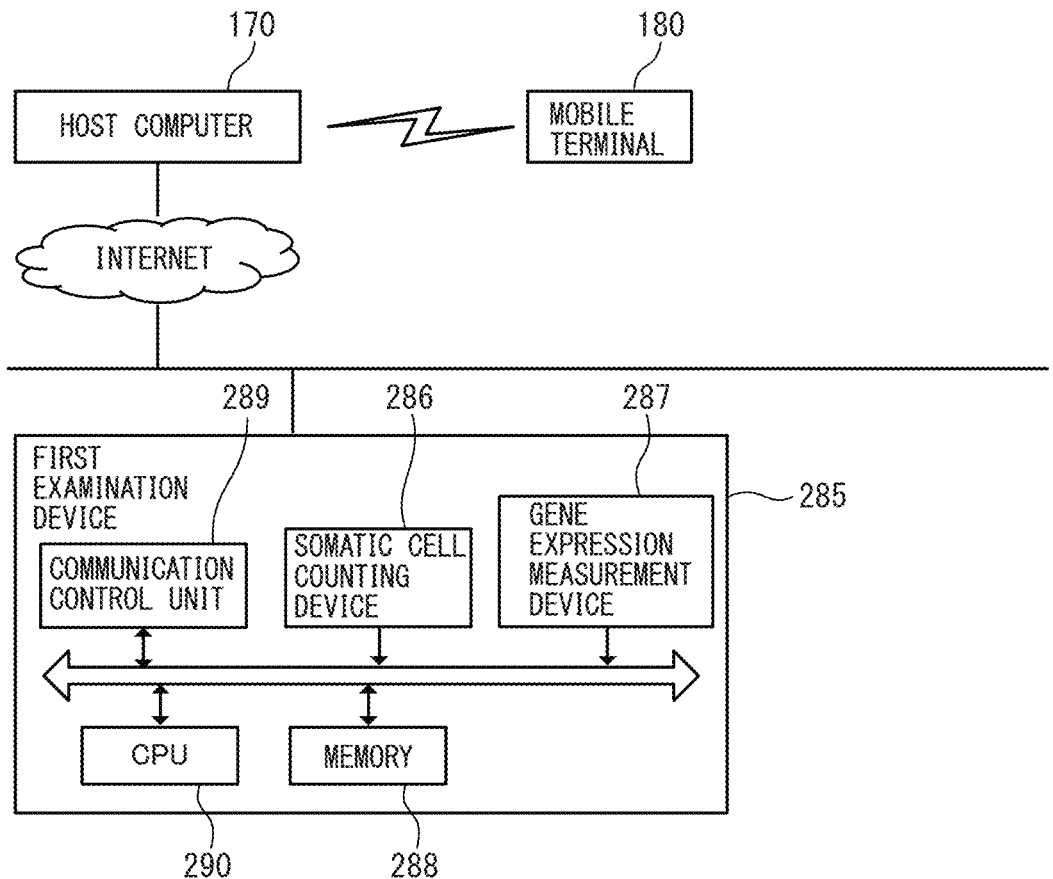
FIG. 28 is block diagram of a first examination device according to an embodiment.
Figure 29:
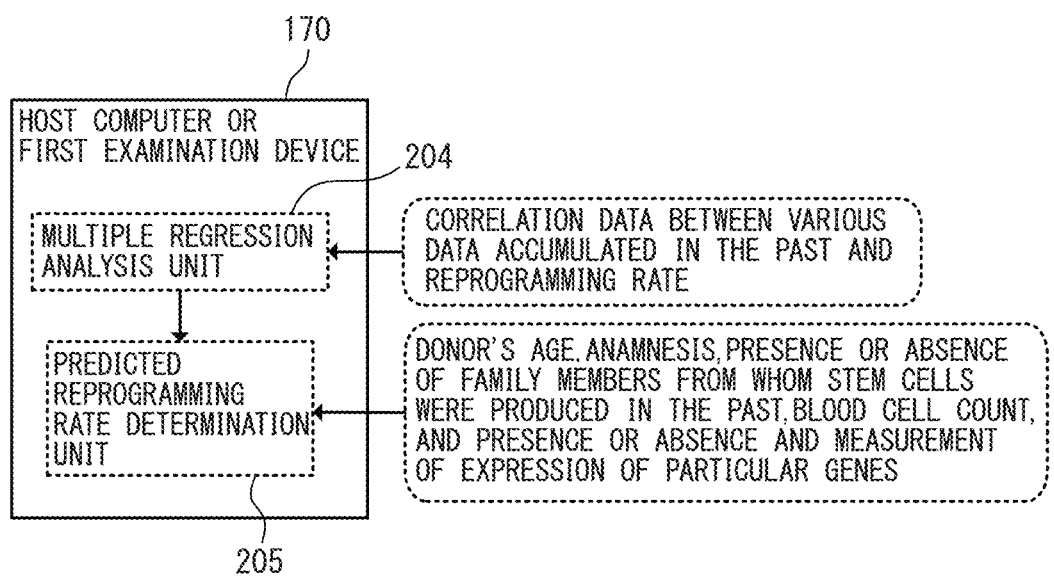
FIG. 29 is a functional block diagram of the first examination device according to an embodiment.
Figure 30:
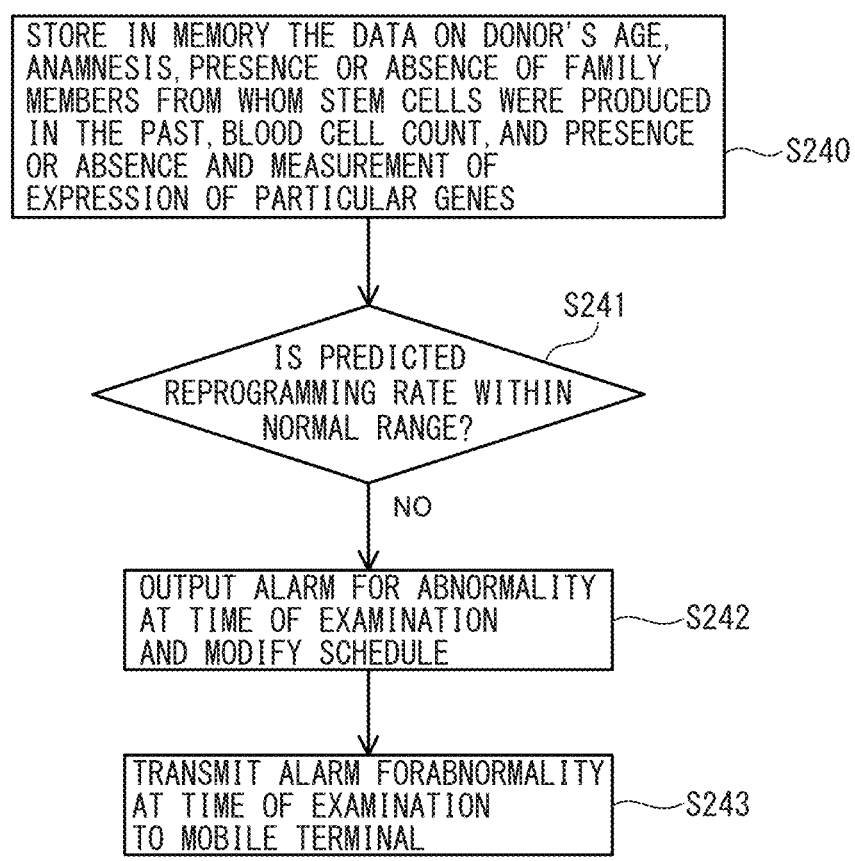
FIG. 30 is a flow chart illustrating an examination operation of the stem cell information management system according to an embodiment.

FIG. 28 to FIG. 30 illustrate a configuration and an operation of the stem cell information management system 200 in the examination process of somatic cells. As illustrated in FIG. 28, the stem cell information management system 200 further includes a first examination device 285 configured to perform examination as to whether or not the collected somatic cells can be easily reprogrammed, and the first examination device 285 includes at least one of a somatic cell counting device 286 for counting somatic cells (e.g., the number of T cells in 1 ml of blood, the number of NK cells, the number of B cells, and the like) and a gene expression level measurement device 287 for measuring expression of particular genes. The first examination device 285 further includes a memory 288 storing various data, a communication control unit 289 in a wireless or wired communication with the server apparatus 201 serving as the superordinate computer, and a CPU 290 controlling the whole first examination device 285, stores in the memory 288 the measured somatic cell count and the presence or absence or amount of expression of particular genes in association with the donor ID, and transmits the information to the server apparatus 201 serving as the superordinate computer 170. According to another embodiment, the first examination device 285 may include an HLA typing device, a genomic information examination device for examining genomic information, and the like.

As illustrated in FIG. 29, the server apparatus 201 serving as the superordinate computer 170 further includes a multiple regression analysis unit 204 that stores in a memory unit 202 correlation data between various data accumulated in the past and reprogramming rate and performs multiple regression analysis based on the correlation data, and a determination unit 205 that determines a predicted reprogramming rate for the somatic cell donor. According to another embodiment, the first examination device 285 may include the multiple regression analysis unit 204 and a predicted reprogramming rate determination unit 205, and transmit to the server apparatus 201 the predicted reprogramming rate, which is an indicator as to whether or not the somatic cells can be easily reprogrammed.

According to another embodiment, the server apparatus 201 may include a machine learning unit that learns data features and patterns based on multiple kinds of combinations of various data accumulated in the past and reprogramming rate and a predicted reprogramming rates determination unit that determines a predicted reprogramming rate based on the learned data features and patterns. According to still another embodiment, the server apparatus 201 may include a neural network production unit that produces a neural network based on multiple kinds of combinations of various data accumulated in the past and reprogramming rates and a predicted reprogramming rate determination unit that determines a predicted reprogramming rate based on the produced neural network. Furthermore, it should be recognized that deep learning and AI may be utilized for the determination of a predicted reprogramming rate.

As illustrated in FIG. 30, the server apparatus 201 stores examination information from the first examination device (i.e., the somatic cell count, the presence or absence or amount of particular genes. According to another embodiment, HLA types, genomic information, SNPs, and the like may be included) in the memory unit 202, in association with at least the donor ID (step S240). The server apparatus 201 then determines a predicted reprogramming rate based on the age, anamnesis, family members from whom stem cells were produced in the past, of the donor, somatic cell count, and the presence or absence and amount of particular genes stored in memory and, when the predicted reprogramming rate is out of the normal range (e.g., less than 50%) (step S241), the server apparatus 201 determines to output an alarm for an abnormality at the time of examination and modify the schedule (step S242) and transmits the alarm for an abnormality at the time of examination and the examination information to the mobile terminal 180 in a remote location (step S243).

Figure 31:
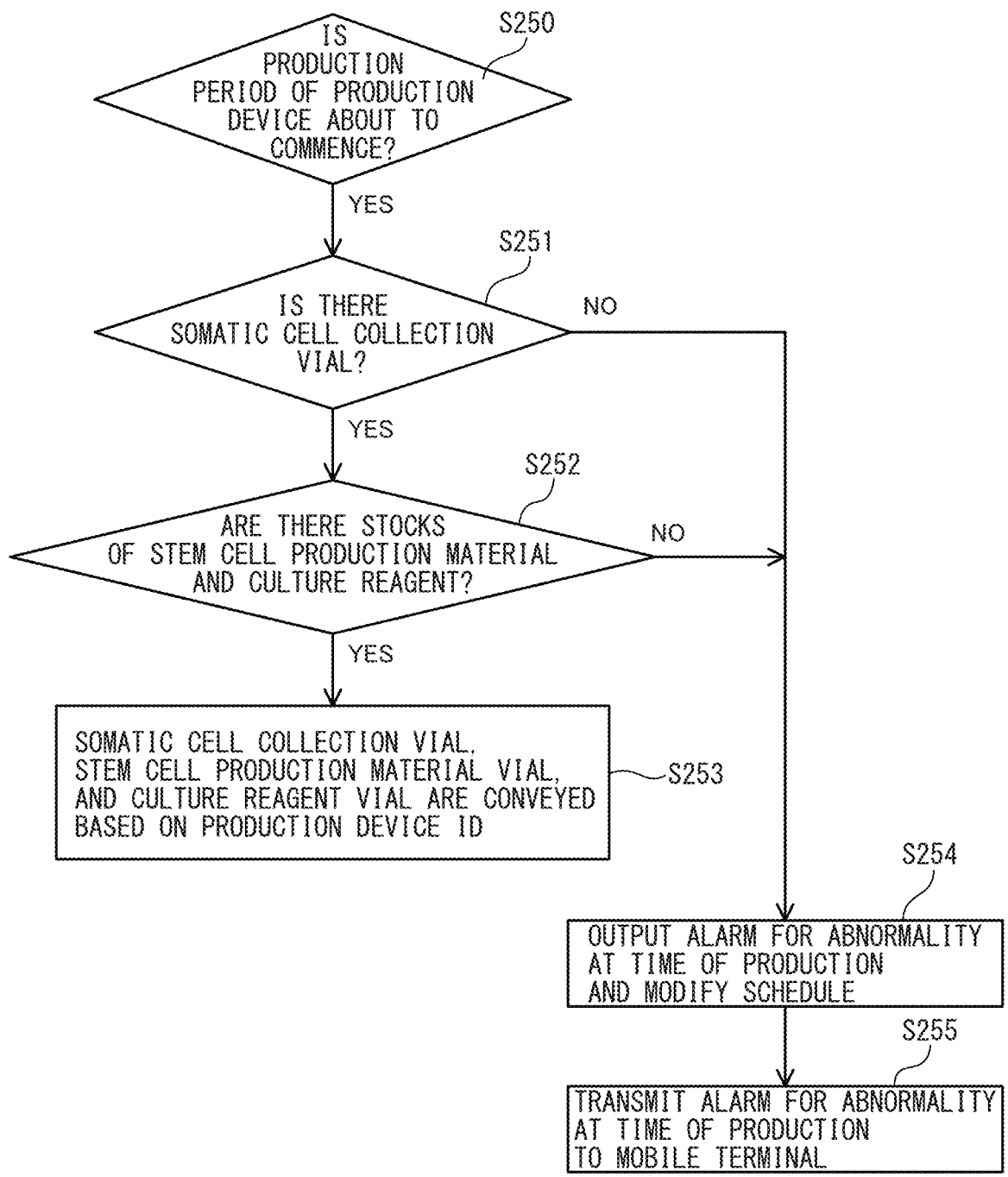
FIG. 31 is a flow chart illustrating a production operation of the stem cell information management system according to an embodiment.
Figure 32:
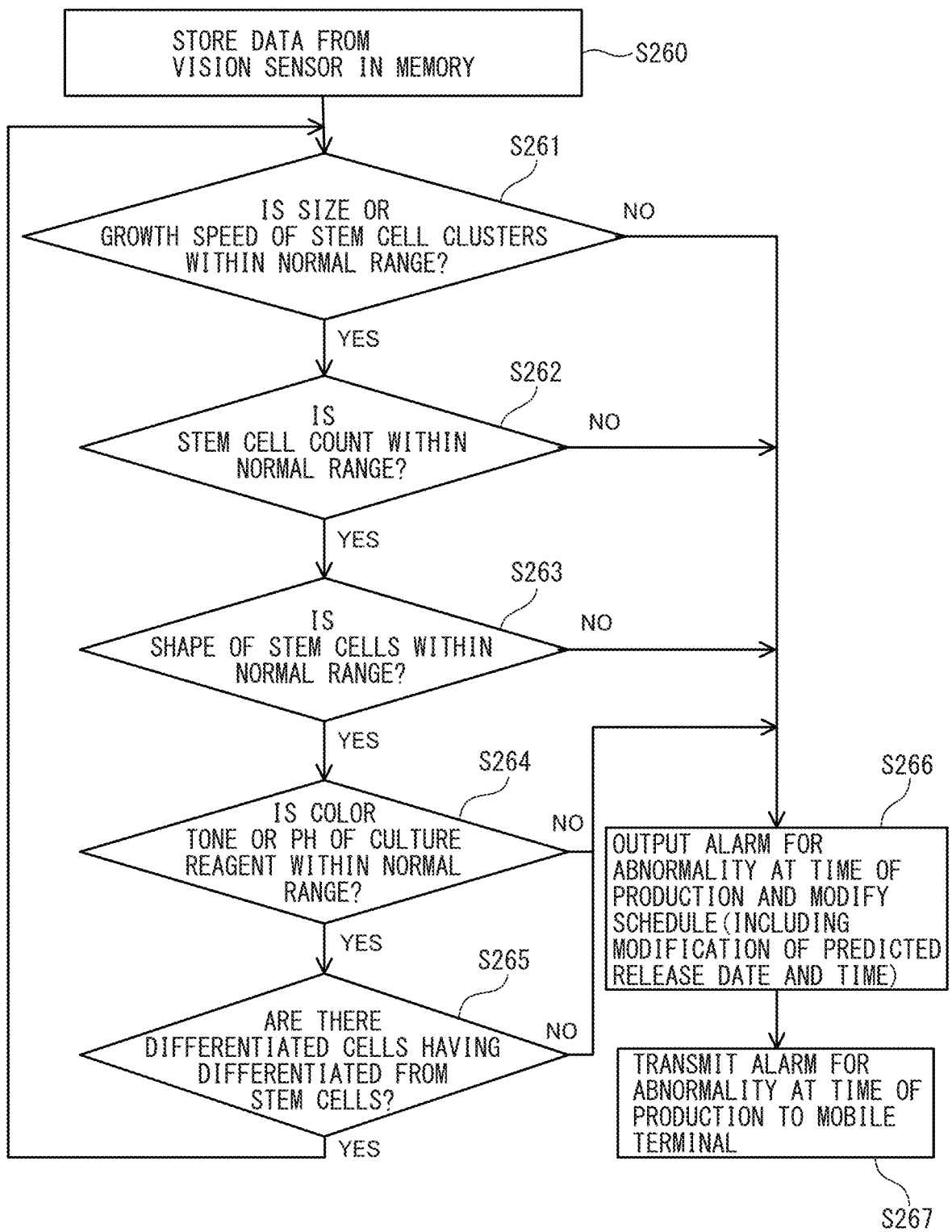
FIG. 32 is a flow chart illustrating a production operation of the stem cell information management system according to an embodiment.
Figure 33:
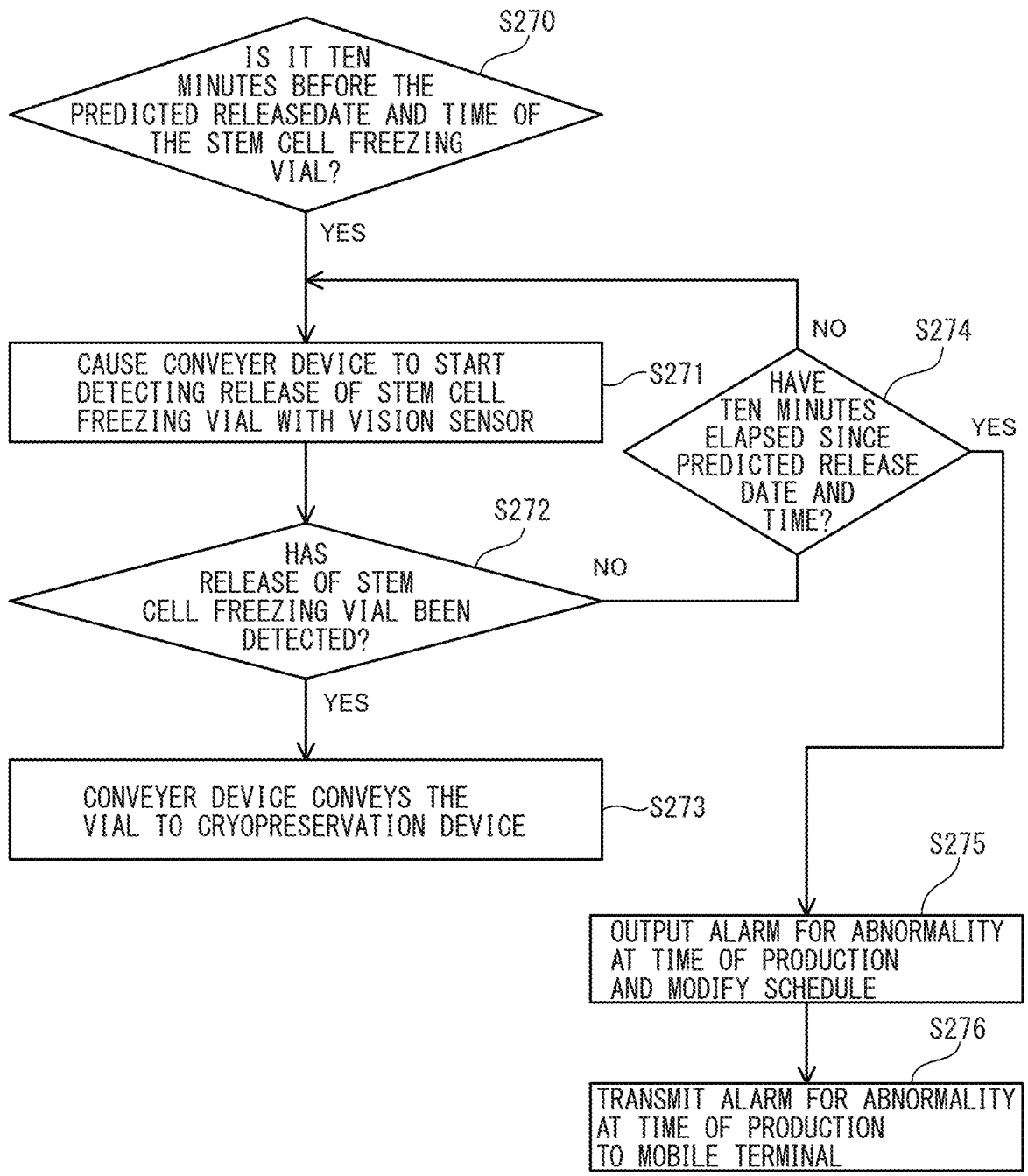
FIG. 33 is a flow chart illustrating a production operation of the stem cell information management system according to an embodiment.

FIG. 31 to FIG. 33 are flow charts illustrating operations of the stem cell information management system 200 in the manufacturing process. The stem cell information management system 200 further includes a conveyer device 140 (see FIG. 1) that conveys at least one of a somatic cell collection vial 102, a stem cell freezing vial 103 (empty vial), a stem cell production material vial 104, and a culture reagent vial 105 to the production device 101, based on the production device ID read from the vial, and a server apparatus 201 that stores in memory the stock information of the stem cell production material vial 104 and the culture reagent vial 105.

As illustrated in FIG. 31, when the server apparatus 201 has determined that the production period of the production device 101 determined at the time of receiving the request (step S250) is about to commence, the conveyer device 140 determines whether or not there is a somatic cell collection vial 102 (step S251), and when there is a somatic cell collection vial 102, the server apparatus 201 determines, based on the stock information of the stem cell production material and the culture reagent, stored in memory (step S252), to cause the conveyer device 140 to convey at least one of a stem cell production material vial 104 and a culture reagent vial 105. The conveyer device 140 conveys a somatic cell collection vial 102, a stem cell freezing vial 103 (empty vial), a stem cell production material vial 104, and a culture reagent vial 105 to the production device 101, based on the production device ID (step S253). When there is no somatic cell collection vial 102, or there is no inventory of at least one of stem cell freezing vials 103 (empty vial), stem cell production material vials 104, and culture reagent vials 105, the server apparatus 201 determines to output an alarm for an abnormality at the time of production and modify the schedule (step S254) and transmits the alarm for an abnormality at the time of production to the mobile terminal (step S255).

As illustrated in FIG. 32, the stem cell information management system 200 further includes a vision sensor for acquiring data in the production device 101 (e.g., the vision sensor 137 of the drive device 130 illustrated in FIG. 6), and the server apparatus 201 stores data from the vision sensor 137 in the memory unit 202 (step S260). The server apparatus 201 determines, based on the data from the vision sensor 137 stored in the memory, whether or not the size or growth speed of the stem cell clusters is within the normal range (step S261), whether or not the stem cell count is within the normal range (step S262), whether or not the shape of the stem cells is within the normal range (step S263), whether or not the color tone or pH of the culture reagent is within the normal range (step S264), and whether or not differentiated cells having differentiated from the stem cells are present (step S265). When any one of these pieces of production information is out of the normal range, the server apparatus 201 determines to output an alarm for an abnormality at the time of production and modify the schedule (including modifying the predicted release date and time) (step S266), and transmits the alarm for an abnormality at the time of production and the production information to the mobile terminal 180 in a remote location (step S267).

As illustrated in FIG. 33, when the server apparatus 201 has determined that it is ten minutes before the predicted release date and time of the stem cell freezing vial 102 determined at the time of receiving the request (step S270), the server apparatus 201 causes the conveyer device 142 to start detecting a release of a stem cell freezing vial 103 with the vision sensor 145 (step S271). When the conveyer device 142 detects a release of a stem cell freezing vial 103 (step S272), the conveyer device 142 conveys the stem cell freezing vial 103 to the cryopreservation device 120 (step S273). When the conveyer device 142 does not detect a release of a stem cell freezing vial 103 at the predicted release date and time (step S274), the conveyer device 142 repeats the detection until ten minutes elapse from the predicted release date and time, and when ten minutes have elapsed, the server apparatus 201 outputs an alarm for an abnormality at the time of production and modifies the schedule (step S275) and transmits the alarm for an abnormality at the time of production and the production information to the mobile terminal 180 in a remote location (step S276).

Figure 34:
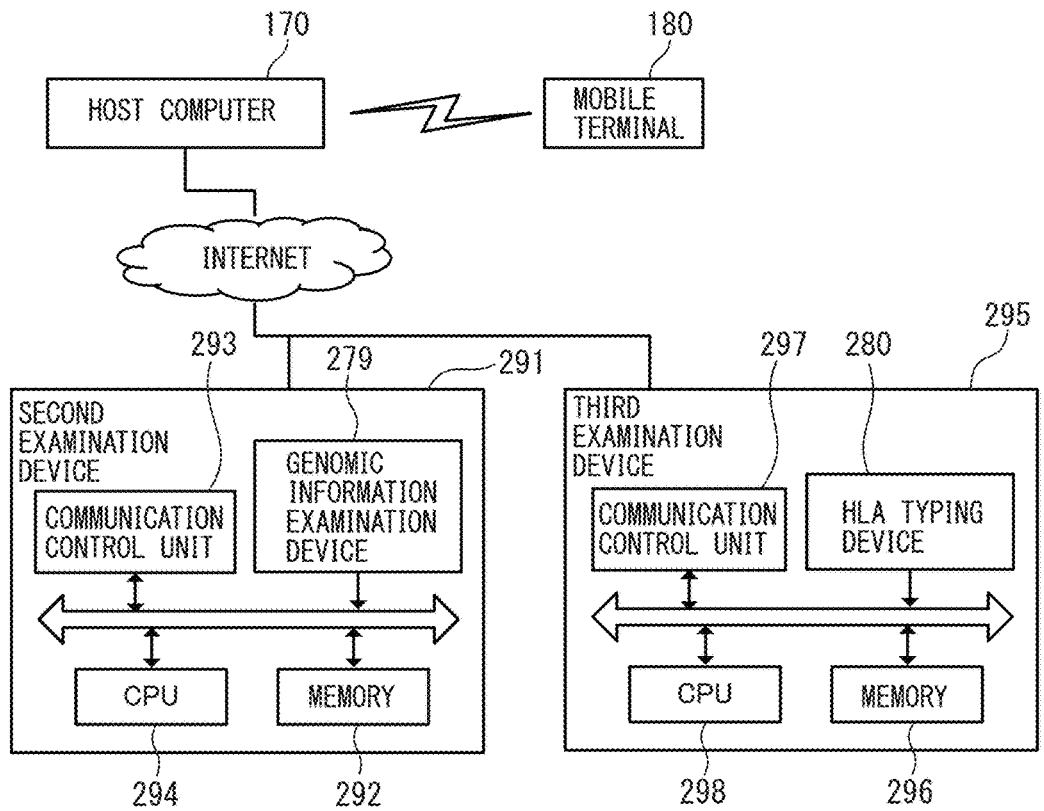
FIG. 34 is a block diagram illustrating a second examination device and a third examination device according to an embodiment.

FIG. 34 to FIG. 37 illustrate a configuration and an operation of the stem cell information management system 200 in the examination process of stem cells. As illustrated in FIG. 34, the stem cell information management system 200 further includes at least one of a second examination device 291 that includes a genomic information examination device 279 for somatic cells and stem cells, and a third examination device 295 that includes an HLA typing device 280 examining HLA types of somatic cells and stem cells. The second examination device 291 or the third examination device 295 further includes a memory 292, 296 storing various data, a communication control unit 293, 297 in a wireless or wired communication with the server apparatus 201 serving as the superordinate computer, and a CPU 294, 298 controlling the whole second examination device 291 or the whole third examination device 295, and stores in a memory 292, 296 the genomic information measured of the somatic cells and the stem cells or the HLA types measured of the somatic cells and the stem cells in association with the donor ID read from the vial, and transmits the genomic information or the HLA types to the server apparatus 201 serving as the superordinate computer 170. According to another embodiment, the stem cell information management system 200 may include both of the second examination device 291 and the third examination device 295. According to still another embodiment, the stem cell information management system 200 may include a fourth examination device that examines SNPs or genome sequences of somatic cells and stem cells.

Figure 35:
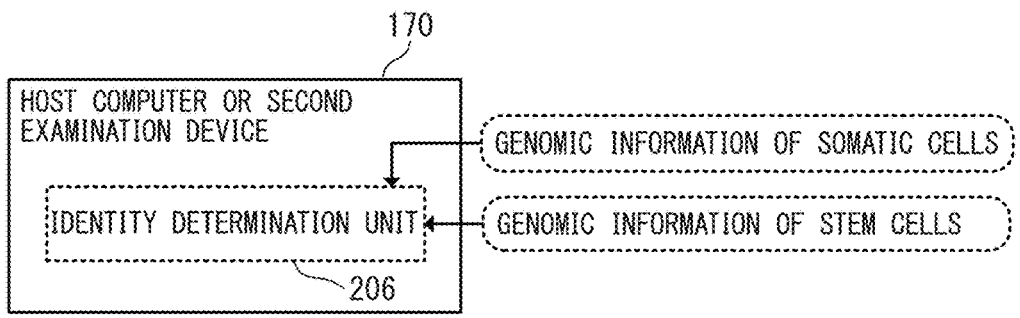
FIG. 35 is a functional block diagram of the second examination device according to an embodiment.
Figure 36:
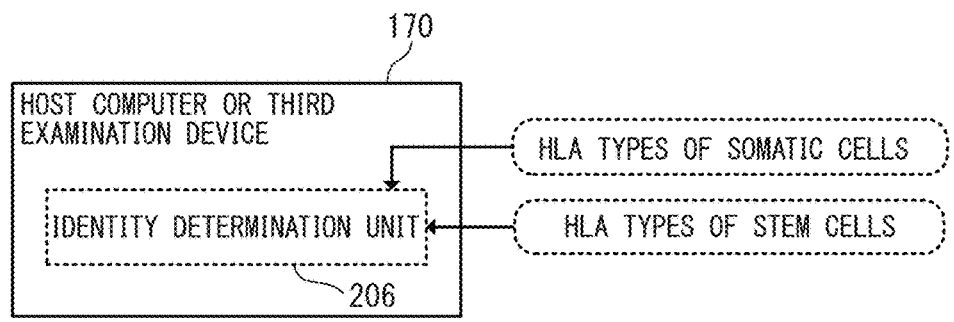
FIG. 36 is a functional block diagram of the third examination device according to an embodiment.

As illustrated in FIG. 35 and FIG. 36, the server apparatus 201 serving as the superordinate computer 170 further includes an identity determination unit 206 that determines whether or not the genomic information of the somatic cells is identical to that of the stem cells, or whether or not the HLA types of the somatic cells are identical to those of the stem cells. According to another embodiment, the second examination device 291 or the third examination device 295, not the server apparatus 201, may include the identity determination unit 206. According to still another embodiment, the server apparatus 201 may include an identity determination unit that determines whether or not the SNPs or genome sequences are identical.

Figure 37:
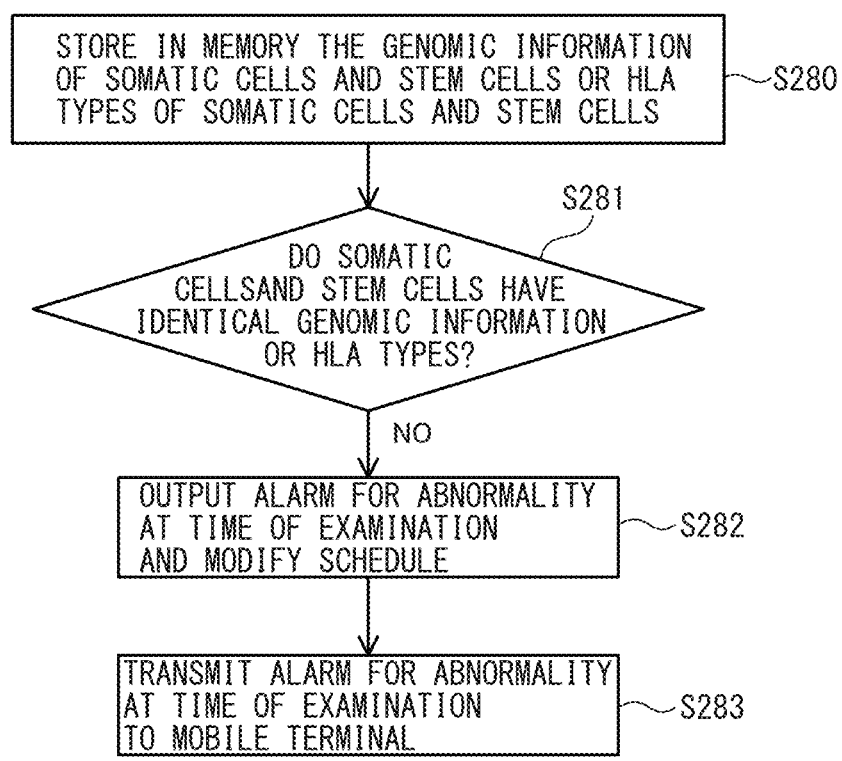
FIG. 37 is a flow chart illustrating an examination operation of the stem cell information management system according to an embodiment.

As illustrated in FIG. 37, the server apparatus 201 stores the examination information from the second examination device 291 or the third examination device 295 (i.e., genomic information or HLA types of the somatic cells and the stem cells) in the memory unit 202 in association with the donor ID read from the vial (step S280). When the genomic information or the HLA types are not identical between the somatic cells and the stem cells (step S281), the server apparatus 201 determines to output an alarm for an abnormality at the time of examination and to modify the schedule (step S282), and transmits the alarm for an abnormality at the time of examination and the examination information to the mobile terminal 180 in a remote location (step S283).

Figure 38:
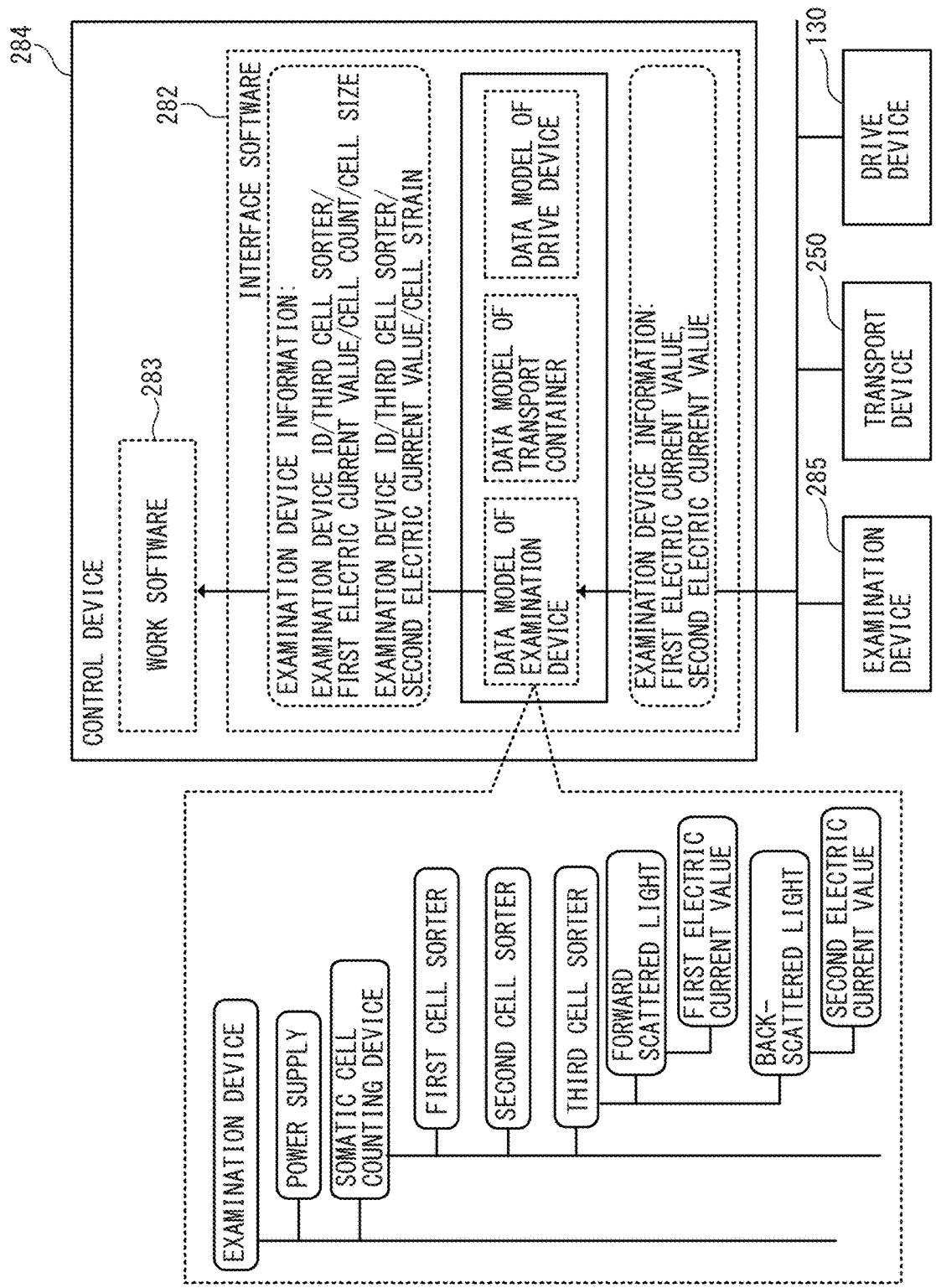
FIG. 38 is a functional block diagram of an application of the FIELD system to the stem cell information management system according to an embodiment.

FIG. 38 is a block diagram of an application of the FIELD system to the stem cell information management system 200 according to the present embodiment. The stem cell manufacturing system 200 further includes a control device 284 including interface software 282 and work software 283, and input devices connected by wired or wireless communication with the control device 284 and inputting information in respective processes. The input devices may be, for example, the transport container 250, the first examination device 285, and the drive device 130. According to another embodiment, the input devices may be, for example, input devices configured to input information in respective processes manually.

The control device 284, for example, receives a first electric current value of the forward scattered light and a second electric current value of the back-scattered light and the like of the first to the third cell sorters from moment to moment from the first examination device 285, receives temperature data from the temperature estimation unit, impedance from the somatic cell coagulation monitoring device, data from the vision sensor, and the like from moment to moment from one or more transport containers 250, and receives electric current values of the first to the fourth pumps, voltage values of the first to the third switches, data from the vision sensor, and the like from moment to moment from one or more drive devices 130. Since a large number of input devices of many kinds send out pieces of information unique to a large number of components of many kinds, it is not possible to recognize, for example, which cell sorter of which examination device is measuring cell count, cell sizes, cell strain, and the like. To address this, the interface software converts the information formatted in data formats unique to the input devices into information formatted in a data format unique to the work software. The data format unique to the work software is formed with data models having a data structure of tree type or network type indicating subordination relationship of the components of each input device, and the various data models are stored in a memory of the control device 284 in advance. To facilitate understanding, for example, a first electric current value and a second electric current value of the examination device 285, a piece of information unique to the input device, is converted to "examination device ID/third cell sorter/first electric current value/cell count/cell size", which is in a structured data format unique to the work software. This conversion gives the work software an instant access to data of a large number of components of many kinds in a large number of input devices of many kinds.

According to the above-described stem cell information management system 200, taking into consideration the production schedules of a plurality of closed production devices 101 at the time of receiving a manufacturing request, a schedule is determined according to the shortest route and the shortest time, which shortens the production time and provides a sophisticated quality control. At the time of receiving a request, the somatic cell collection vial 102 and the stem cell freezing vial 103 of the closed container are equipped with an individual identification device 106 containing the donor ID as well as at least one of the entry ID, the transport ID, the acceptance ID, the manufacturer ID, the production device ID, the cryopreservation device ID, and the stock site ID, which prevents cross contamination and ensures traceability in case of an abnormality. Furthermore, applying the FIELD system allows determination to output an abnormality alarm and modify the schedule at the time of transport, examination, manufacturing, and stock, based on big data from a large number of components of many kinds in a large number of input devices of many kinds, which shortens the production time, provides a sophisticated quality control, and solves human resource shortages.

3. Cell Transport Apparatus

Figure 39:
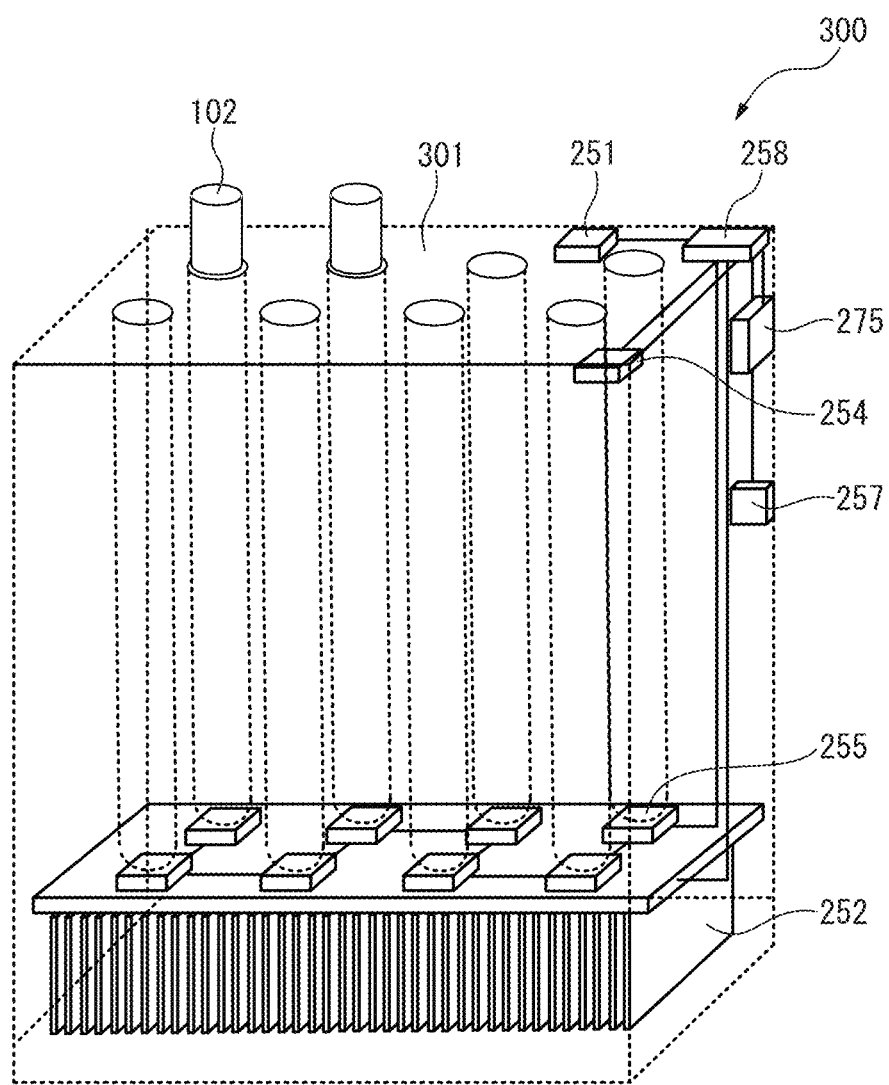
FIG. 39 is a perspective view of a somatic cell transport container of a cell transport apparatus according to an embodiment.
Figure 40:
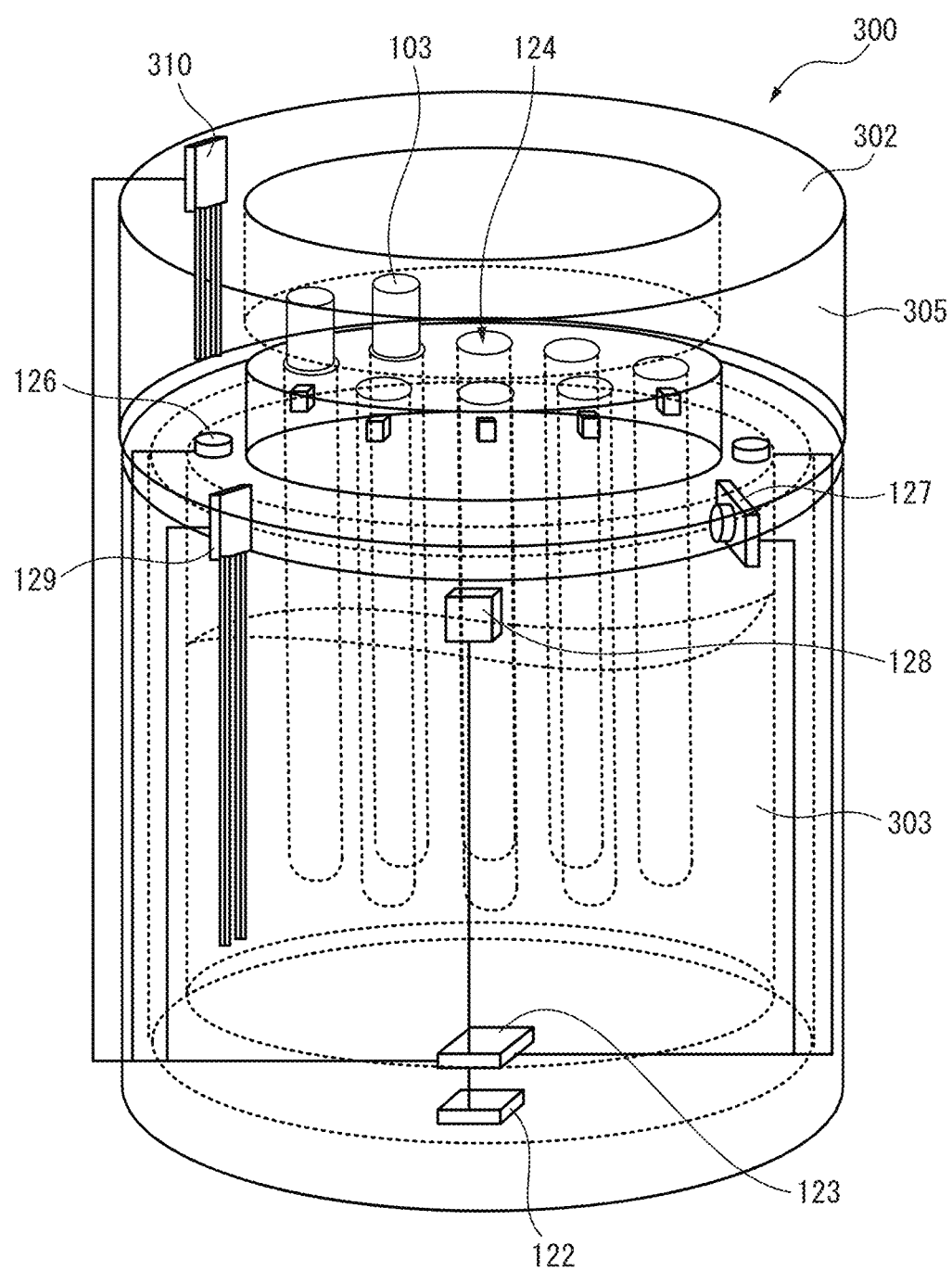
FIG. 40 is a perspective view of a stem cell transport container of the cell transport apparatus according to an embodiment.

FIG. 39 and FIG. 40 are perspective views of a somatic cell transport container 301 and a stem cell transport container 302 for the cell transport apparatus 300 according to the present embodiment. As illustrated in FIG. 39, the somatic cell transport container 301 is configured to contain one or more somatic cell collection vials 102 equipped with an individual identification device 106, which at least contain a donor ID, a production device ID, and the like. As illustrated in in FIG. 40, the stem cell transport container 302 is configured to contain one or more stem cell freezing vials 103 equipped with an individual identification device 106, which at least contains a donor ID, a production device ID, a stock site ID, and the like. According to another embodiment, the stem cell transport container 302 may be a cryopreservation device 120 illustrated in FIG. 5. Although a system in which iPS cells are produced from blood cells will be described according to the present embodiment, it should be understood that the invention can be applied to a system in which iPS cells are produced from skin-derived cells, a system in which ES cells are produced from embryonic cells, and other systems.

As illustrated in FIG. 2 and FIG. 14, the cell transport apparatus 300 further includes a reader device 107 configured to read the donor ID, the production device ID, the stock site ID, and the like contained in the individual identification device 106, and a transport means for transporting the somatic cell transport container 301 to the closed production device 101, based on the read production device ID, or transporting the stem cell transport container 302 to the stem cell stock site, based on the read stock site ID, and the transport means includes at least one of automobile, railway, aircraft, ship, and robot. According to this configuration of the cell transport apparatus 300, cross contamination is prevented even when stem cells are manufactured concurrently in one or more closed production device 101.

As illustrated in FIG. 23 and FIG. 24, the somatic cell transport container 301 further includes a heat retaining means for keeping the temperature inside the transport container constant, and the heat retaining means is a heating and cooling device 253 that includes a temperature estimation unit 259 estimating the temperature of the somatic cells in the transport container, and a heating and cooling unit 260 automatically performing heating or cooling in conjunction with the temperature data outputted by the temperature estimation unit 259 so that the temperature may be kept constant. The heating and cooling device 253 stores in memory an upper temperature limit and a lower temperature limit and, when the temperature data from the temperature estimation unit 259 is equal to or higher than the upper temperature limit or equal to or lower than the lower temperature limit, outputs a temperature-related abnormality alarm. According to another embodiment, the stem cell transport container 302 may include such a heating and cooling configuration.

Figure 41:
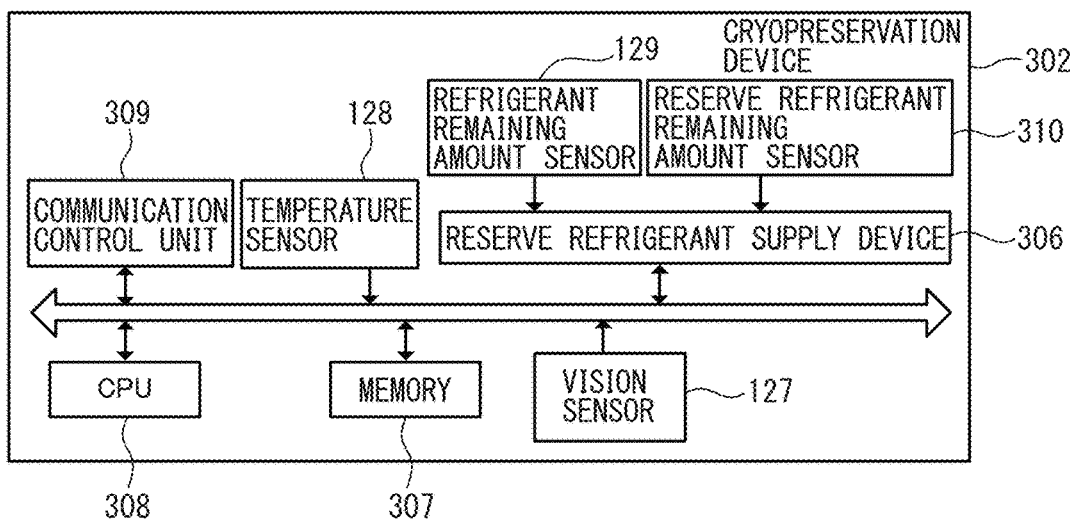
FIG. 41 is a block diagram of the stem cell transport container according to an embodiment.

FIG. 41 is a block diagram of the stem cell transport container 302 according to the present embodiment. As illustrated in FIG. 40 and FIG. 41, the stem cell transport container 302 includes a heat retaining means for keeping the temperature inside the transport container constant, and the heat retaining means includes a refrigerant 303 for cooling or freezing the stem cells in the transport container, a refrigerant remaining amount sensor 129 configured to detect the remaining amount of the refrigerant, a reserve tank 305 detachably connected with the transport container and containing reserve refrigerant, and a reserve refrigerant supply device 306 supplying reserve refrigerant, based on the remaining amount of the refrigerant. The stem cell transport container 302 further includes a memory 307 storing various data, a CPU 308 controlling the whole stem cell transport container, and a communication control unit 309 in a wireless communication with a superordinate computer. According to another embodiment, the somatic cell transport container 301 may include such a configuration for supplying reserve refrigerant.

As illustrated in FIG. 41, the stem cell transport container 302 further includes a reserve refrigerant remaining amount sensor 310 configured to detect the remaining amount of the reserve refrigerant, and a memory 307 configured to store an upper remaining amount limit and a lower remaining amount limit of the reserve refrigerant and, when the remaining amount of the reserve refrigerant is equal to or more than the upper remaining amount limit or equal to or less than the lower remaining amount limit, outputs a remaining-amount-related abnormality alarm. According to another embodiment, the somatic cell transport container 301 may outputs the remaining-amount-related abnormality alarm.

As illustrated in FIG. 24, the somatic cell transport container 301 and the stem cell transport container 302 may include an accumulated time measurement device 254 measuring accumulated transportation time, and the accumulated time measurement device 254 starts to measure the accumulated transportation time from the collection date and time of the somatic cells or the release date and time of the stem cell freezing vial from the closed production device. The accumulated time measurement device 254 stores in memory a time period during which the quality of the somatic cells or the stem cells can be maintained and outputs a time-related abnormality alarm when the accumulated transportation time exceeds the time period during which the quality can be maintained.

Figure 42:
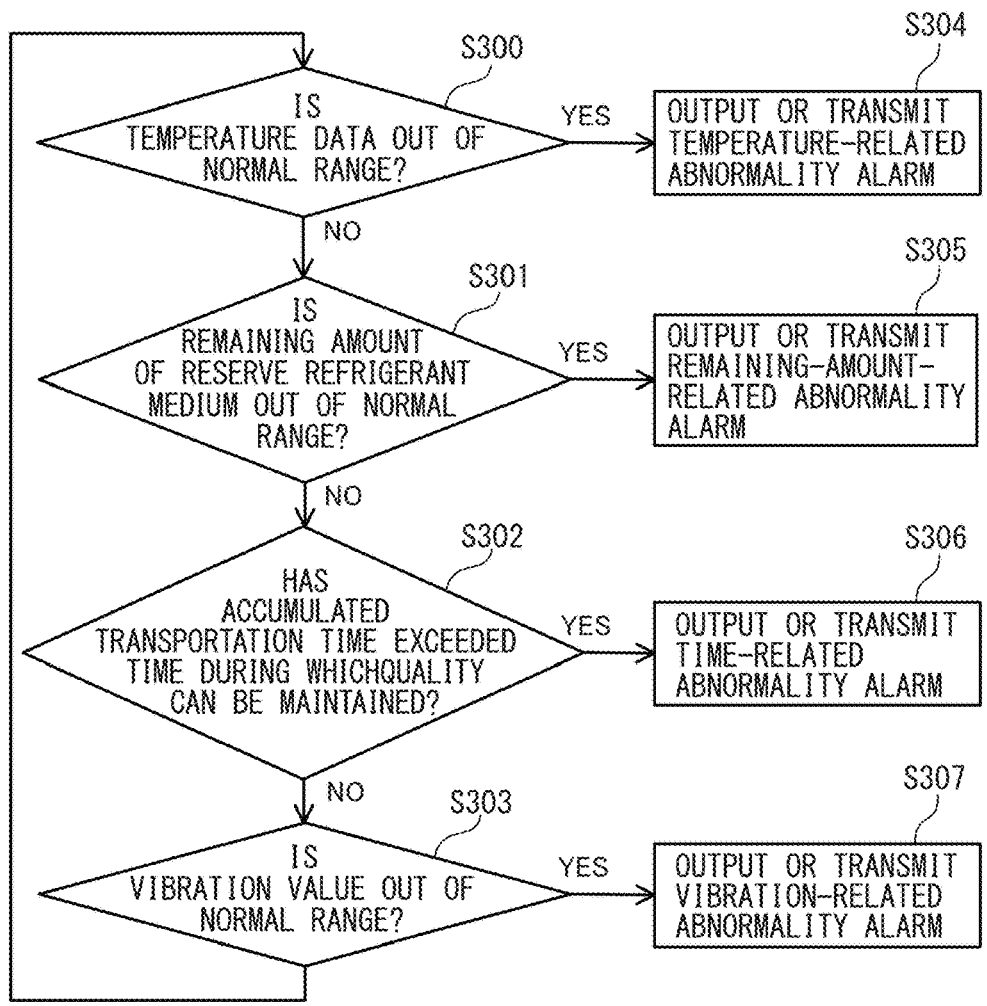
FIG. 42 is a flow chart illustrating an operation of the cell transport apparatus according to an embodiment.

FIG. 42 is a flow chart illustrating an operation of a cell transport apparatus 300 according to the present embodiment. When at least one of the data from the temperature estimation unit (step S300), the remaining amount of the reserve refrigerant (step S301), the accumulated transportation time (step S302), and the vibration value (step S303) is out of the normal range or within the abnormal range, the transport containers 301, 302 output a corresponding alarm among the temperature-related abnormality alarm (step S304), the remaining-amount-related abnormality alarm (step S305) the time-related abnormality alarm (step S306) and the vibration-related abnormality alarm (step S307), and transmit the alarm to the mobile terminal 180 in a remote location by wireless communication.

Figure 43:
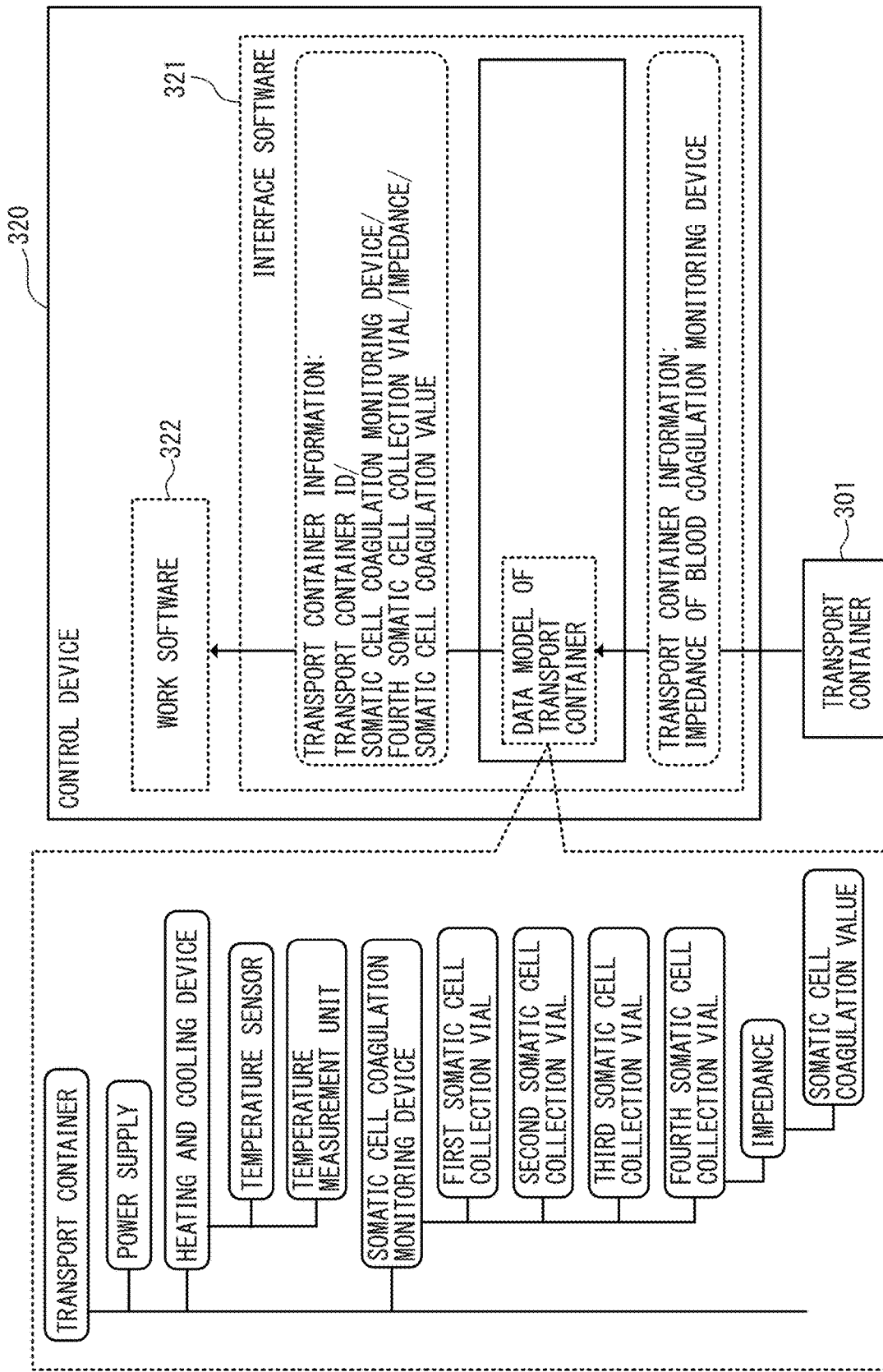
FIG. 43 is a functional block diagram of an application of the FIELD system to the cell transport apparatus according to an embodiment.

FIG. 43 is a functional block diagram of an application of the FIELD system to the cell transport apparatus 300 according to the present embodiment. The cell transport apparatus 300 further includes a control device 320 including interface software 321 and work software 322, and input devices connected by wired or wireless communication with the control device 322 and inputting information in the transport process. The input devices may be, for example, the above-described somatic cell transport container 301 and the stem cell transport container 302. According to another embodiment, the input devices may be input devices inputting information in the transport process.

The control device 320, for example, receives resistance values of the temperature sensor, temperature data from the temperature estimation unit, impedance of the somatic cell coagulation monitoring device, voltage values of the refrigerant remaining amount sensor, voltage values of the reserve refrigerant remaining amount sensor, data from the vision sensor, and the like from moment to moment from one or more transport containers 301, 302. Since a large number of input devices send out pieces of information unique to a large number of components of many kinds, it is not possible to easily recognize, for example, which vial of which transport container an impedance relates to. To address this, the interface software converts the information formatted in data formats unique to the input devices into information formatted in a data format unique to the work software. The data format unique to the work software is formed with data models having a data structure of tree type or network type indicating subordination relationship of the components of each input device, and the various data models are stored in a memory of the control device 320 in advance. To facilitate understanding, for example, an impedance of the somatic cell coagulation monitoring device of a transport container, a piece of information unique to the input device, is converted to "transport container ID/somatic cell coagulation monitoring device/fourth somatic cell collection vial/impedance/somatic cell coagulation value", which is in a structured data format unique to the work software. This conversion gives the work software an instant access to data of a large number of components of many kinds in a large number of input devices.

According to the above-described cell transport apparatus 300, since the somatic cell collection vial 102 contains the donor ID and the production device ID, or the stem cell freezing vial 103 contains the donor ID, the production device ID, and the stock site ID, cross contamination is prevented and traceability in case of abnormality is ensured. Furthermore, applying the FIELD system allows an abnormality alarm to be outputted and transmitted instantly, based on information unique to a large number of components of many kinds in a large number of input devices, which provides a sophisticated quality control, shortens the production time, and solves human resource shortages.

4. Stem Cell Frozen Storage Apparatus

Figure 44:
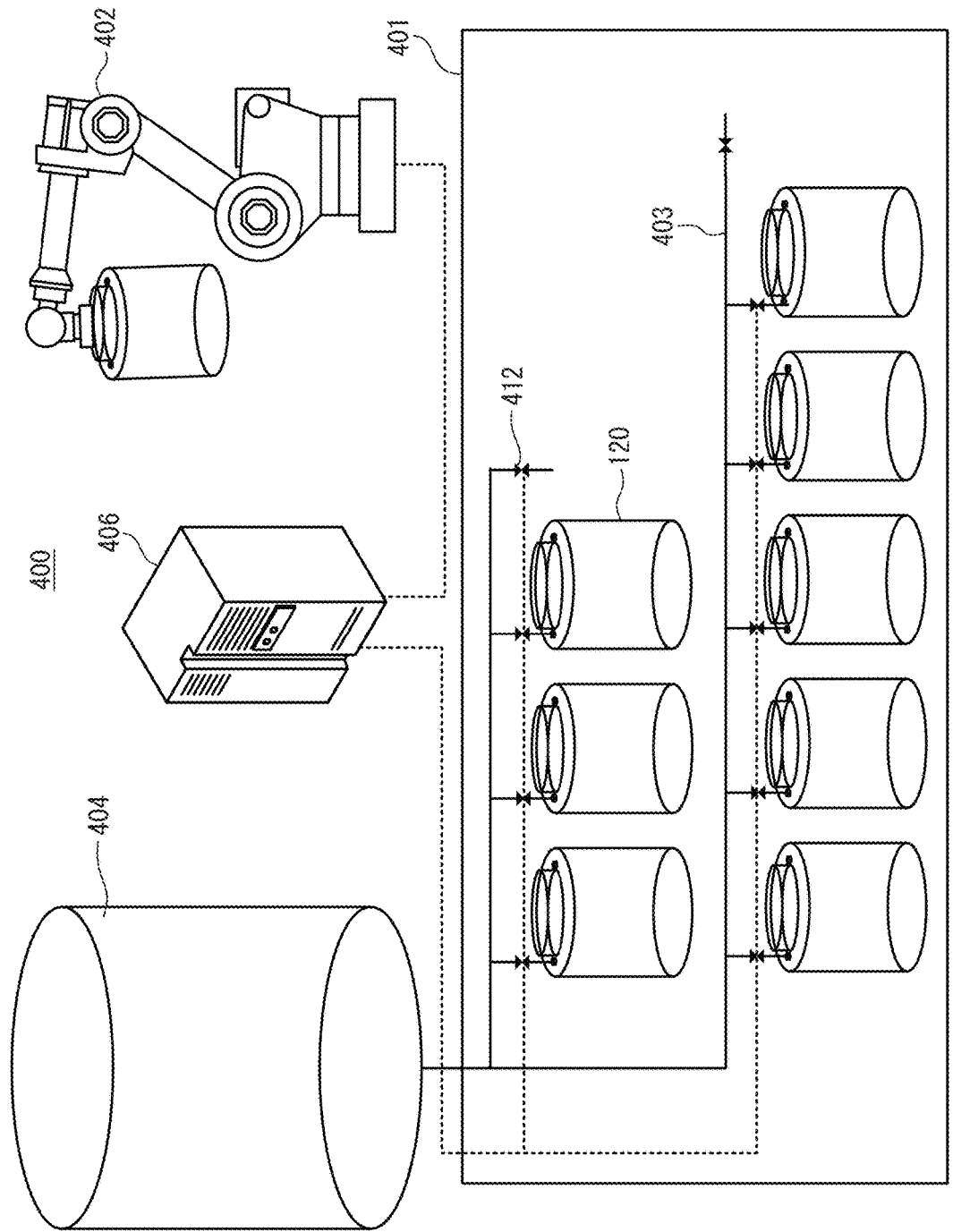
FIG. 44 illustrates a schematic configuration of a stem cell frozen storage apparatus according to an embodiment.
Figure 45:
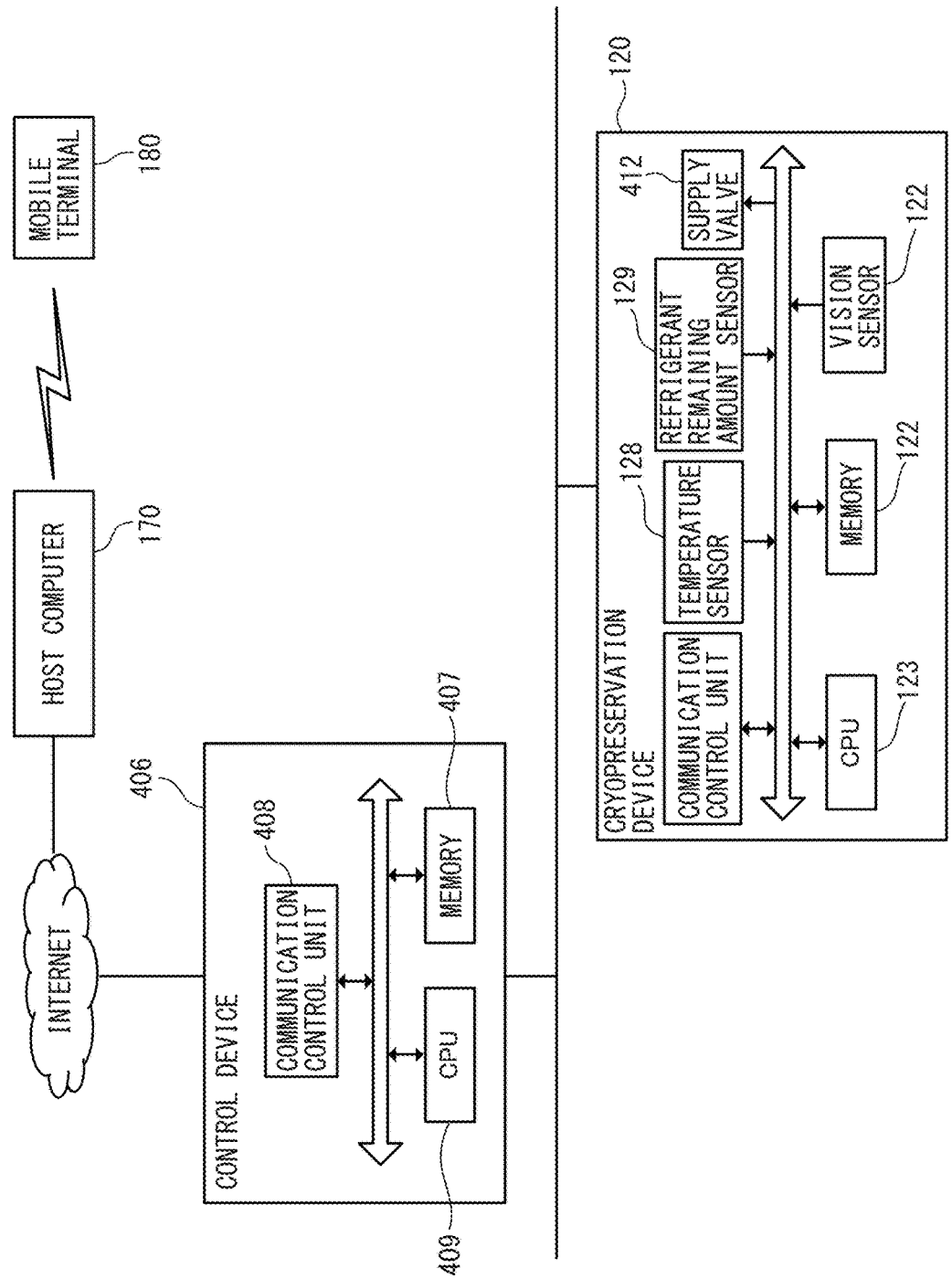
FIG. 45 is a block diagram of the stem cell frozen storage apparatus according to an embodiment.

FIG. 44 and FIG. 45 illustrate a configuration of the stem cell frozen storage apparatus 400 according to the present embodiment. As illustrated in FIG. 44, the stem cell frozen storage apparatus 400 includes one or more cryopreservation devices 120 configured to cryopreserve stem cell freezing vials 102, a storehouse 401 storing the cryopreservation devices 120, a conveyer device 402 configured to convey the cryopreservation devices 120 into and out of the storehouse 401, a refrigerant storage tank 404 connected with the one or more cryopreservation devices 120 via a refrigerant supply line 403. The conveyer device 402 is configured with a robot autonomously performing work according to a teaching program, and connects the one or more cryopreservation devices 120 with the refrigerant supply line 403.

As described with reference to FIG. 5, each cryopreservation device 120 includes a container unit 124 configured to contain one or more stem cell freezing vials 103 and a refrigerant chamber 125 configured to contain a refrigerant for freezing the stem cell freezing vial(s) 103, a refrigerant remaining amount sensor 129 configured to detect the remaining amount of the refrigerant, a temperature sensor 128 configured to measure temperature in the container unit 124, and a vision sensor 127 configured to detect presence of stem cells in the stem cell freezing vial(s) 103 (or presence of frozen liquid). The individual identification device 106 of each stem cell freezing vial 103 in the cryopreservation device 120 includes the donor ID as well as donor information including at least one of informed consent, nationality, address, sex, age, blood type, anamnesis, prescription history, health check results, and family members from whom stem cells are produced in the past, of the somatic cell donor. This makes it possible to easily identify the individual to whom the stem cell freezing vial 103 belongs to as well as the characteristics of the individual even in the stem cell stock site stocking many cryopreservation devices 120.

As illustrated in FIG. 5, the cryopreservation device 120 further includes a presence sensor 121 detecting presence or absence of a stem cell freezing vial 103. The stem cell frozen storage apparatus 400 further includes a conveyer device (not illustrated) configured to convey a stem cell freezing vial 103 into and out of the container unit 124 of the cryopreservation device 120, and the conveyer device (not illustrated) conveys a stem cell freezing vial 103 when there is no stem cell freezing vial 103 in the container unit 124 of the cryopreservation device 120, based on the detected presence or absence of a stem cell freezing vial 103. The conveyer device (not illustrated) is configured with a robot autonomously performing work according to a teaching program.

As illustrated in FIG. 44 and FIG. 45, the stem cell frozen storage apparatus 400 further includes a control device 406 monitoring and controlling operational status of one or more cryopreservation devices 120, based on information from at least one of the remaining amount sensor of the cryopreservation device(s) 120, the temperature sensor, and the vision sensor, and the control device 406 stores the operational status of the cryopreservation device(s) 120 in the memory 407 in association with time information and the donor ID and the like as record information. Further, the control device 406 stores in the memory 407 at least one of a normal range and an abnormal range of the operational status and, when the operational status is at least one of being out of the normal range and being within the abnormal range, outputs an abnormality alarm at least in association with the donor ID and transmits an abnormal alarm to a superordinate computer 170 or a mobile terminal 180 in a remote location by wired or wireless communication.

Figure 46:
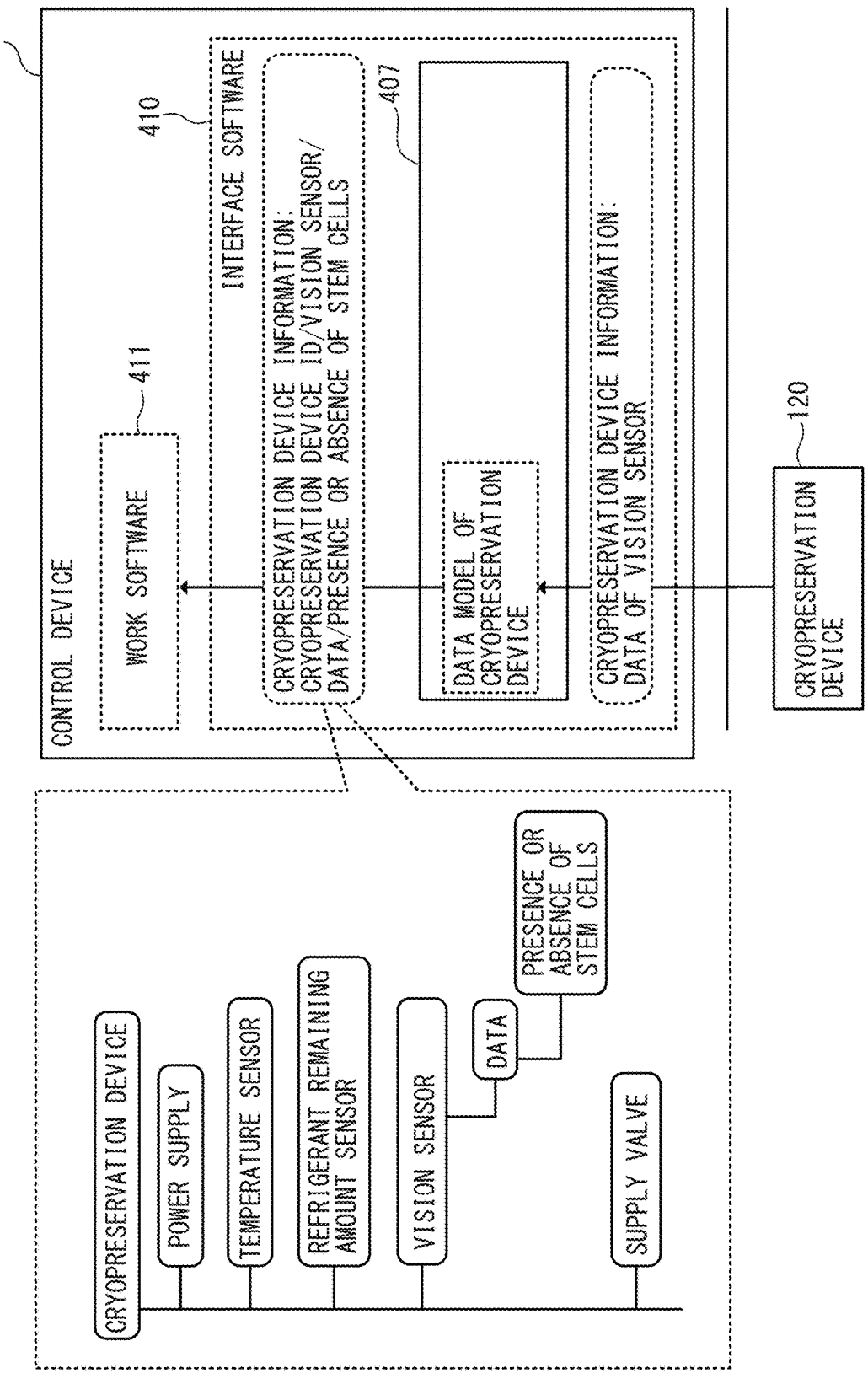
FIG. 46 is a functional block diagram of an application of the FIELD system to the stem cell frozen storage apparatus according to an embodiment.

FIG. 46 is a functional block diagram of an application of the FIELD system to the stem cell frozen storage apparatus 400. The control device 406 includes interface software 410, work software 411, and input devices connected by wired or wireless communication with the control device 406 and inputting information in the stock process. The input devices may be, for example, many cryopreservation devices 120. According to another embodiment, the input devices may be input devices configured to input information in the stock process.

The control device 406, for example, receives resistance values of the temperature sensor, voltage values of the remaining amount sensor, data form the vision sensor, voltage values of the supply valve 412, and the like from moment to moment from one or more cryopreservation devices 120. Since a large number of input devices send out pieces of information unique to a large number of components of many kinds, it is not possible to easily recognize, for example, to which component of which cryopreservation device 120 a certain voltage relates and what it indicates. To address this, the interface software converts the information formatted in data formats unique to the input devices into information formatted in a data format unique to the work software. The data format unique to the work software is formed with data models having a data structure of tree type or network type indicating subordination relationship of the components of each input device, and the various data models are stored in a memory of the control device 407 in advance. To facilitate understanding, for example, data from the vision sensor of a cryopreservation device 120, a piece of information unique to the input device, is converted to "cryopreservation device ID/vision sensor/data/presence or absence of stem cells (presence or absence of frozen liquid)", which is in a structured data format unique to the work software. This conversion gives the work software an instant access to data of a large number of components of many kinds in a large number of input devices.

The above-described stem cell frozen storage apparatus 400 allows the monitoring of the operational status of the cryopreservation device(s) 120 and management of the presence or absence of stem cells (or presence or absence of frozen liquid) in the cryopreservation device(s) 120 in a stem cell stock site with a long-term stock function. Furthermore, applying the FIELD system allows an abnormality alarm to be outputted and transmitted instantly, based on information from a large number of components of many kinds of many cryopreservation devices 120, which provides a sophisticated quality control, shortens the production time, and solves human resource shortages.

The software in the above-described embodiments may be provided by recording it in a machine-readable non-volatile recording medium, CD-ROM, or the like. Although various embodiments have been described herein, the present invention is not limited to the above-described embodiments, and it should be understood that various modifications can be made within the scope described in the appended claims.

The invention claimed is:

1. A stem cell manufacturing system for manufacturing stem cells from somatic cells, the system comprising:
   one or more stem cell producer(s) that produces stem cells from somatic cells;
   one or more drive device(s) that is connected with the stem cell producer(s), drives the stem cell producer(s), and maintains the stem cell producer(s) in an environment suitable for producing stem cells;
   one or more cryopreservor(s) that cryopreserves the produced stem cells;
   a first memory that stores data indicating whether or not somatic cells have been introduced to the stem cell producer(s), as a first state;
   a second memory that stores data indicating whether or not the stem cell producer(s) is/are connected with the drive device(s), as a second state;
   a third memory that stores data indicating whether or not the produced stem cells can be placed in the cryopreservor(s), as a third state; and
   one or more processor(s) that controls at least one of the first memory, the second memory, and the third memory.

2. The stem cell manufacturing system according to claim 1, further comprising an entry memory device that, upon receiving a request for manufacturing stem cells, stores donor information at least including information with which a somatic cell donor can be identified.

3. The stem cell manufacturing system according to claim 2, wherein the donor information includes at least one of informed consent, nationality, address, sex, age, blood type, anamnesis, prescription history, health check results, and family members from whom stem cells are produced in the past, of the somatic cell donor.

4. The stem cell manufacturing system according to claim 2, further comprising at least one of
   an input device that receives manual input of at least one of the first state, the second state, and the third state,
   a first vision sensor that acquires data for inputting at least one of the first state, the second state, and the third state, and
   a switch that feeds an electrical signal for inputting at least one of the first state, the second state, and the third state.

5. The stem cell manufacturing system according to claim 2, further comprising a first conveyer device that conveys at least one of somatic cells, a stem cell production material, and a culture reagent to the stem cell producer(s), the first conveyer device connected to the first memory and the second memory.

6. The stem cell manufacturing system according to claim 5, wherein the first conveyer device conveys at least one of somatic cells, a stem cell production material, and a culture reagent to the stem cell producer(s) when the first state stored in the first memory denotes a state in which somatic cells have not been introduced to the stem cell producer(s) and the second state stored in the second memory denotes a state in which the stem cell producer(s) is/are not connected with the drive device(s).

7. The stem cell manufacturing system according to claim 5, further comprising a second conveyer device that conveys the stem cell producer(s) to the drive device(s) or conveys the drive devices(s) to the stem cell producer(s), the second conveyer device connected with the second memory.

8. The stem cell manufacturing system according to claim 7, wherein the second conveyer device connects the drive device(s) to the stem cell producer(s) when the second state stored in the second memory denotes a state in which the stem cell producer(s) is/are not connected with the drive device(s).

9. The stem cell manufacturing system according to claim 7, further comprising a third conveyer device that conveys the produced stem cells from the stem cell producer(s) to the cryopreservor(s), the third conveyer device connected with the third memory.

10. The stem cell manufacturing system according to claim 9, wherein the first conveyer device, the second conveyer device, or the third conveyer device is a robot.

11. The stem cell manufacturing system according to claim 9, wherein at least two or three of the first conveyer device, the second conveyer device, and the third conveyer device are formed in a unitary body.

12. The stem cell manufacturing system according to claim 9, wherein the third conveyer device conveys the produced stem cells to the cryopreservor(s) when the third state stored in the third memory denotes a state in which the produced stem cells may be placed in the cryopreservor(s).

13. The stem cell manufacturing system according to claim 9, further comprising:
   a second vision sensor that acquires data in the stem cell producer(s), an examination window for conducting visual examination into the stem cell producer(s), a display device that displays data in the stem cell producer(s), or a removal unit for taking out a sample released from the stem cell producer(s); and
   a fourth memory that stores data indicating whether or not the stem cells being produced are in a normal condition, as a fourth state in numerical form, based on at least one of the data from the second vision sensor, a visual examination through the examination window, a visual examination based on the data displayed by the display device, and a sample taken out from the removal unit.

14. The stem cell manufacturing system according to claim 13, wherein the fourth memory stores at least one of a normal range and an abnormal range of the fourth state as first information, and wherein, when the fourth state is at least one of being out of the normal range or being within the abnormal range stored as the first information, at least one or more operations of outputting a first abnormality alarm, of halting the drive device(s), of changing the culture reagent by the first conveyer device, of connecting a different the stem cell producer(s) with the drive device(s) by the second conveyer device, and of rescheduling a production schedule are performed.

15. The stem cell manufacturing system according to claim 14, wherein the fourth state stored in the fourth memory denotes at least one of the size or growth speed of stem cell clusters, the ratio between stem cell clusters of different sizes, number of stem cells, shape of stem cells, temperature of stem cells, color tone or pH of culture reagent, and presence or absence of differentiated cells.

16. The stem cell manufacturing system according to claim 14, further comprising:
   a storage that preserves at least one of somatic cells, a stem cell production material, and a culture reagent; and
   a fifth memory that stores an inventory quantity of at least one of the stem cell production material and the culture reagent in the storage, as a fifth state.

17. The stem cell manufacturing system according to claim 16, wherein the fifth memory stores an arrival schedule of at least one of the stem cell production material and the culture reagent, the arrival schedule being included in the fifth state.

18. The stem cell manufacturing system according to claim 16, further comprising a sixth memory that stores a predefined standard state, wherein the sixth memory stores, as a sixth state, data indicating presence or absence of difference between the predefined standard state and at least one of the first state, the second state, the third state, the fourth state, and the fifth state.

19. The stem cell manufacturing system according to claim 18, wherein, when the sixth state denotes the presence of a difference, at least one of outputting a second abnormality alarm and halting the drive device(s) is performed.

20. The stem cell manufacturing system according to claim 19, further comprising:
   at least one of a third vision sensor that acquires data in the cryopreservor(s), a temperature sensor that detects temperature in the cryopreservor(s), and a refrigerant remaining amount sensor that detects a remaining amount of refrigerant in the cryopreservor(s); and
   a seventh memory that is connected with at least one of the third vision sensor, the temperature sensor, and the refrigerant remaining amount sensor, and stores, as a seventh state in numerical form, whether or not the stem cells being stored are in a normal condition, based on at least one of data from the third vision sensor, temperature data from the temperature sensor, and the remaining amount of refrigerant from the refrigerant remaining amount sensor.

21. The stem cell manufacturing system according to claim 20, wherein the seventh memory stores at least one of a normal range and an abnormal range of the seventh state as a second information, and wherein a third abnormality alarm is output when the seventh state is one of being out of the normal range or in the abnormal range stored as the second information.

22. The stem cell manufacturing system according to claim 21, wherein at least one or more of the first abnormality alarm, the second abnormality alarm, and the third abnormality alarm are either outputted in association with the donor information or transmitted to a mobile terminal in a remote location by wireless communication.

23. The stem cell manufacturing system according to claim 21, further comprising an eighth memory that stores, as an eighth state, at least one of operation records of the first to the third conveyer devices, an operation record of the drive device(s), and an operation record of the cryopreservor(s), wherein the sixth state includes presence or absence of a difference between the eighth state and the predefined standard state.

24. The stem cell manufacturing system according to claim 23, wherein at least one or more of the first state, the second state, the third state, the fourth state, the fifth state, the sixth state, the seventh state, or the eighth state are stored in memory in association with the donor information.

25. The stem cell manufacturing system according to claim 23, wherein at least one or more of the first state, the second state, the third state, the fourth state, the fifth state, the sixth state, the seventh state, or the eighth state are transmitted to a mobile terminal in a remote location by wireless communication.

26. The stem cell manufacturing system according to claim 23, wherein at least two or more of the first memory, the second memory, the third memory, the fourth memory, the fifth memory, the sixth memory, the seventh memory, and the eighth memory are housed in a unitary body.

27. The stem cell manufacturing system according to claim 2, wherein a container for containing at least one of somatic cells, stem cells, a stem cell production material, and a culture reagent is equipped with an individual identification device.

28. The stem cell manufacturing system according to claim 27, wherein the individual identification device is a semi-conductor chip, one-dimension code, or two dimension code containing data related to the donor information.

29. The stem cell manufacturing system according to claim 28, wherein the data related to the donor information includes at least one of entry identification information for identifying an entry of a request for manufacturing stem cells, transport identification information for identifying a transport of the container, acceptance identification information for identifying an acceptance of the container, stem cell producer identification information for identifying a stem cell producer, the cryopreservor identification information for identifying a the cryopreservor cryopreserving the container, and stock site identification information for identifying a stock site in which the cryopreservor(s) is stocked.

30. The stem cell manufacturing system according to claim 1, further comprising:
   a control device comprising interface software and work software, and
   an input device in wired or wireless communication with the control device to input information in a manufacturing process,
   wherein the interface software converts information formatted in a data format unique to the input device into information formatted in a data format unique to the work software.

31. The stem cell manufacturing system according to claim 1, wherein the somatic cells are blood cells or fibroblasts.

32. The stem cell manufacturing system according to claim 1, wherein the stem cells are iPS cells.

* * * * *